United States Patent
Giles et al.

(10) Patent No.: US 11,478,656 B2
(45) Date of Patent: Oct. 25, 2022

(54) APPARATUS FOR SYSTEMIC HUMAN ENHANCEMENT FROM ADMINISTRATION OF FREQUENCY THERAPY INCLUDING ENHANCED STEM CELL AND GENETIC THERAPY AND METHODS FOR USING SAME

(71) Applicant: Blair A. Souter, Sedona, AZ (US)

(72) Inventors: Brian C. Giles, Sedona, AZ (US); Blair A. Souter, Sedona, AZ (US)

(*) Notice: Subject to any disclaimer, the term of this patent is extended or adjusted under 35 U.S.C. 154(b) by 0 days.

(21) Appl. No.: 17/637,405

(22) PCT Filed: Aug. 24, 2020

(86) PCT No.: PCT/US2020/047699
§ 371 (c)(1),
(2) Date: Feb. 22, 2022

(87) PCT Pub. No.: WO2021/035222
PCT Pub. Date: Feb. 25, 2021

(65) Prior Publication Data
US 2022/0266046 A1  Aug. 25, 2022

Related U.S. Application Data

(60) Provisional application No. 62/890,214, filed on Aug. 22, 2019.

(51) Int. Cl.
*A61M 21/02* (2006.01)
*A61H 33/00* (2006.01)
(Continued)

(52) U.S. Cl.
CPC .............. *A61N 1/40* (2013.01); *A61H 1/005* (2013.01); *A61M 21/0094* (2013.01);
(Continued)

(58) Field of Classification Search
CPC ... A61M 21/02; A61H 33/0091; A61H 33/00; A61H 23/00; A61H 2201/0165;
(Continued)

(56) References Cited

U.S. PATENT DOCUMENTS 6,411,722 B1   6/2002 Wolf
9,527,608 B1 * 12/2016 Sotnikov .................. B64G 1/66
(Continued)

FOREIGN PATENT DOCUMENTS

WO   2017019136 A1   2/2017

OTHER PUBLICATIONS

"Unbalanced Occlusion Modifies the Pattern of Brain Activity During Execution of a Finger to Thumb Motor Task". Fantozzi M et al. May 17, 2019 (published online), Frontier in Neuroscience. vol. 13, No. 499. <URL:https://www.frontiersin.org/articles/10.3389/fnins.2019.00499/full>: pp. 1-4 (Year: 2019).*
(Continued)

*Primary Examiner* — Christine H Matthews
*Assistant Examiner* — Joshua Daryl D Lannu
(74) *Attorney, Agent, or Firm* — Invention To Patent Services; Alex Hobson

(57) ABSTRACT

A systemic human repair and enhancement system that provides stem cell therapy utilizing an apparatus and methods for administering a treatment schedule of non-invasive and drug-free narrow and specific 0.6180 Hz frequency continuous sine wave therapy to the patient's cells. The frequency therapy may be in-vivo and in-vitro applications. The frequency therapy stimulates systemic stem cell production, particularly at a tissue sites having loss of function due to a condition, aging, damage, and or disease. The frequency therapy system encompasses a narrow and specific ultra-low continuous sine wave frequency stimulation therapy that produces one or more of the enhanced cell
(Continued)

production, release, viability, proliferation, migration and or engraftment of the human patient's own genetically compatible stem cells, and the therapy enhances the stem cell's secretions thereby safely enhancing the secretion's therapeutic effects during stem cell therapy and simultaneously systemically enhancing the patient's pre-existing cells and tissues.

20 Claims, 15 Drawing Sheets

(51) Int. Cl.
    *A61N 1/00* (2006.01)
    *A61N 5/06* (2006.01)
    *G01N 29/34* (2006.01)
    *H04R 1/20* (2006.01)
    *H05K 9/00* (2006.01)
    *A61N 1/40* (2006.01)
    *C12N 5/09* (2010.01)
    *A61H 1/00* (2006.01)
    *A61M 21/00* (2006.01)

(52) U.S. Cl.
    CPC ........ *C12N 5/0693* (2013.01); *A61H 2201/10* (2013.01); *A61H 2201/105* (2013.01); *A61M 2202/0208* (2013.01); *C12N 2529/00* (2013.01)

(58) Field of Classification Search
    CPC .... A61H 2201/1657; A61N 1/00; A61N 5/06; G01N 29/348; H04R 1/20; H05K 9/0001
    See application file for complete search history.

(56) References Cited

U.S. PATENT DOCUMENTS

| | | | |
|---|---|---|---|
| 2004/0187680 A1* | 9/2004 | Kutt | ...................... A63B 23/18 55/385.2 |
| 2006/0052834 A1 | 3/2006 | Goroszeniuk | |
| 2010/0016850 A1 | 1/2010 | Ron Edoute et al. | |
| 2011/0304240 A1 | 12/2011 | Meitav | |
| 2016/0220782 A1* | 8/2016 | Otis | ...................... A61M 21/02 |

OTHER PUBLICATIONS

Fantozzi, M et al. "Unbalanced Occlusion Modifies the Pattern of Brain Activity During Execution of a Finger to Thumb Motor"; Frontiers in Neuroscience, vol. 13, No. 499; Publication [online]. May 17, 2019 [retrieved Oct. 30, 2020]. Retrieved from the Internet: <URL: https://www.frontiersin.org/articles/10.3389/fnins.2019.00499/full>; pp. 1-4.

* cited by examiner

FREQUENCY TREATMENT FLOW CHART

OPTIONAL FREQUENCY TREATMENTS CHART

US 11,478,656 B2

APPARATUS FOR SYSTEMIC HUMAN ENHANCEMENT FROM ADMINISTRATION OF FREQUENCY THERAPY INCLUDING ENHANCED STEM CELL AND GENETIC THERAPY AND METHODS FOR USING SAME

CROSS REFERENCE TO RELATED APPLICATIONS

This application claims the benefit of priority to U.S. provisional application No. 62/890,214, filed on Aug. 22, 2019; the entirety of which is hereby incorporated by reference herein.

BACKGROUND

Field of the Invention

This application relates generally to systemic non-invasive and drug free human enhancement treatment schedules further including frequency stimulation therapy and or enhancing stem cell therapies and or medical devices, more specifically, to stem cell frequency stimulating devices and methods for enhancing the patient's cells, stem cells, and or their secretions for systemic human enhancement.

Background of the Invention

Cellular Based therapies, including Stem Cell therapies is a rapidly expanding field of medicine and healthcare.

The scope of human disease is vast and involves loss of and or damage to cells, tissues, and or complete organs, such as but not limited to cancers, ocular disease, neurodegenerative disease, respiratory disease, endocrine diseases, and or cardiovascular disease. The result of these conditions and or other diseases is typically some degree of loss of function of particular cells, including entire organs as this eventually leads to compromised quality of life, disability, and or death.

Stem cell therapy involves the use of cells, and or in some cases fetal, umbilical cord, placenta-derived, adult, induced pluripotent, gonadal stem cells, further including human embryonic stem cells and/or their partially or fully differentiated cellular derivatives administered to treat a wide variety of conditions and or diseased and damaged cells and tissues for replacement and or regeneration, in particular those that affect individuals who are non-responsive to conventional surgical and or pharmacologic therapies.

Recent research studies have shown that there is a bidirectional communication between injured tissue and stem cells, and their secretions, having repair and regenerative characteristics, in that stem cells release micro-vesicles, and further include bio-stimulative effects such that these nanoparticles have become recognized as a critical means of intracellular communication in areas ranging from neurotransmission, to immune modulation, to infectious disease, and the like.

Furthermore there is a shift in focus from the stem cells themselves to their bio-active secretions and their localized micro-environmental efficacious effects.

It is currently understood in the prior art that each stem cell niche (binding point) and Local Tissue-Specific Stem Cell sits on an MSC-pericyte site.

In some prior art stem cell therapies, 'aging' has been expressed in vascular density and furthermore its relation to stem cell populations and their effects.

These stem cell secretions act as a 'curtain' of molecules (secretome—range of bioactive molecules that stem cells secrete) providing a wide variety of responses such as immune regulation, inhibiting scar tissue formation, increase in endothelial growth factors (angiogenesis), and or the like. Note this 'curtain' is currently theorized to create a camouflage to the immune system of sorts, which is why injected MSCs do not create an immune rejection (some claim they are 'immature' immunologically (do not display antigens), but more accurately it is the curtain that camouflages its detection).

The stem cell secreted trophic factors have a variety of significant beneficial effects such as but not limited to being anti-apoptotic, anti-scarring, angiogenic, and or mitotic.

The MSCs further secrete factors (secretome) that regulate the immune system to not hyper-express and or to inhibit the formation of scar tissue having a variety of immuno-modulatory effects on T-cells, B-cells, Dendritic Cells, T-regs, etc.

MSCs furthermore inhibit a wide variety of bacteria in part by secreting defensins (same as in mouth to regulate periodontal bacteria), that are shown to kill bacteria without harming other healthy cells.

Prior art stem cell technologies, including MSC based therapies have numerous significant limitations that are overcome by the current invention, such as but not limited to prior art therapies requiring a need to identify the type of disorder or specific disease to be therapeutically treated having costly, time consuming and risky step(s) of specifying the condition and or disease to be treated.

Note the use of embryonic stem cells in a clinical environment is often problematic due to embryonic stem cells are typically allogeneic (donor cells) to the human patient, as the embryonic stem cells rarely originate from that specific human patient. As a result, rejection of transplanted embryonic stem cells is a significant limitation. Likewise, the pluripotency of embryonic stem cell therapy does not guarantee differentiation into cells related to the damaged tissue.

Furthermore, the prior art stem cell therapies possess limitations such that antigenic stem cells are seen as foreign thus requiring immunosuppressive drugs during their therapy, and further having a significant limitation of a common outcome of Graft vs Host Disease response as a negative immune response to 'foreign' cells.

Conventional prior art stem cell therapies are moving in the direction which suggests it is not the actual stem cell, but rather the secretome or bioactive stem cell secretions, that create the beneficial effects.

The inventors theorize that when a non-allogeneic stem cell's host provides stem cells to a human patient, the transplanted stem cells can only respond to the proximate cellular or chemical micro-environment by essentially deflating (shrinking) thus secreting the bio-active molecules, and this significantly limits the stem cell's potential scope of systemic efficacy.

The inventors further theorize this stem cell release of its bio-active molecules (secretome) is caused from the recipient's immune system attacking these transplanted stem cells due to the patient rejecting the stem cells due to a genetic difference between the donor and patient.

The prior art is unaware of, overlooks, and or ignores the significant impact of stem cell rejection that is due to genetic differences.

The inventors theorize that genetic difference reduces the stem cell's potential effect, except for the process of the body fighting (rejecting) the genetically incompatible stem cells, thus releasing the bio-active stem cell components (secretome). This often occurs in virtually all donor recipient stem cell transplant therapies except for close relatives, and the further apart a recipient's and donor's genetic pattern, the more the body rejects it, having nearly 100% rejection of veterinary or animal stem cells, such as commonly employed bovine derived.

The prior art understanding that stem cell therapies are primarily a result of the stem cell secretome, rather than stem cell differentiation, is principally due to this genetic rejection of transplanted stem cells, which force the stem cells to exude their secretome.

The inventors further theorize that if cells are not in their correct location, including cellular micro-environment, the immune system will metabolize the cells, and this, in part, helps to coordinates much of the structure and organization of the human body, which is communicated through the interstitial fluid matrix and its corresponding mechanisms and functions.

The prior art stem cell therapy further requires significant complex preparation steps and or human intervention for stem cell therapies increasing potential human errors such as but not limited to mislabeling, mishandling, culturing and or re-administration steps (on average, conventional stem cell treatment requires about 3 to 16 treatments applications). Note medical error is the third leading cause of death in US (British Medical Journal—2016).

The prior art does not disclose nor teach how to frequency stimulate the production and or release of stem cells from the patient or subject.

Prior art stem cell treatment protocols and therapies have significant limitations, especially in time and cost with many (thousands) complex steps such as culturing and or differentiating/'selecting' requiring significant complex steps (with relatively low percentage of efficacy) for culturing specialized stem cells to be administered within the prior art's stem cell therapies, such as but not limited to complex extractions, Chemical Modifications, Induced Commitment, Cytoplast Extract Modification cells, Differentiation of cells, Donor Cell Preparations, Embryonic Stem Cell extractions, Embryonic Stem Cell Culturing and applications, Germ Cell Differentiation protocols, Primordial Germ Cells, Modified Germ Cells, Host Cell Extractions, Host Cell Preparations, Hybridization of Stem Cells, Induced Maturations, Multipotent and or Pluripotent stem cells, Extractions Processing and or Screening of Adult Progenitor Cells, Changing of petri dishes, Pre-embryonic Stem Cell Extractions and or Culturing, Post-natal Stem Cells, Pluripotent cells, Reprogramming and or Differentiation of iPSCs, Somatic Stem Cells, Therapeutic Reprogramming, and or further depict the many complexities of the prior art stem cell therapies and procedures.

The initial step includes extraction of the cells to be cultured, differentiation induced, and selected for. These stem cell sources all have different extraction and processing protocols, along with different efficacy potentials and limited applications (uses). Stem cell therapies of the prior art may be derived from a blastocyst (an embryo fertilized in vitro and grown approximately five days in culture) to then be converted to ES cells (embryonic stem cells) from the endoderm, mesoderm (mesenchymal Stem Cell) such as neural, heart, adipocyte, muscle, and the like. Administered stem cells may additionally be extracted from amniotic fluid, umbilical cord blood, further including adult cells that require leukophoresis (removing blood, separating WBCs and Stem cells, then culturing Stem Cells and then re-administering the stem cells and blood with cell growth hormones).

However, following the complexities and or potential risks of extraction, hESC lines are extremely difficult to grow in culture; the cells require highly specialized growth media that contain essential ingredients that are difficult to standardize. Yet the culture conditions are critical to maintain the stem cells' self-renewing and or pluripotent properties. Culturing often requires the support of mouse and or human cells, either directly as a "feeder" cell layer or indirectly as a source of conditioned medium in feeder-free culture systems. The feeder cells secrete important nutrients and otherwise support stem cell growth, but are treated so they cannot divide. Although the complete role of these feeder cells is currently not known, they promote stem cell growth, including detoxifying the culture medium and secreting proteins that participate in cell growth.

Following the extraction of adult somatic cells from the patient and or donor and biological conditions, these cells may further be converted in vitro to iPSCs (induced pluripotent Stem Cells), which then require additional specific extraction and or differentiation and or selection through a complex chemical culturing process. This reprogramming of Adult Somatic Cells to Become Pluripotent Stem Cells is accomplished through a variety of avenues such as induction of cells into hypoxic conditions and or viral induction of pluripotency.

Because of their pluripotency and capacity for self-renewal, stem cells hold great potential to renew tissues that have been damaged by conditions such as aging, type I diabetes, injuries, diseases such as Parkinson's disease and or C.T.E., heart attacks, and spinal cord injury and the like.

The current invention overcomes these and many prior art limitations not stated herein and is separate and distinct from prior art cellular based therapies, including stem cell therapies, and frequency based therapies such as frequency amino neuro frequency, PEMF (pulsed electromagnetic frequency), frequency based light and or sound neuropathy, radiofrequency electromagnetic frequency therapy, and the like.

Grant et al. patents US20160074277A1 titled System and method for titrating in vivo cellular reaction and gene expression using varying oscillation frequencies by Robert Edward Grant; Todd Mirzai; Matthew T. Case, US20170072215A1 titled Electromagnetic radiation techniques for in vivo tissue by Robert Edward Grant; Matthew T. Case, US20160076019A1 titled System and method for sonic radiation for influencing cellular structures by Robert Edward Grant; David Haydn Mordaunt; Matthew T. Case, US20160074669A1 titled: System and method for electromagnetic radiation for influencing cellular structures by Robert Edward Grant; Todd Mirzai; Matthew T. Case, US20160331988A1 titled: Waveform Energy Influence of Objects Using Feedback Control by Robert Edward Grant; Matthew T. Case; Todd Mirzai, US 20170143993A1 titled: Methods for employing digital root techniques to generate computer-input data by Robert Edward Grant, US20160262974A1 titled: Autonomic nervous system balancing device and method of use by Todd Mirzai; Robert Edward Grant; Matthew T. Case are insufficient to bring to a safe point of practice and obtain a predictable therapeutic outcome including obtaining the objects and providing the advantages stated therein.

Grant et al. patents discloses a required invasive highly complex titrating step(s) for measuring individual organ frequencies required for identifying the target tissue to be influenced (including the cellular structure), and by defining a desired phenotype for the target tissue. It is then necessary to establish values for the operational parameters (e.g. p, v and td) that will properly characterize the electromagnetic and or sonic radiation that is to be used. In particular, it is desirable to establish operational values that are operationally relative to the natural frequency of the target tissue (cellular structure). In detail, with knowledge of this natural frequency, the radiation frequency can be set to resonate, or partially resonate, with the cellular structure that is to be influenced during conduct of the treatment protocol. Similarly, Grant et al. requires physical characteristics of the tissue that is to be radiated must also be identified (e.g. tissue type, tissue volume, practical dimensions, fundamental frequencies, cellular structure, abnormalities, and various combinations of these). It happens that all of the operational parameters and tissue characteristics can each be somehow identified by a number. The respective numbers, however, can be lengthy and be either very large or extremely small. Moreover, they may be different from each other by many orders of magnitude. Despite such disparities, however, for operational purposes the numbers may need to be congruent with physical attributes of the target tissue. The current invention eliminates these complex steps.

FIELD OF THE INVENTION

The present application relates to apparatuses and methods administering a frequency based therapy for human genetic repair and or systemic enhancement and further improving the speed, safety and efficacy of various aspects of the frequency therapy, including stem cell therapy, emitting a 0.6180 Hz continuous sine wave having a narrow window of frequency variance. Several embodiments are directed to repairing, augmenting and enhancing one or more of the production, release, proliferation, delivery, differentiation, engraftment, and or functions of cells, including stem cells in general several prophetic examples are directed to enhancing neurologic function in human patients having a loss of one or more functions, including but not limited to, cognitive function, motor function, and the like, including that resulting from normal age-related degeneration, injury, and other neurological disorders, or any condition or disease of an unknown etiology. Other prophetic examples are directed to significantly enhancing the production and or release and or viability of stem cells and or enhancing their secretions produced from the human patient's own genetically matched stem cells to be employed in administering treatment schedules for medical research, more specifically research regarding systemic human enhancement.

SUMMARY OF THE INVENTION

Therapies employing live stem cells have emerged as a key element within the art of regenerative medicine primarily due to their inherent ability to produce multiple secreted factors under different conditions and or to differentiate into a wide variety of cell phenotypes, thereby providing numerous new potential cell therapies to treat a wide variety of conditions, disorders, diseases, traumatic injuries and or normal degenerative aging. Stem cell therapies is not just limited to cell and or organ repair, but is also due to their wide variety of secretions (secretome factors).

The current invention overcomes prior art limitations in frequency based therapies such as Grant et al. The prior art does not disclose nor teach sufficient methods and apparatuses for a frequency based system for practical application of therapies. Grant et al. does not disclose nor teach or ignores or is unaware of the necessary narrow and specific frequency nor does he disclose nor teach a specific wave form. Grant et al. does not disclose nor teach accurate metering and monitoring of administered dosage or dosages, including the total exposed dosages and or total absorbed dosages, further including a preferred distance between the frequency emitter and the patient (inverse square) nor does Grant et al. disclose nor teach the preferred exposed and or patient's absorbed dosage calculations as needed. Grant et al. does not disclose nor teach repair and or cell enhancement levels of action on the sub atomic scale. Grant et al. does not disclose nor teach a complete treatment schedule, nor does Grant et al. disclose nor teach pause times between treatments, including resting, recovery, and or testing periods. Grant et al. does not disclose nor teach administering the narrow and specific 0.6180 Hz sine wave frequency complete treatment schedule to a patient within a treatment pod. Grant et al. does not disclose nor teach administering the narrow and specific 0.6180 Hz sine wave frequency complete treatment schedule to a patient within a treatment containment shell. Grant et al. does not disclose nor teach administering the narrow and specific 0.6180 Hz sine wave frequency complete treatment schedule to a patient within a treatment capsule. Grant et al. does not disclose nor teach administering the narrow and specific 0.6180 Hz sine wave frequency complete treatment schedule to a patient within an immersion tank system. Grant et al. does not disclose nor teach administering the narrow and specific 0.6180 Hz sine wave frequency complete treatment schedule to a patient from a transportable handheld pistol wave emitter. Grant et al. does not disclose nor teach administering the narrow and specific 0.6180 Hz sine wave frequency complete treatment schedule to a patient from a vibrating table. Grant et al. does not disclose nor teach administering the narrow and specific 0.6180 Hz sine wave frequency complete treatment schedule to a patient within a hyperbaric chamber, preferably as an adjunct to hyperbaric therapy. Grant et al. does not disclose nor teach administering the narrow and specific 0.6180 Hz sine wave frequency complete treatment schedule to a patient from wristband emitters. Grant et al. does not disclose nor teach administering the narrow and specific 0.6180 Hz sine wave frequency complete treatment schedule to a patient from a probe emitter system.

Note some forms of energy administration frequency is toxic, and some are even lethal, and Grant et al. does not disclose nor teach any monitoring nor safety mechanisms, such as operator/practitioner verification. Grant et al. does not disclose nor teach optimized treatment environments, chambers, etc. such as interference frequency isolation and or cancelling, including interference frequency shielding apparatus, nor does Grant et al. disclose nor teach a frequency shielded or frequency isolated system, to generate and maintain and or monitor a highly accurate frequency and wave form. Grant et al. does not disclose nor teach onsite emergency applications. Grant et al. does not disclose nor teach enhancement of surgical procedures. Grant et al. does not disclose nor teach administering frequency therapy before, during, and or after surgical events. Grant et al. does not disclose nor teach narrow and specific frequency stimulation for enhancing stem cells, including their release, repair, enhancing stem cell secretions, etc., and further does not disclose nor teach specifically enhancing the patient's own stem cells (autologous stem cells). Grant et al. does not disclose nor teach frequency therapy for systemic genetic repair and genetic enhancement. Grant et al. does not disclose nor teach a frequency therapy treatment schedule for organ transplant, organ preservation, and or organ enhancement such as for transporting donor organs and extending the 'golden hour' for organs.

Grant et al. does not disclose nor teach a frequency therapy treatment schedule for blood enhancement and extending the 'golden hour' for organs. Grant et al. does not disclose nor teach frequency therapy for enhancing mental clarity and or improving mental health, including depression.

Note none of the prior art discloses nor teaches the systemic repair and enhancement of human genes i.e. enhancing of DNA. Note the average patient has about 400 genetic flaws. Additionally, the prior art does not disclose nor teach or is unaware of or ignores the fundamental interrelationship between quantum field dynamics and enhancement of human biological systems.

Grant et al. does not disclose nor teach administering the narrow and specific 0.6180 Hz sine wave frequency therapy administering from an antenna that is separate and distinct from a plasma antenna.

In a prophetic example the current invention provides previously unavailable significant therapeutic improvements that simplifies the apparatuses and methods for suppression and or complete remission of a wide variety of injuries, conditions and or diseased states, including those of unknown etiology, further including longevity assurance and significant extension of normal mortality, with systemic human enhancement encompassing simplifying and or enhancing stem cell therapies over all the prior art currently known to the inventor simultaneously improving safety, speed and or efficiency at a reduced time. In a prophetic example the current invention's ultra-low frequency therapy enhances the therapeutic potential of all cells and or their functions. This is an object of the invention.

The inventors theorize that stem cells are unspecified until they are specified, and the stem cells primarily mimics the cellular environment that is around them, and thus differentiate into those cells at the location that the stem cell is near, such as causing them to become muscle, causing them to become bone, and causing them to become something other than stem cells; differentiating into its own cell.

The phrase Ultra Low Frequency (ULF), as used herein refers specifically to the Ultra-Low Frequency administration of a narrow and specific frequency of 0.6180 Hz sine wave to a patient.

The phrase Frequency Stimulation Therapy (FST) as used herein specifically refers to the Frequency Stimulation Therapy of administering a narrow and specific frequency of 0.6180 Hz sine wave to a patient.

For the purposes of this disclosure the terms 'Ultra Low Frequency' and 'Frequency Stimulation Therapy' and their respective abbreviations ULF and FST may be interchangeable.

In a prophetic example the inventors theorize that stem cells may circulate throughout the patient's body, and when they find dead cells, they replenish them, such that any place that the patient's body needs repair, administration of a complete ULF treatment schedule encourages those stem cells and further create new cells, while the stem cells further secrete bio-active secretions in their localized area that is helpful for every cell regardless of the type and or location, including restoring hormone homeostasis and or modifying the patient's immune response.

In a prophetic example the inventors theorize the administration of a complete ULF treatment schedule creates clusters of cells that are self-assembling, constructive cells, rather than destructive cells, and further including stimulating the release of stem cells similar to a localized injury.

In a prophetic example, the inventors theorize within a complete ULF treatment schedule administering the narrow and specific 0.6180 Hz frequency directionally guides the cells to become their optimum expression, such that the cell will function better, be healthier and live longer, thus the ULF therapy not only creates new cells, but also produces healthier cells.

Furthermore, the prophetic example that the act of creation of a cell is a genetic change to the internal workings of the cell, which effectively defines it as a particular cell within the body. If that cell happens to be in the correct location and or cellular micro-environment, it will survive and propagate.

The current invention further encompasses replacing, optimizing and or improving genetic modification and enhancement systems such as but not limited to CRISPR, base editing, such as non-homologous end joining (NHEJ) and or homology directed repair (HDR), and or other prior art genetic modifications and splicing technologies such as but not limited to zinc finger nucleases (ZFNs) and transcription activator-like effector nucleases (TALENs).

The current invention eliminates the previously complex step that the radiation be characterized by operational parameters having respective values which are established relative to the natural frequency of the target tissue.

The current invention systemic frequency treatment schedule therapy eliminates the previously complex step wherein the target point is periodically repositioned on the image of the in vivo tissue.

The current invention systemic frequency treatment schedule therapy eliminates the previously complex step wherein the target tissue is moved in a pattern relative to the in vivo tissue in accordance with a selected protocol.

The current invention systemic frequency treatment schedule therapy eliminates the previously complex step wherein the base reference is a predefined phenotype for the in vivo tissue and the start place is a cellular structure of the in vivo tissue.

The current invention eliminates the need for the operational parameters to effectively dependent on operational judgments of the user.

The current invention eliminates the complex step of identifying specific tissue volume, dimensions, tissue type, abnormalities, etc. by administering the systemic narrow and specific 0.6180 Hz sine wave frequency treatment schedules.

The current invention overcomes and or eliminates much of the needed prior art steps for prior art stem cell therapies, including transplants and or highly complex culturing, such as growth chambers, petri dishes, complex differentiation and re-administration process(es), including a need for GMP (good manufacturing processes) and or ISO certification, and or a further need for complex differentiation steps, further including the amount of stem cells that are needed to be cultured and or re-administered (a single dose is about 85 to 88 million stem cells), which further requires complex differentiation and targeting.

The current invention further encompasses administering the ULF to stem cells at any point or step in the prior art methods and processes such as administering before, during and or after any stem cell therapy steps such as during extraction, culturing, genetic modification, re-administration, etc.

As an option progenitor cells may be inoculated and or grown in a cell culture in vitro (outside the body), and ULF treated using parameters disclosed herein, including ULF administration to produce ULF treated stem cells that have the potential to develop into any type of cell in the body. In contrast, adult stem cells generally develop into cell types related to the tissue from which the stem cells were isolated and or are specifically cultured to produce.

The current invention is separate and distinct from Grant et al. patents having significant operational differences from the above Grant et al. patents that significantly simplifies previously complex steps.

The current invention overcomes the prior art need to externally (in vitro) specifically culture MSCs so that they differentiate into the required tissue-specific stem cells by systemically ULF stimulating the patient's own MSCs and or tissue specific stem cells.

The inventors theorize that the apparatuses and methods of the current invention is suitable for therapeutic gain/repair and human enhancement for extension of mortality for every cell line in the human body.

The current invention provides previously unavailable efficacy and safety in the field of systemic human repair and or enhancement including stem cell therapies, in general encompassing apparatuses and methods for administering a complete treatment schedule encompassing a non-invasive and drug-free narrow and specific 0.6180 Hz frequency continuous sine wave therapy by employing a frequency generator, and or amplifier, and or a frequency emitter system that meets and or exceeds the parameters and criteria as described herein for systemic human enhancement from the human patient's own cells, including in-vivo and or in-vitro applications, provided in several prophetic exemplary embodiments. Some prophetic examples comprise frequency stimulation therapy for stem cell production and or release from the human patient's own cells, further encompassing enhancing the stem cell therapy, particularly at a tissue site having loss of function due to aging, condition, damage, and or disease, with a resultant increase in treatment safety by minimizing human interaction and or error, thus providing previously unavailable safety and efficacy in the field of enhanced stem cell therapy, in general. In some prophetic examples, the current invention encompasses a narrow and specific ultra-low frequency stimulation therapy that produces one or more of the enhanced production, release, viability, proliferation, migration and or engraftment of the human patient's own genetically compatible stem cells, and the complete ULF therapy enhances the stem cell's secretions thereby safely enhancing the secretions therapeutic effects during the administered stem cell therapy and simultaneously enhancing the patients preexisting cells.

In a prophetic example the complete ULF therapy of the current invention encompasses administering the narrow and specific frequency of 0.6180 Hz therapy to a human patient having physiological effects that may be referred to as biometrical training, including training the patient's biology to locally and or systemically entrain and or be physiologically coherent (biological oscillation systems) to the metrics of the emitted narrow and specific frequency of 0.6180 Hz (vibrating as the same), preferably maintaining an accurate continuous sine wave.

In a prophetic example the complete ULF therapy of the current invention encompasses administering the narrow and specific frequency of 0.6180 Hz therapy to a human patient will cause the patient's whole system to resonate (entrain) at the exposed sine wave frequency 0.6180 Hz, that is the basic holistic fundamental frequency that includes all aspects of a patient's entire system. The inventors theorize the 0.6180 Hz frequency is the underlying template frequency; and is what the inventor refers to as the electromagnotheric template.

ULF stimulation involves therapeutic administration of complete FST to a human patient at vastly lower power outputs (watts) than those used in high stimulation frequency generator applications, stimulating a wide variety of desirable biological (e.g., bio-stimulatory) effects. In a prophetic example, the current invention's complete ULF stimulation therapy encompasses locally and or systemically treating conditions, disorders, disease, pain, including headache and or muscle pain, and or inflammation, further including systemic enhancing the patient's healthy cells through ULF entrainment.

As disclosed herein, in a prophetic example, the complete ULF stimulation therapy of the current invention systemically alters one or more characteristics of the patient's cells, including their stem cells and or their stem cell secretions (either endogenous or delivered) that significantly improves systemic therapeutic effects in a wide variety of cellular and or organ therapies through ULF administration treatment schedules, reference FIG. 1 and FIG. 2. This is an object of the invention.

In several specified embodiments the current invention encompasses ULF augmentation and human patient enhancement therapy that, in a prophetic example, is effective due to the combination of frequency stimulation factors that stimulate stem cell enhancement and or stem cell secretions, further increasing the number of new cells and tissues that are formed, and or prevents the loss of the newly formed cells and or in a prophetic example stimulates the production and release of more than about 50 million stem cells, even into the billions of new stem cells, and further enhances responses from the human patient's live resident cells.

Based on a prophetic example disclosed herein and the recent advancement of medical knowledge, current research directions include efforts to elucidate, and employ stem cell action mechanisms for systemic and or localized human tissue and or organ repair including regeneration, such as but not limited to stem/progenitor cell trophic factor production, implications for cell and tissue repair regeneration and or repair and or augmentation, particularly for cancer therapies, immune modulation and development of novel strategies to use, in a prophetic example, frequency enhancing actions, such as for emergency and or regenerative therapies and or systemic human enhancement.

The current invention encompasses the development of a ULF treatment schedule for therapeutic cellular intervention(s) for autoimmune, inflammatory, and or malignant diseases, and or further encompasses systemic enhancement of tissue regeneration, and or enhances the stem cell cellular secretions from (MSCs), most preferably stimulated from the human patient's own cells.

The current invention discloses that ULF treated stem cells secrete potent combinations of trophic factors that modulate and adjust the molecular activity of the human patient's genetically matched biological environment, and provides a previously unavailable longer lasting time period between therapies, even decades in most instances.

In a prophetic example, several embodiments of the current invention encompass apparatuses and methods for the previously unavailable highly efficient stimulation of, in a prophetic example, billions, of genetically compatible stem cells are stimulated (produced) from the human patient's own cells and tissues.

In a prophetic example, several embodiments of the current invention encompass the administration of cells, and in some cases, fetal, umbilical cord, placenta-derived, adult, induced pluripotent, and or human embryonic stem cells and/or their partially or fully differentiated cellular derivatives and the like to treat a wide variety of damaged or diseased cells and tissues from replacement or regeneration. It is rapidly coming to the forefront of medical knowledge that stem cell technology is poised to treat many conditions and or diseases, in particular those that affect human patients who are non-responsive to conventional medical or pharmacologic therapies.

In a prophetic example, several embodiments of the current invention encompass administering a ULF treatment of the narrow and specific 0.6180 Hz sine wave frequency therapy to the human patient's own stem cells wherein said frequency stimulated stem cells are derived from the group of stem cell sources comprising adult stem cells, embryonic stem cells, placenta-derived stem cells, bone marrow-derived stem cells, mesenchymal stem cells, adipose stem cells, and or induced pluripotent stem cells, and the like.

In a prophetic example, several embodiments of the current invention encompass administration of the ULF administration of the narrow and specific 0.6180 Hz sine wave frequency therapy to donor stem cells wherein said frequency stimulated stem cells are derived from the group of stem cell sources comprising adult stem cells, embryonic stem cells, placenta-derived stem cells, bone marrow-derived stem cells, mesenchymal stem cells, adipose stem cells, and or induced pluripotent stem cells, and the like.

In a prophetic example, in several specified embodiments, the current invention encompasses that the apparatuses and methods of the current invention provides previously unavailable advantages for ULF therapy stimulation of large amounts of stem cells (in a prophetic example, potentially in the billions per exposure session) that are frequency stimulated to the patient's own cells, and further encompasses that the apparatuses and methods of the current invention's complete ULF therapy provides the systemic stimulation and or formatting (repairing and enhancing) frequency stimulated energy and signaling to produce and or release enhanced stem cells. This is an object of the invention.

In a prophetic example the current invention encompasses providing to a patient previously unavailable (undamaged) genetically compatible stem cells to obtain the highest percentage of potential therapeutic gain from frequency stimulating the individual human patient.

In a prophetic example the current invention's complete ULF exposure therapy stimulates the production of new stem cells, and or encourages the human patient's cells and tissues to become healthier, stronger and more functional, i.e. provides a previously unavailable systemic human biological enhancement.

In several prophetic examples further provide apparatuses and methods for human enhancement in a human patient further encompassing complete ULF stimulation therapy that, in a prophetic example, provides the production of the human patient's own stem cells, thus significantly improving, releasing, mobilizing, proliferating the systemic enhancement effects of stem cells and or their secretions. In one prophetic exemplary embodiment, the therapeutic effects of human cell therapies, such as but not limited to stem cell enhancement, including enhancing their secretions, are significantly improved. This is an object of the invention.

In a preferred embodiment, in a prophetic example, the current invention encompasses that administering a complete ULF treatment schedule creates in excess of 50 million new live stem cells in a human patient.

The inventors theorize a majority of the stem cells are released during the administration of the therapy, and the amount released in part depends upon what it is that requires repairing, as some conditions, injuries, and or diseases will not require as many stem cells as other conditions, injuries, and or diseases. Furthermore, the inventors theorize that there will be an attrition or a loss of stem cells at locations where the stem cells are not needed, including that administering the ULF treatment schedule produces an overage of stem cells for the condition needing correction, and having the remaining unused stem cells being reabsorbed back into the body once the ones that have made the correction have been utilized.

In a prophetic example administering the current invention ULF treatment schedule will be 20 times more efficient than all existing stem cell therapies with considerably less cost and associated risk, including immunological and genetic rejection, providing a safe, high speed ULF treatment schedule from initiation to completion.

In several specified embodiments, in a prophetic example the apparatuses and methods of the current invention encompasses eliminating the prior art's need for the complex steps of titrating (measuring) such as but not limited to biopsy, lab sampling, culturing, establishing a resonant frequency, and the like for tissue targeting and or organ targeting. This is an object of the invention.

In several specified prophetic examples, the current invention encompasses that the apparatuses and methods of a 0.6180 Hz continuous sine wave administration within a complete treatment schedule provides suppression and or complete remission of any known condition or disease, including diseases of an unknown etiology.

In several specified prophetic examples encompasses that the current invention encompasses apparatuses and methods providing systemic cellular repair and enhancement of the patient's entire biological system in a holistic manner, and that any part of the patient's system that is damaged, diseased, or 'deficient', is frequency targeted by the narrow and specific frequency of 0.6180 Hz in a continuous sine wave that recognizes and targets the deficiency, and restores it back into alignment by administering the current invention's treatment schedule encompassing systemically repairing and or enhancing the patient's healthy tissues and or stimulating an optimized biological environment whereby the unhealthy cells and tissues die off, and or are replaced by healthier cells and tissues by stimulating an enhanced cellular microenvironment to the human patient to enhance the patient's natural repair process and characteristics in a safer, faster, and more effective and efficient method than the prior art. This is an object of the invention.

In several specified prophetic examples encompasses that the apparatuses and methods of the current invention encompasses stimulating previously unavailable systemic frequency treatment schedules for enhancement of the human patient's own living, but dormant cells and tissues, for repairing and or enhancing damaged and or diseased cells and tissues that were damaged and remained in a dormant state, providing previously unavailable recovery and or enhancement including hours, days, months, years, or even decades after the initial injury, condition, and or disease has occurred.

In other specified prophetic examples, the complete ULF treatments schedules provide the equivalence of the positive effects of steroids, such as for improved muscle mass gain and or improved athletic performance, improved recovery rates, speed, flexibility, and or endurance including such as administering a complete ULF treatment schedule as an adjunct therapy with specific physical routines or procedures by one who is skilled in physical activity, further including influencing physiological, psychological, and or psychomotor controls.

In a prophetic example, the current invention further encompasses overcoming the limitations of prior art anabolic steroid use such as but not limited to oily skin and or hair, penis and or testicular shrinkage, insufficient hormone production, kidney and or liver conditions or failure, enlarged heart and or changes in blood pressure, which significantly increase in risk of heart attack and or stroke, and the like.

The current invention discloses apparatuses and methods for systemic prevention and or suppression and or complete remission of conditions, diseases and or disorders associated with dysregulation of cellular homeostasis, cell cycle regulation, interstitial fluid matrix dehydration/dysfunction, and the regulation of the balance between cell proliferation and apoptosis. The complete ULF therapy may be administered to a patient preferably with initial complete treatment schedule as a systemic enhancement therapy or as a preventive therapy or maintenance therapy with ULF dosages as needed. The method employs administering a frequency stimulating therapy that systemically restores the patient's electro-physiological homeostasis and cell function. This reduces and or eliminates the metabolic deficiency associated with aging and thereby optimizes and enhances the cell and tissue environment and electro-chemical cell replication environment.

In several exemplary prophetic examples encompasses that the patient's absorption of the ULF narrow and specific 0.6180 Hz frequency stimulation exposure therapy energy is frequency dependent and or watt (power) and or time distance dependent, and or encompasses maintaining a narrow and specific window of variance (accuracy) of 0.0001 Hz or more specific.

The efficiency of ULF stimulation therapy exposure dose(s) as a function of administered power may be calculated and adjusted as needed, for systemic and or localized administration of a complete ULF treatment schedule therapy of the narrow and specific 0.6180 Hz sine wave frequency generation and emission that is associated with stimulative activation of enhanced biological processes, while frequencies outside that window are excluded/shielded.

In particular, ULF mediated mitochondrial activation may be used as a marker of biostimulation effects and predicted outcomes.

In a prophetic example the complete ULF treatment schedule therapy of the current invention encompasses significant improvements and enhancements in the human patient's production of ATP (adenosine tri-phosphate) and or its ATP activity.

In a prophetic example if a biological repair and or enhanced effect is to occur, the ULF stimulus reaches the patient's tissues and cells. In this regard, a sine wave frequency of 0.6180 Hz is of the power range disclosed herein is essential to obtain sufficient penetration into the patient's entire body and further specifically frequency target desired cells and tissues.

In a prophetic example after administering this systemic frequency absorptive event (frequency exposure and or dosimetry) and promotion of stem cell to an excited state, one or more primary molecular processes from these highenergy states lead to a measurable biological effect in a patient at the cellular level, such as increased production and or activity of N. N-dimethyltryptamine and or ATP, and the like.

In a prophetic example, since a patient's frequency absorptive event needs to occur for a transfer of ULF stimulation energy to take place, the ULF transmitted stimulatory frequency meets the pre-defined parameters and criteria for power such as but not limited to exposure time, wave form, watts, voltage, amps, and or distance (inverse square), further including total exposure session's durations (dosing) of the ULF administration.

The current invention further encompasses that disease and or pain causing agents such as pathogens, bacteria, and viruses only exist within a very narrow and specific pH and ORP range, and that one of the most common factors of tissue injury is the presence of pain induced from acidosis induced hypoxia producing inflammation.

The inventors theorize that the diseases caused by viruses is a result of the patient's inability to assimilate the genetic information presented by the virus, and the current invention encompasses administering a ULF treatment to increase the ability of the human patient to maintain a healthy state and assimilate the genetic information as needed.

In certain prophetic examples encompasses the systemic and or targeted ULF administration of a complete treatment schedule to a human patient for the suppression and or complete remission of pain, including its signaling. Note pain and or its signaling is induced within a patient having a pH below 6.8.

In a prophetic example, administering an ultra-low frequency treatment schedule administering the narrow and specific 0.6180 Hz continuous sine wave frequency therapy to a patient is simultaneously or sequentially administered as an adjunct therapy combined with pH therapies, and further includes systemically obtaining an optimized and homeostatic pH.

In a prophetic example, the complete ULF therapy of the current invention reduces the 'biological age' of the human patient by increasing efficiency of how the biomechanical cellular activity is performed, and or stimulating the healthy cells to be more dominant, thereby accelerating cell and tissue repair, and or systemic repair.

In a prophetic example administering a complete ULF treatment schedule therapy stimulates a frequency based enhanced micro-environment, including enhanced cells, tissues, and the interstitial fluid matrix, that further optimizes the expressions and secretions of healthy cells, including pre-existing stem cells and further enhances their microenvironment, including the pericyte-MSC site, thus extending the time which the human patient continues to create new stem cells and simultaneously systemically enhances the patient's pre-existing healthy cells, tissues, and organs.

In a prophetic example the current invention encompasses that the efficacy and speed of the ULF therapy will vary by the distance from the emitter source (inverse square) and the patient's cell type in a density dependent manner, such that the softer/less dense the cell, the faster and more effective the therapeutic gain and or enhancing effect. As a prophetic example, ULF therapy will stimulate repair and enhancement of blood plasma quickly, ULF therapy will stimulate repair and enhancement of heart tissue at a medium rate, and ULF therapy will stimulate repair and enhancement of bone tissue at a much slower rate. Note as the cell type increases in density, there is increased insulation characteristics to the administered absorption of the ULF 0.6180 HZ sine wave.

In several prophetic examples the current invention encompasses obtaining human enhancement in a human patient further encompassing apparatuses and methods for improving and or enhancing the performances and or characteristics of stem cells, including their secretions, for enhancing the use in a wide variety of prior art stem cell therapies, by administering ultra-low frequency ULF as an adjunct with any stem cell therapies during any step or steps as needed. This is an object of the invention.

In a prophetic example ULF waves stimulate stem cells, wherein the ULF stimulation waves increase one or more of the production, release, viability, proliferation, differentiation, migration, and or frequency targeting stimulated from the human patients own cells, thereby enhancing the genetic compatibility of the stem cell therapies for use in a wide variety of injuries, conditions, and or diseases. In one prophetic example, the invention enhances the human patient's own genetic compatibility of neural stem cells for use in the human patient's own neural cell therapy, including but not limited to enhancement including their secretions for repairing of the patient's own brain tissue, spinal cord and or other central and peripheral nervous system cells and tissues.

In several prophetic examples encompasses apparatuses and methods for non-invasive and drug free FST for human enhancement by administering frequency stimulating therapies, further including complete FST treatment schedule therapy of the patient's dormant, but living, cells and tissues.

The current invention encompasses employing any suitable ultra-low frequency generator apparatus that is able to accurately generate the narrow and specific continuous sine wave frequency of 0.6180 Hz with a range of variance (accuracy) of 0.0001 Hz or more specific as disclosed herein during the ULF 15-minute exposure sessions (preferably within a complete a treatment schedule) provided via apparatuses and methods of the current invention.

In several embodiments, encompasses apparatus and method for enhancing the efficacy of stem cell therapy in an individual human patient complete ULF stimulation therapy is provided that eliminates the prior arts' need to identify the type of condition, disorder, or disease.

In an exemplary embodiment, the method comprises identifying a human patient who is suspect or diagnosed of having an organ or organs with impaired function, administering a complete ULF treatment schedule as disclosed herein from administering a complete ULF therapy delivery device having a frequency exposure emitting surface (wave guide) that accurately emits frequency exposure stimulation wave energy, and delivering the ULF exposure stimulation sine wave energy to the tissues, wherein the narrow and specific 0.6180 Hz frequency wave energy enhances one or more of the production, viability, engraftment, proliferation, migration, and or differentiation of the stimulated stem cells and or their enhanced secretions, thereby enhancing the efficacy of the individualized stem cell therapy to a human patient.

In several prophetic examples, the human patient's own stem cells are systemically and or locally produced by ULF stimulation therapy and or released from one of a variety of the human patient's stem cell producing sources such as but not limited to adult stem cells, bone marrow stem cells, mesenchymal stem cells, adipose stem cells, and or induced pluripotent stem cells, and the like.

Note in a prophetic example the inventors theorize any cell is a stem cell.

In a prophetic example the inventors theorize that over 98% of all cell types produce stem cells, note excluding certain types of cellular mutation(s).

The current invention administration of complete ULF treatment schedule encompasses regenerating the damaged cells and tissues in a patient, for example by directly repopulating the cells, tissues, organs by supporting the stem cell secretions proliferation of endogenous cells.

As an option or variation of the invention the frequency enhanced mesenchymal stem cells, and or their secretions, may be optionally administered, preferably as an adjunct therapy, with allogeneic transplants due to the ability of the stem cell's secretions to locally and or systemically modulate the patient's immune response at the damaged or diseased tissues. In a prophetic example, the FST treated stem cells alter T-cell and or antigen presenting cell function, thereby reducing immunologic rejection from many prior art stem cell therapies. In a prophetic example, the patient's stem cells additionally systemically reduce fibrosis and in the patients damaged or diseased tissues. This is an object of the invention.

In several exemplary embodiments, the ULF therapy power wave energy is administered to a human patient having an emitted power ranging between about 0.01 to 10 watts to enhance, restore, and or promote systemic cell survival, function, including both the systemic and targeted frequency exposure treatments in a human patient.

In several exemplary embodiments, the parameters of the ULF generator for administering the continuous sine wave is preferably selected to accurately deliver the narrow and specific 0.6180 Hz frequency in a manner which achieve results which are not obtainable in the prior art.

In some specified embodiments, the invention's ULF and FST wave energy is administered to a human patient's cells, tissues, and or organs in vitro (outside the body), while in some embodiments, the ULF and FST wave energy is optionally administered to the patient's cells in vivo (inside the body) (e.g., post dosage administration to a human patient).

In still other embodiments, a complete ULF stimulation therapy is administered to a patient in both in vitro (outside the body) and or in vivo (inside the body) applications, and further includes the possibility of in vitro processing of cells, including stem cells and or their the secreted factors, for collection and re-administering cells that are ULF stimulated in a culturing chamber, reference FIG. 1 and FIG. 2, as disclosed herein as an alternative to use of cultured and implanted live stem cells and further including having in vitro culture conditions which may enhance the in vivo (inside the body) production of those secretion factors upon re-administration into a human patient as needed to treat subsequent inflammation such as by secreting trophic factors such as bio-active (bio-stimulative) multi-functional secretions, further including defensins (makes the stem cell micro-environment anti-microbial and or anti-pathogenic). This is an object of the invention The inventors theorize that human progenitor cells, including neural progenitor cells, may be systemically frequency stimulated from the human patient's own cells and or induced to differentiate from the frequency stimulation exposure of 0.61803 Hz sine wave without the presence of specific growth factors that are normally required for differentiation within the prior art.

In a prophetic example the current invention's ULF administration treatment schedules of the current invention promote (MSC) proliferation, (MSC) secretome release, and or stimulates the propagation activity of the patient's own healthy cells both locally and systemically as needed from the inventive 0.6180 Hz frequency and or watt power dose-dependent therapy administration.

In certain embodiments described herein and related to FST apparatuses and methods for systemic human enhancement and enhancing stem cells and or their secretions in general, the functions and or therapeutic benefits are based in part on the prophetic example that administering a narrow and specific sine wave having a frequency of 0.6180 Hz FST energy administered systemically to tissues appears to be an important factor in determining the relative efficacy of frequency stimulation therapy, and particularly with respect to enhancing the function of neurons in both healthy and or diseased states and thus provides previously unavailable advantages for improved stem cell therapy and or FST for a wider variety of clinical applications as needed in the art.

Several embodiments described herein provide apparatuses and methods directed toward the repair and enhancement of neurologic function in a human patient. In several embodiments, the apparatuses and methods include administering a neurologic enhancing effective amount of the ULF energy requires a narrow and specific frequency of 0.6180 Hz preferably maintaining an accurate continuous sine wave form, and continuously maintaining the narrow and specific window of variance (accuracy) of 0.0001 Hz, and or producing an emitted power ranging between about 0.01 to 10 watts and a patient absorbed power of ranging between about 0.001 to 1 watts (note about 1/10th of emitted power is absorbed) to at least one area of the brain of a human patient. In certain embodiments, administering the neurologic function enhancing effective dose to the patient of ULF energy includes administering a predetermined wattage having a narrow and specific ULF exposure sessions of 0.6180 Hz doses and or complete treatment schedules as described herein are sufficient to cause significant repair and enhancement.

In some embodiments, to administer a repairing and enhancing amount or dose of the invention's ULF to the internal tissue to be treated using a suitable ULF emanating source preferably positioned outside the patient's body, and or further including a frequency sensor, a signal amplifier, and or frequency indicator, and or power sensor/monitor, reference FIG. 3.

Certain embodiments encompasses administering a complete ultra-low frequency treatment schedule emitting the narrow and specific 0.6180 Hz continuous sine wave frequency to a patient comprising:
administering frequency stimulation therapy via an accurate frequency emitting device to a patient in need of organ repair and or enhanced function, wherein a patient's entire body, including their organs, is subjected to frequency stimulating therapy, including stem cell therapy, further comprising donor cells, gene therapy and or systemic enhancement frequency therapy;
optionally sensing a physiologic parameter indicative of local organ including localized inflammation, and subsequently modifying the frequency stimulation therapy dosages based on the physiological parameters, or as needed.

The current invention encompasses in several specified embodiments administering a complete ULF treatment schedules for reducing and or eliminating (suppression and or complete remission) a variety of human conditions, disorders, pathogens, and or diseases including but not limited to Chronic Lung Disease, including Chronic lower respiratory disease and or Chronic obstructive pulmonary disease (COPD), influenza and or pneumonia, Chronic Traumatic Encephalopathy (C.T.E.), heart disease, stroke, Bubonic Plague, Smallpox, Herpes Simplex Virus (I and II), Yellow Fever, Tuberculosis, Measles, Cholera, Meningitis, SARS, Whooping Cough, Avian Flu, Influenza A-H1N1, Leprosy, Syphilis, Alzheimer's disease, Diabetes (Type I and Type II), apnea, Kidney disease, HIV and or AIDS, MS, viruses, arthritis, including rheumatoid arthritis and or osteoarthritis, mesothelioma, autoimmune hepatitis, hepatitis A, hepatitis B, hepatitis C, primary biliary cirrhosis, liver failure, amyotrophic lateral sclerosis, chronic fatigue syndrome, Lyme disease, fibromyalgia, and the like.

The current invention encompasses in several specified embodiments administering a complete ULF treatment schedules for prophylaxis treatment for a variety of human conditions, disorders, pathogens, and or diseases including but not limited to Chronic Lung Disease, including Chronic lower respiratory disease and or Chronic obstructive pulmonary disease (COPD), influenza and or pneumonia, Chronic Traumatic Encephalopathy (C.T.E.), heart disease, stroke, Bubonic Plague, Smallpox, Herpes Simplex Virus (I and II), Yellow Fever, Tuberculosis, Measles, Cholera, Meningitis. SARS, Whooping Cough, Avian Flu, Influenza A-H1N1, Leprosy, Syphilis, Alzheimer's disease, Diabetes (Type I and Type II), apnea, Kidney disease, HIV and or AIDS, MS, viruses, arthritis, including rheumatoid arthritis and or osteoarthritis, mesothelioma, autoimmune hepatitis, hepatitis A, hepatitis B, primary biliary cirrhosis, liver failure, amyotrophic lateral sclerosis, chronic fatigue syndrome, Lyme disease, fibromyalgia, and the like.

The current invention encompasses in several specified embodiments administering a complete ULF treatment schedule as an adjunct therapy before, during, and or after other therapies including but not limited to cancer therapies (chemotherapy, radiation, surgery), prophylactic therapies, Diabetes Therapy (Type I and Type II), cosmetic therapies, pH therapies, physical therapies, dental therapies, orthodontic therapies, acupuncture therapies, chiropractic therapies, osteopathic therapies, bracing therapies, skeletal therapies, such as casting therapies, heart disease therapies, neurological therapies, including C.T.E., Parkinson's Disease and Alzheimer's, further including enzyme therapies, hormone therapies, genetic therapies (including CRISPR), stem cell therapies, plastic surgery, and a wide variety of vitamins, herbs, nutraceutical, pharmaceuticals, pharmaceutical drugs, and or other therapies.

In a prophetic example, in some cases, the current invention 0.6180 Hz sine wave frequency therapy stimulates and enhances human stem cell activity and may be employed as a stand-alone or as an adjunct therapy administered prior to, and or in response to, a prior art therapy that itself induces damage to cells and tissues.

The current invention encompasses in several specified embodiments administering a complete ULF treatment schedule as an adjunct therapy that is compatible with a wide variety of nutraceuticals and or pharmaceutical drugs, including herbs, and or acupuncture therapies, chiropractic therapies, osteopathic therapies, further including other frequency based therapies.

The current invention encompasses in several specified embodiments employing a complete ULF treatment schedules for reducing and or eliminating (suppression and or complete remission) damage accumulated from environmental toxins, such as but not limited to smog, sulfide and or carbon emissions, plastics, pollution, and the like, further including augmenting environmental pollutions.

In a prophetic example the current invention encompasses systemically administering the complete narrow and specific 0.6180 Hz sine wave frequency treatment schedule to a patient to increase and or enhance the patient's vascular density.

In a prophetic example the current invention encompasses administering a complete ultra-low frequency treatment schedule stimulates the repair of, and function of, the patient's interstitial tissue to increase cellular waste excretion (disposal).

In a prophetic example the current invention encompasses administering a complete ultra-low frequency treatment schedule for repairing a patient's arthrodesis and systemically enhancing the biological system.

In a prophetic example the current invention encompasses administering a complete ultra-low frequency treatment schedule to a patient for repairing a patient's congenital pseudo-arthrosis and systemically enhancing the biological system.

In a prophetic example the current invention encompasses administering a complete ultra-low frequency treatment schedule to a patient for repairing a patient's urinary incontinence and or muscle stimulation and systemically enhancing the biological system.

In a prophetic example the current invention encompasses administering a complete ultra-low frequency treatment schedule therapy to a patient for repairing a patient's cervical fusion including in patients at high-risk of non-fusion and systemically enhancing the biological system.

In a prophetic example the current invention encompasses administering a complete ultra-low frequency treatment schedule therapy for treatment of depression and or anxiety and systemically enhancing the patient's biological system.

In a prophetic example the current invention encompasses administering a complete ultra-low frequency treatment schedule therapy for treatment of migraines and systemically enhancing the patient's biological system.

In a prophetic example the current invention encompasses administering a complete ultra-low frequency treatment schedule therapy for treatment of brain cancers and systemically enhancing the patient's biological system.

In a prophetic example the current invention encompasses administering a complete ultra-low frequency treatment schedule therapy to a patient for vaginal rejuvenation and systemically enhancing the patient's biological system further including repairing vaginitis.

In a prophetic example the current invention encompasses administering a complete ultra-low frequency treatment schedule therapy to a patient for osteoarthritis and systemically enhancing the patient's biological system.

In a prophetic example the current invention encompasses administering a complete ultra-low frequency treatment schedule therapy to a patient for relief of pain in acute sprains and or whiplash injuries and systemically enhancing the patient's biological system.

In a prophetic example the current invention encompasses administering a complete ultra-low frequency treatment schedule therapy to a patient for suppression and or elimination of pain and or pain medication use and or as an adjunct with pain medication, and systemically enhancing the patient's biological system.

In a prophetic example the current invention encompasses administering a complete ultra-low frequency treatment schedule therapy to a patient for reducing the need for narcotic pain medications and or their side effects of sedation, nausea, and or vomiting and systemically enhancing the patient's biological system.

In a prophetic example the current invention encompasses administering a complete ultra-low frequency treatment schedule therapy to a patient for sustained, drug-free pain relief therapy and systemically enhancing the patient's biological system.

In a prophetic example the current invention encompasses administering a complete ultra-low frequency treatment schedule therapy for postoperative pain to be reduced in the patients as well as improved arm mobility and or strength and systemically enhancing the patient's biological system.

In a prophetic example the current invention encompasses administering a complete ultra-low frequency treatment schedule therapy to a patient for increasing circulation and systemically enhancing the patient's biological system.

In a prophetic example the current invention encompasses administering a complete ultra-low frequency treatment schedule therapy to a patient for reducing inflammation and or stimulating the transport of nutrients through the patient's cellular structure and systemically enhancing the patient's biological system.

In a prophetic example the current invention encompasses administering a complete ultra-low frequency treatment schedule therapy to a patient for treating Tremor-Dominant Parkinson's Disease and systemically enhancing the patient's biological system.

In a prophetic example the current invention encompasses administering a complete ultra-low frequency treatment schedule therapy to a patient for treatment of fractures and or spinal fusion and systemically enhancing the patient's biological system.

In a prophetic example the current invention encompasses administering a complete ultra-low frequency treatment schedule therapy to a patient for improvement of skin blood flow and systemically enhancing the patient's biological system.

In a prophetic example the current invention encompasses administering a complete ultra-low frequency treatment schedule therapy to a patient for healing of venous stasis ulcers and systemically enhancing the patient's biological system.

In a prophetic example the current invention encompasses administering a complete ultra-low frequency treatment schedule therapy to a patient for reduction of post mastectomy lymphedema and systemically enhancing the patient's biological system.

In a prophetic example the current invention encompasses administering a complete ultra-low frequency treatment schedule therapy to a patient for breast augmentation and systemically enhancing the patient's biological system.

In a prophetic example the current invention encompasses administering a complete ultra-low frequency treatment schedule therapy to a patient for administering in addition to standard of care to reduce post-operative discomfort and or morbidity after lumpectomy, SLND, and or lumpectomy and systemically enhancing the patient's biological system.

The current invention encompasses in several specified embodiments employing a complete ULF treatment schedules for increasing flexibility, including fascial and interstitial matrix flexibility, further reducing pains and aches.

The current invention encompasses in several prophetic examples employing the invention's a complete ULF treatment schedule as disclosed herein is administered for a variety of orthopedic treatment therapies such as but not limited to cartilage repair, tendon repair, arthroscopy enhancement, bone repair and enhancement such as for non-union/non-fusion, stimulating and or repairing bone fusion and growth, joint fusion, spinal fusion, and the like, and further may optionally be administered as an adjunct therapy with other conventional therapies including bracing system(s).

The apparatus and method of the current invention encompasses frequency treating a human patient having one or more fractured and or broken bones.

In a prophetic example encompasses tensioning cast methods and apparatuses such as casts and or adjustable tensioning casts (casts having pins) encompassing the patient's arm for administering a complete ULF 0.6180 Hz sine wave therapy having an embedded ULF emitter apparatus and system.

In a prophetic example encompasses tensioning cast methods and apparatuses such as casts and or optional fixation systems (casts having pins) encompassing the patient's leg and foot for administering a complete ULF 0.6180 Hz sine wave therapy having an embedded ULF emitter apparatus and system.

The current invention encompasses in several prophetic examples employing the invention's a complete ULF treatment schedule as disclosed herein is administered for a variety skeletal conditions and their repair and enhancement such as administering for broken bone(s) to significantly reduce pain and the time of recovery to about ⅓ of the time, such as instead of the conventional six-week standard, the bone would heal in about two weeks, preferably employing a variety of tensioning brace(s) before, during, and or after the treatment schedule administration.

In a prophetic example the inventors theorize that administering a complete ULF treatment schedule increases the skeletal cells' malleability, so that it can be restructured, enhanced, and or aligned and lengthened, and or reformed preferably administered in conjunction with a variety of bracing/tensioning system(s) as known in the art.

In a prophetic example the current invention encompasses a ULF sine wave frequency generating apparatus, a frequency amplifier, an accurate frequency emitter system, reference FIG. 3, to systemically repair and enhance genetic damage occurring independently within trillions of the patient's cells, including eliminating and repairing the accumulation of genetic damage within cells of the human patient. Note the average human has about 400 genetic defects.

In some embodiments, there is provided an apparatus and method for providing suppression and or complete remission of damage or disease in the central nervous system in a patient, comprising administering an effective dosage of the invention's complete ULF sine wave frequency treatment schedule to stimulate progenitor cells in in vivo and or in vitro applications.

In certain embodiments, apparatuses and methods are encompasses for therapeutically suppressing and or completing eliminating damage and or illness in the central nervous system in a human, comprising administering an effective treatment schedule (dose) of ULF therapy to an in vitro culture comprising progenitor cells (e.g. stem cells, induced pluripotent cells, optionally including genetically modified adult cells).

In certain prophetic examples, ULF treatment schedule therapy of a patient comprises systemic and or frequency targeting of a human patient, wherein administering an effective dose of frequency stimulation energy includes administering sufficient FST to a patient administering sine wave form having a narrow and specific frequency range of 0.6180 Hz continuously maintaining a narrow and specific window variance (accuracy) of 0.0001 Hz, and a watt power of at least about 0.01 watts delivered to and absorbed by the cells, tissues, including the progenitor cells of the central nervous system ("CNS") of the human patient, further including the myelinated sheath of the nerves. Following a complete ULF therapy, the progenitor cells differentiate to form one or more cell types of the central nervous system. The invention's enhanced stem cell therapy may serve any of a wide variety of purposes, including replacement of cells and tissues that have been irreparably damaged, repair of a portion of the CNS, enhance the production of important CNS neurochemicals such as dopamine, serotonin, endogenous opioid peptides, and the like.

In certain prophetic examples, the current invention encompasses administering a complete ULF treatment schedule therapy to a patient for systemic and or localized treatment of a patient's autonomic nervous system (ANS), Sympathetic nervous system, and or enteric nervous system (relating to the intestines), and the like.

The inventors theorize that 0.6180 ratio corresponds to the preferred sympathetic to parasympathetic activity ratio in the human patient.

In certain prophetic examples, ULF treatment schedule therapy of a patient comprises systemic and or frequency targeting of a human patient's myelinated sheath and or systemic administration to the patient's entire nervous system.

Embodiments including those associated with senescence, including Alzheimer's further including diseases and or tissues associated with inflammation and or the immune response, such as macrophages, bone marrow, lung (asthma), small intestine (Crohn's disease) and or skin (erythema nodosum), and the like. In a prophetic examples of cell repair and enhancement is promoted by the invention's frequency therapy including, but are not limited to, fibroblasts, coronary endothelial cells, neuronal precursors, cardiac smooth muscle cells and promonocyte cell lines. Further examples of age-related diseases include, but are not limited to, cardiovascular disease, diabetes mellitus, neurological disorders, bone spurs, gallstones, indigestion, high blood pressure, arthritis, bursitis, rheumatism, gout, muscle cramps, high cholesterol, insomnia, Fibromyalgia, chronic fatigue syndrome, headaches, osteoporosis, Pick's disease, myotonic dystrophy, Huntington's disease, Parkinson's disease, adult onset leukodystrophy, arteriolosclerosis, autoimmune diseases, multiple sclerosis, amyotrophic lateral sclerosis, heat stroke, epilepsy, Alzheimer's disease, Parkinson's disease, Huntington's disease, dopaminergic impairment, dementia resulting from other causes such as AIDS, cerebral ischemia including focal cerebral ischemia, and physical trauma such as a compression injury in the CNS, including concussion and C.T.E., an impact injury of the brain, spinal cord, nerves and or retina, including severed nerves, and or any other acute injury or insult producing neurodegeneration and same.

In a prophetic example, many other diseases that affect various tissues and organs are significantly improved from administering the invention's complete ULF stimulation treatment schedule. In several prophetic examples, liver damage and or cancer(s) is treated with the current invention's sine wave frequency stimulation therapy in order to augment, enhance and replace damaged lost or malfunctioning cells to obtain full remission in a human patient.

The current invention encompasses that the ULF administration distance, dosing, time, watts, and ULF sine wave form stimulation energy density as administered to the human patient results in a preferred total ULF dosimetry (absorption) by the human patient, which may include an area of the brain affected by neurodegenerative disease (e.g., C.T.E., Parkinson's disease), that appears to be a significant factor in simultaneously administering complete ULF therapy and stem cell therapy to treat the patient's brain.

In several prophetic examples, stem cells are frequency stimulated and or mobilized, from administration of a complete FST treatment schedule to provide systemic prophylaxis, suppression and or complete remission of other conditions, disorders and or diseases not stated nor disclosed herein.

For example, in some prophetic examples, FST mobilizes the patient's stem cells are differentiated to a pancreatic lineage and administered to recapitulate insulin secretion in a human diabetic patient. In one prophetic example, a complete FST treatment schedule is used to stimulate and enhance in a human patient the systemic production and or mobilizing of stem cells, while in one prophetic example, ULF is administered in the stem cell therapy itself. In still another prophetic example the ULF is administered both in the production and mobilization and in the stem cell therapy aspects of a complete treatment schedule(s). This is an object of the invention.

In several prophetic examples, the current invention encompasses administering a non-invasive complete ULF treatment schedule to diabetic human patients (Type I and Type II) to systemically stimulate the patient's cells and tissues, including the human patient's own stem cells (autologous) and or their secretions (or optionally other stem cells differentiated to pancreatic identity), in order to recapitulate loss of insulin secretion, and further to repair genetic damage associated with diabetes (Type I and Type II), and further includes repairing diabetic damage, and further including reducing and or eliminating the need for insulin therapy. This is an object of the invention.

In several prophetic examples, an apparatus and method is disclosed for increasing the number of one or more particular cell types from the human patient's own (autologous) genetically repaired and or enhanced cells tissues and organs, such as harvested, enhanced and or re-administered in to the human patient's bloodstream is disclosed. This is an object of the invention.

The cell types may include, for example, white blood cells (e.g., a neutrophil, macrophage, natural killer cell, basophil, eosinophil. B cell, CD4 T-cell, or CD8 T-cell) platelets, and or red blood cells. In some prophetic examples, a repair and enhancement of cells, such as stem cells (e.g., HSC) are frequency stimulated and or produced from the human patient's own (autologous) cells, stimulated by administering a complete FST treatment schedule systemically and or locally, either in vivo and or in vitro. The optional agent(s) could be given through any desired route of administration, including orally, rectally, vaginally, intravenously, intramuscularly, subcutaneously, topical patch, and or an aerosol. Some optional non-limiting examples of agents that may contribute to stimulating production and or systemic mobilization into the bloodstream of a patient and or improve function of a cell type may include growth hormones, erythropoietin, thrombopoietin, and the like. In addition to naturally occurring growth factors, growth factor analogs and growth factor derivatives such as fusion proteins and the like may be optionally administered as well.

In several prophetic examples encompasses that the apparatuses and methods of the current invention's complete ULF treatment schedules are compatible with a wide variety of enzyme therapies.

In several prophetic examples encompasses that the apparatuses and methods of the current invention's complete ULF treatment schedules may reduce, replace, and or eliminate the need for conventional hormone therapy, and may further be administered as an adjunct therapy with conventional hormone therapy.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular.

Definition of Terms

The term 'longevity' as used herein means duration of a particular life beyond the norm for the species. Synonym with macrobiosis—long life; great duration of life.

The term 'Dosimetry' as used herein refers to the measurement, calculations and or assessment of the ULF dose administration that is absorbed by the human patient.

The term 'fibrosis' as used herein is the thickening and or scarring of connective tissue, usually as a result of injury, disease, or surgery. When fibrosis occurs in response to injury, the term "scarring" is used, and or further may refer to an abnormal condition in which fibrous connective tissue spreads over/replaces smooth muscle and or other normal organ tissue.

The term 'repair' or 'repairing' as used herein in its broadest sense refers to returning to a state of health and or ameliorating a specific disease, disorder of structure (Note the average human has about 400 genetic defects), and or function in a human, especially one that produces specific signs or symptoms and or that affects a specific location that may or may not be a direct result of physical injury.

The term 'enhancement' or 'enhance' as used herein in its broadest sense means to temporarily or permanently make greater, optimize, increase and or improve in performance quality, value, and or extent any human biological system, to enhance human characteristics, processes, and or capacities beyond the state of being free from illness, injury or disease, and or further including 'enhancing' beyond the existing human range, such as but not limiting to 'enhancing' genetics, DNA activation, genetic template repair, stem cell production and or performance, functional capacity, further including significant psychological and or physiological benefits, trophic factor (secretion) optimization, optimizing the cellular microenvironment, increased disease resistance, increased intelligence, optimized physiological alignment, immuno-enhancement, neuro-enhancement, Nano-enhancement, and or the like.

The term 'biometrical training' or 'biometric training' as used herein in means training the biology to locally and or systemically entrain, and or be physiologically coherent (biological oscillation systems) to the metrics of the emitted narrow and specific 0.6180 Hz sine wave frequency (vibrating as the same).

The term 'secretions' or 'secretome' as used herein means trophic factors such as bio-active (bio-stimulative) secretions generated by stem cells that are multifunctional, and directed towards the combination of: angiogenesis; immune modulation; and or protection from apoptosis, such as but not limited to immune cells transient paracrine actions and or stem cell-secretion factors to modulate inflammation, acidosis (reduced pH) and or hypoxia, and or modulating immune cells for repair and enhancement of tissue and or organ homeostasis, and the like, further including defensins (makes the stem cell micro-environment anti-microbial and or anti-pathogenic).

As used herein, the term "option, optional or optionally" For the purposes of this specification it will clearly be understood that the word(s) "option" "optional" or "optionally" mean the subsequently described event of circumstances may or may not occur, and that the description includes instances where said event or circumstance occurs and instances which it does not.

As used herein, the term "viability" shall be given its conventional meaning and shall also refer to the ability of a cell, be it a stem cell or a resident cell, to survive trauma, disease, or other injury that would compromise the normal functionality of the cell.

The term viability as used herein is also assessed by function, wherein an increase in function may be associated with an increase in viability.

As used herein, the term "proliferation" shall be given its conventional meaning and shall refer to the process by which one or more stem cells (endogenous and or exogenous) divide and increase the population of cells, including stem cells (e.g., mitotic division).

The term "differentiation" as used herein refers to its conventional meaning, including but not limited to the method whereby an unspecialized, pluripotent stem cell proceeds through one or more intermediate stage cellular divisions, ultimately producing one or more specialized cell types. Differentiation thus includes the process whereby precursor cells, e.g., uncommitted cell types that precede the fully differentiated forms but may or may not be true stem cells, proceed through intermediate stage cell divisions to ultimately stimulate and or produce specialized cell types.

Differentiation encompasses the process whereby mesenchymal stem cells (MSC) are stimulated to differentiate into one or more of the committed cell types in vivo and or in vitro.

The term "ultra low frequency" as used herein is 0.6180 Hz is the optimum continuous sine wave frequency having a 0.001 Hz range of variance.

The term "frequency stimulation therapy" as used herein is 0.6180 Hz is the optimum continuous sine wave frequency having a 0.001 Hz range of variance.

The terms "treatment chamber" as used herein is used having conventional meaning to referring to the area where the 0.6180 Hz frequency is emitted within and includes treatment rooms, treatment pods, immersion tanks, hyperbaric chambers, vibrating tables, frequency containment shell apparatus, and or any desktop ULF treatment chamber or vessel suitable for processing and or culturing cells, tissues, portions and or complete organs, further including, but not limited to, petri-dishes, culture plates (single or multiple well), test tubes, bioreactors, incubators, having a variety of scales and or sizes depending upon application and the like. In one embodiment, a treatment chamber forms an enclosure which may be a complete enclosure around a person for treatment. A treatment chamber may be a partial enclosure around a person or around a portion of a person to be treated, such as a sleeve or cast. A treatment chamber may be a partial enclosure around a biological specimen.

Frequency and vibration, as used herein, are used interchangeably.

The term "hyperbaric chamber" as used herein refers to a pressurized sealed chamber to systemically increase the amount of oxygen in a patient, and is also commonly referred to as an altitude chamber, compression chamber, diving chamber, hypobaric chamber, decompression chamber, recompression chamber, and the like.

The term "migration" as used herein shall be given its conventional meaning and shall also refer to the movement of a stem cell (either endogenous and or exogenous) from its initial site (e.g., an endogenous storage and or administration) to a second site (e.g., a final position in a tissues). Migration occurs based on effects of frequency, fluid, flow, and or pressure changes in the electro-physical and or electrochemical environment to induce migration of cells.

Various embodiments have been described herein. Although this current invention has been described with reference to these specific embodiments, the descriptions are intended to be illustrative of the invention and are not intended to be limiting. Various modifications and applications may occur to those skilled in the art without departing from the true spirit and scope of the invention. Principal features and advantages of the invention will become apparent to those skilled in the art upon reviewing the following figures.

BRIEF DESCRIPTION OF THE FIGURES

The principal features and advantages of the current invention will become more apparent to those skilled in the art upon review of the following drawings.

The current invention encompasses in vitro repair and enhancement from administering a complete ULF treatment schedule of the current invention before, during, and or after any of these above disclosed prior art stem cell extractions, processing, modifications and or implantation steps.

FIG. 4 illustrates one of many possible configurations of a pre-programmable frequency generating apparatus 41 for generating and or displaying/indicating the ULF parameters, such as power (watts), selected wave form, emitted frequency, exposure time, via a display screen 42, further depicting adjustment controls 43, and or output terminals 44 to amplifier system, further including a power cord 45, and or frequency emitter depending upon application for accurately generating the emitted 0.6180 Hz continuous sine wave frequency having a narrow and specific window of frequency variance as needed, preferably within 0.0001 Hz or more specific, administered during the 15 minute exposure sessions (complete treatment schedules) preferably having a resting and testing period (pause time) of about 3 to 4 hours between each exposure session for ULF repair and or enhancement therapies, and or further encompasses a safety mechanism (apparatus) to identify the authorized operator(s) or practitioner(s) such as scanning a finger, thumb, and or whole palm and or hand, and or other suitable safety encoding mechanisms 46, and the like.

Figure 5:
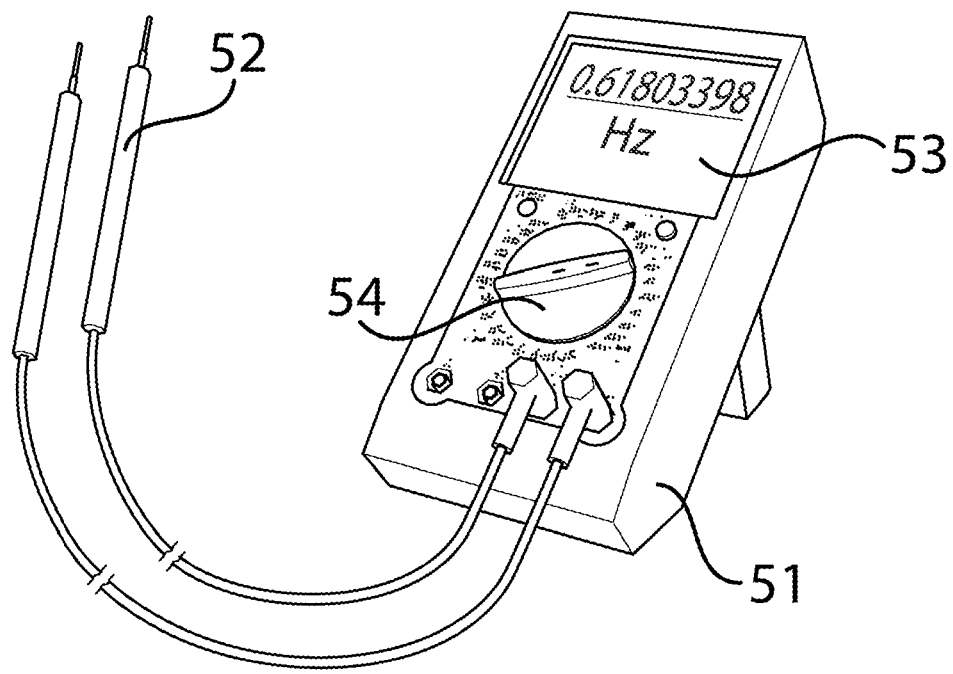

FIG. 5 illustrates one of many possible configurations for a transportable frequency and or watt indicating and or monitoring apparatus 51 depicting connection cords 52, indicating display screens for indicating the frequency and or power (watts) and or administered wave form 53 (note Sine wave is most preferred), and or selection dial(s) 54, further including indicating and or monitoring the time and or dose of the ULF administration.

Figure 6:
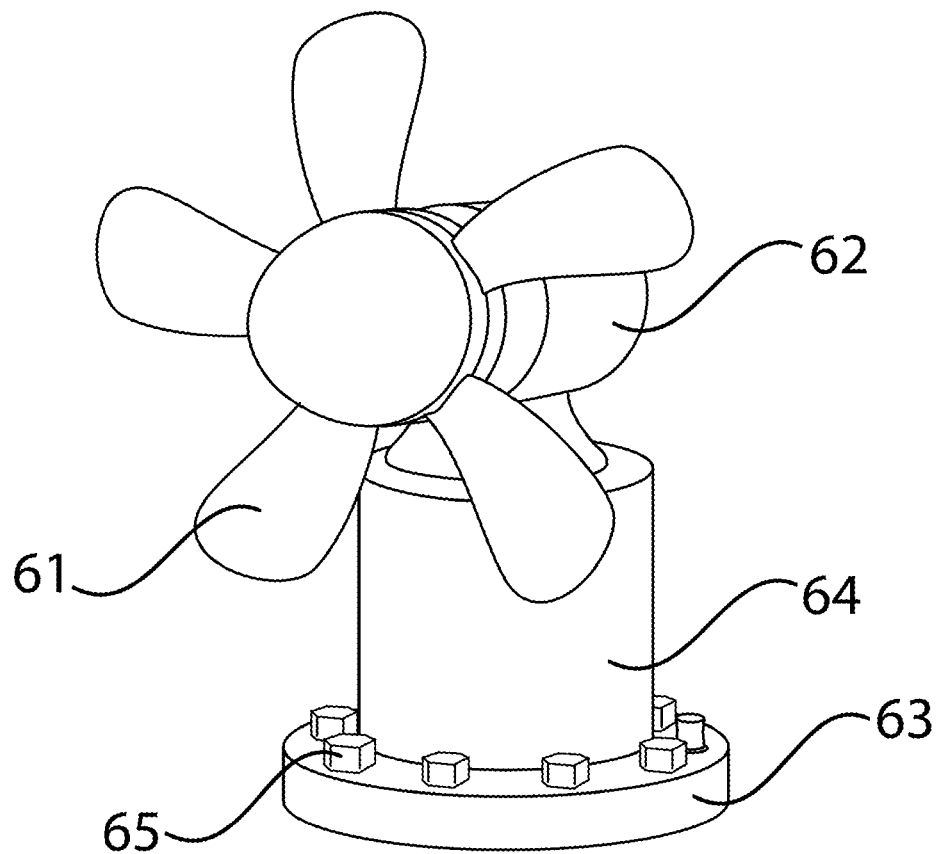

FIG. 6 illustrates one of many possible configurations of the ULF generator driver/emitter apparatus encompassed by the current invention depicting a programmable rotary driver system having an adjustable RPM (speed), number of adjustable props (blades) 61, an adjustable prop pitches (angle) for an adjustable high SPL (sound pressure level) the ULF emission preferably employing an optional frequency regulating adjustable input and or output baffling system (not shown), having an electromotor 62, a frequency dampening and or stabilizing platform 63, a vibration dampening and or stabilizing shaft 64, a stabilizing bolt 65, to accurately emit the narrow and specific 0.6180 Hz frequency, preferably generating an accurate continuous sine wave producing an emitted power ranging between about 2 to 10 watts and or a patient absorbed power of ranging between about 0.2 to 1 watts (note about 1/10th of emitted power is absorbed by the patient), and having a narrow and specific window of frequency variance (accuracy) within 0.0001 Hz or more specific during the patient's preferred 15 minute exposure sessions (preferably within a complete treatment schedule) preferably having a resting and testing period (pause time) of about 3 to 5 hours between exposure sessions for systemic ULF repair and enhancement therapy as needed or desired.

Additionally, while FIG. 6 depicts a rotary driver apparatus system, the current invention further encompasses other ULF emitter systems such as but not limited to Piezoelectric Cantilever Beams, Ultra Low Frequency Vibration Tables, Ultra Low Frequency Vibration generators, Ultra Low Frequency Pulse Generators, Ultra Low Frequency Pulse Resonators, Electrostatic Loud Speaker (ESL) Panels, Ac2ated Sound®, Electromagnetic Driver systems. Acoustic Surface Technologies, Antenna s, Ultra-low Frequency transducers, further including immersible underwater transducers, flextensional transducers, hydroacoustic, electromagnetic, and or active material-based, and the like, Ultra Low Frequency Drivers, pencil driver systems, leaf springs, and the like, whereas they meet the current inventions pre-defined performance parameters and or criteria disclosed herein for accurately emitting a sine wave producing an emitted power ranging between about 2 to 10 watts and a patient absorbed power of ranging between about 0.2 to 1 watts (note about 1/10th of emitted power is absorbed), preferably having a narrow and specific window of frequency variance (accuracy) within 0.0001 Hz or more specific as needed during the 15 minute exposure sessions within a complete treatment schedule preferably having a resting and testing period (pause time) of about 3 to 5 hours between exposure sessions for systemic ULF repair and enhancement therapy as needed or desired.

The current invention further encompasses modifying any ULF emitter system(s) to meet the disclosed parameters and or criteria disclosed herein.

Figure 7:
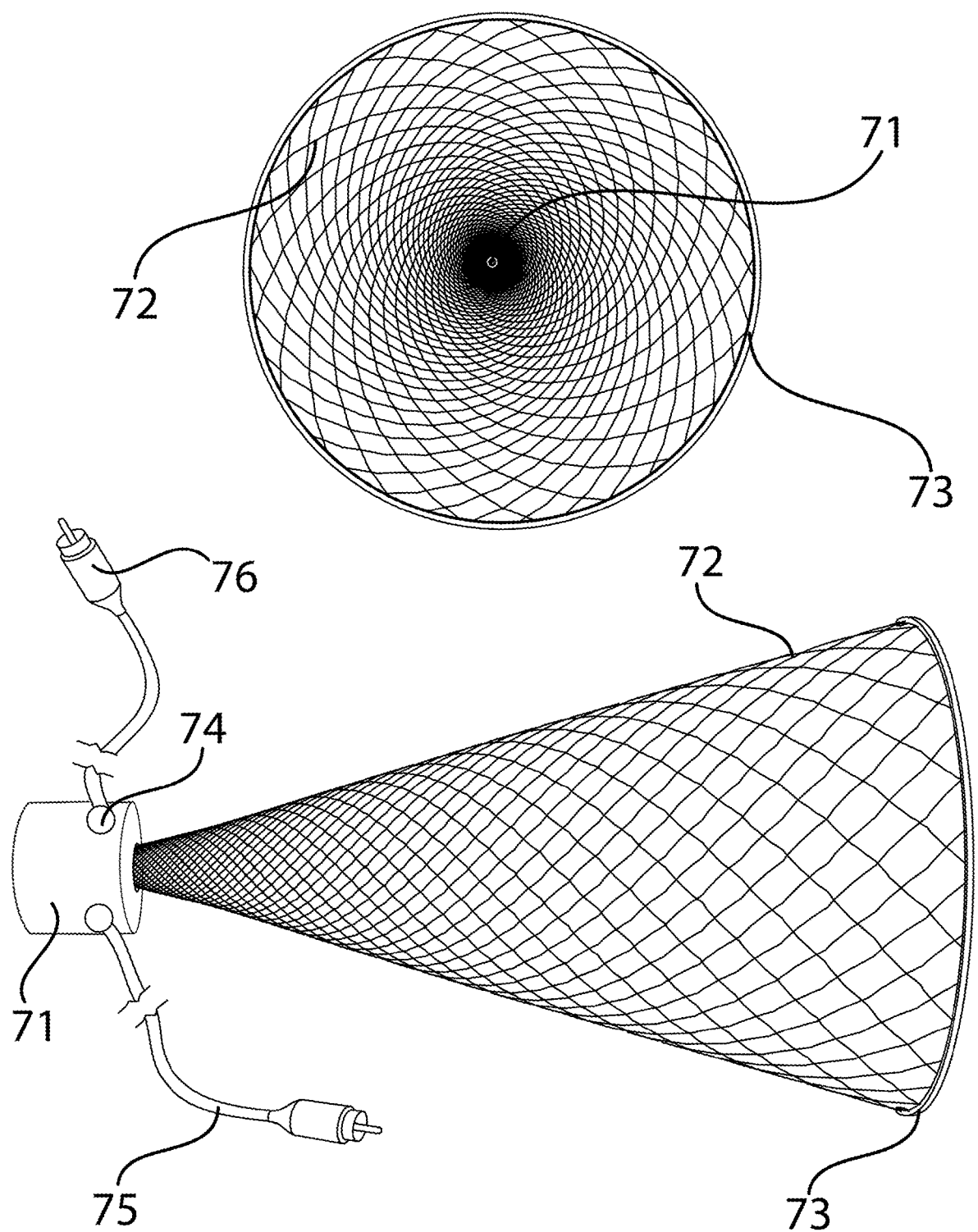

FIG. 7 depicts an end view and cross section view of a preferred ULF antenna emitting apparatus for the administration of the narrow and specific 0.6180 Hz sine wave frequency having an emitted power of about 2 to 10 watts, preferably producing and maintaining an accurate continuous sine wave producing the narrow and specific window of frequency variance (accuracy) within 0.0001 Hz or more specific administered during the 15 minute exposure sessions preferably within a complete treatment schedule for ULF systemic repair and enhancement therapy as needed or desired in both immersion and or open air ULF applications of the current invention that is simplified for illustrative purposes. Note the antenna housing and or support system is not shown for illustrative purposes. The preferred length of the antenna system, down the C-axis from emitter source base to tip, is preferably between about 11.8 inches and 3 feet. The preferred angle of the antenna cone apex is 33 degrees providing a conical wave guide transmitter having wire/mesh transmitting materials made from wire and or mesh materials such as silver, copper, gold, and or their alloys, or other suitable electro-conductive wire mesh and or net materials configured into an expanding diamond shape.

Reference character 71 depicts a sine wave frequency emitting source. Reference character 72 depicts the antenna's transmitting materials made from wire and or mesh materials such as silver, copper, gold, and or their alloys, or other suitable electro-conductive wire mesh and or net materials. Reference character 73 depicts the edge/tip of the antenna. Reference character 74 depicts the cable attachment point to the sine wave frequency emitting source. Reference character 75 depicts the antenna cable between the antenna and the frequency generating source and or amplifier system. Reference character 76 depicts a cable terminal attachment apparatus to be connected to the frequency generating source and or amplifier.

Figure 8:
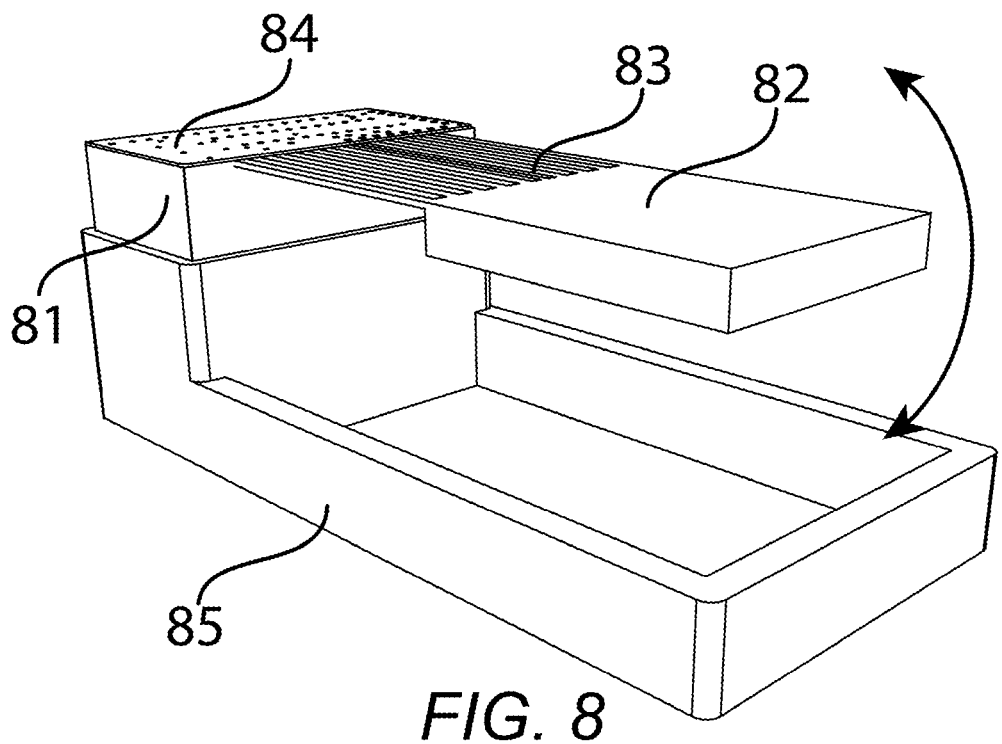

FIG. 8 in a illustrative embodiment depicts one of many possible configurations of a cantilever configured ULF generating apparatus and system that may be modified as needed to be suitable for the current invention requirements or as needed depicting one of many possible Piezoelectric configured Cantilever Beam ULF emitter systems having components such as but not limited to clamping setup 81, proof mass 82, vibrating beam 83, stopper (not shown), piezoelectric elements 84, supporting frame and spacer 85, and supporting spacer, and the like for accurately administering to a patient the narrow and specific 0.6180 Hz sine wave frequency preferably producing and maintaining an accurate sine wave administering to a patient an emitted power ranging between about 0.01 to 10 watts, and preferably having a narrow and specific window of frequency variance (accuracy) within 0.0001 Hz or more specific as needed during the 15 minute exposure sessions preferably within a complete treatment schedule for ULF human systemic repair and enhancement therapy as needed or desired.

Figure 9:
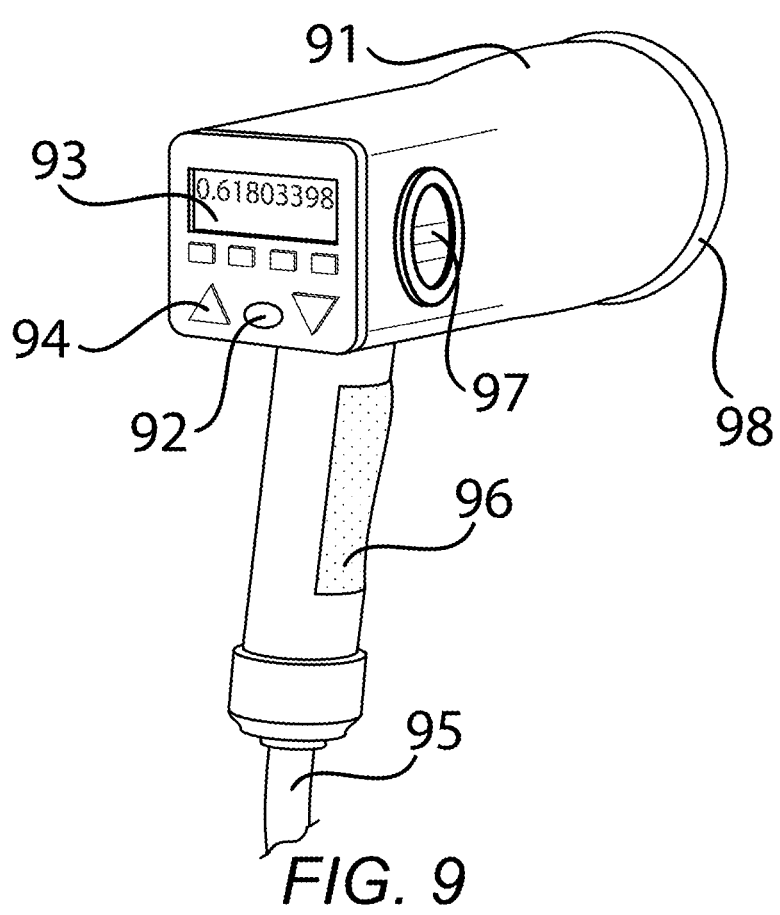

FIG. 9 in a illustrative embodiment depicts one of many possible configurations of the programmable transportable hand held frequency wave guide emitting pistol 91 of the current invention that is simplified for illustrative purposes that encompasses an on/off switch 92, frequency indicating display 93, illustrates some of many possible adjustment controls 94, power source 95, handle 96 and further including optional safety mechanisms (apparatus) that identifies the authorized operator(s) and or practitioner(s) by scanning a thumb, finger, and or hand (palm), and or other suitable safety encoding mechanism 97, for controlling dosage and administering the narrow and specific 0.6180 Hz sine wave frequency from one of many possible frequency emitting systems 108 producing a narrow and specific window of frequency variance (accuracy) within 0.0001 Hz administered during a complete ULF treatment schedule emitting an administered power ranging between about 0.01 watts and 2 watts, including a 15 minute emergency treatment exposure session, preferably having a resting and testing period (pause time) of about 3 to 5 hours between exposure sessions, for repair and enhancement therapy, to controllably expose at least one predetermined area of a human pateint's body to the ULF stimulation therapy for targeted emergency treatment.

Figure 10:
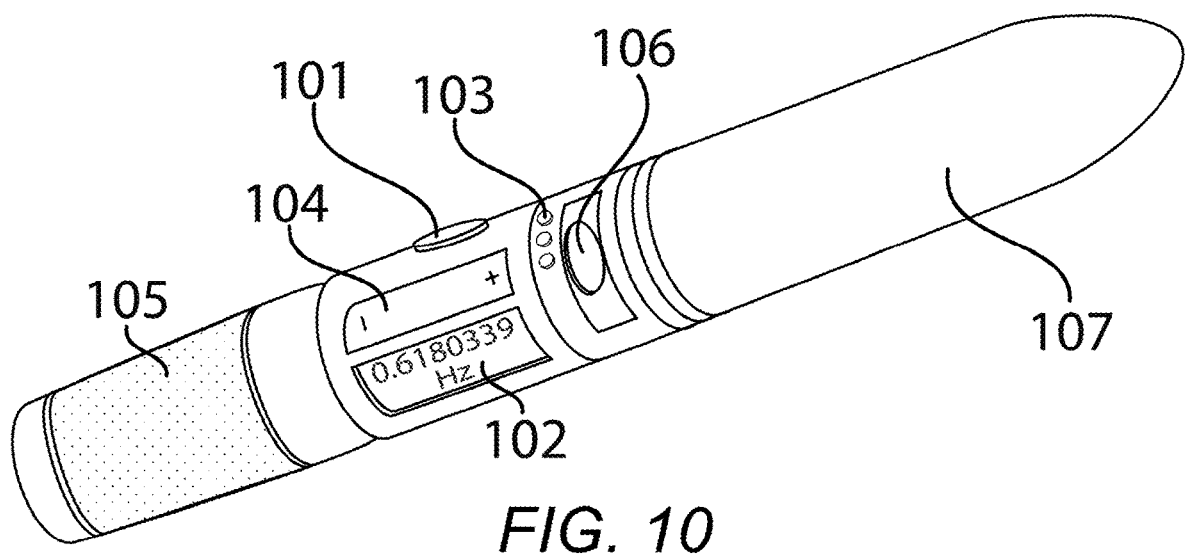

FIG. 10 in a illustrative embodiment depicts one of many possible configurations of the programmable transportable hand held frequency wave guide emitting probe of the current invention that is simplified for illustrative purposes that encompasses an on/off switch 101, frequency indicating display 102, illustrates some of many possible adjustment controls 103, battery power source 104, handle 105 and further including optional safety mechanisms (apparatus) that identifies the authorized operator(s) and or practitioner(s) by scanning a thumb, finger, and or hand (palm), and or other suitable safety encoding mechanism 106, for controlling dosage and administering the narrow and specific 0.6180 Hz sine wave frequency producing a narrow and specific window of frequency variance (accuracy) within 0.0001 Hz administered through the frequency emitting probe 107, producing a narrow and specific window of frequency variance (accuracy) within 0.0001 Hz administered during a complete ULF treatment schedule emitting an administered power ranging between about 0.01 watts and 2 watts, including a 15 minute emergency treatment exposure session, preferably having a resting and testing period (pause time) of about 3 to 5 hours between exposure sessions, for repair and enhancement therapy, to controllably expose at least one predetermined area of a human patient's body to the ULF stimulation therapy for targeted treatment such as vagina, rectum, open wound, and the like. The probe emitter system encompasses a diameter of about 25 mm (I inch) and a length of about 300 mm (12 inches).

Figure 11:
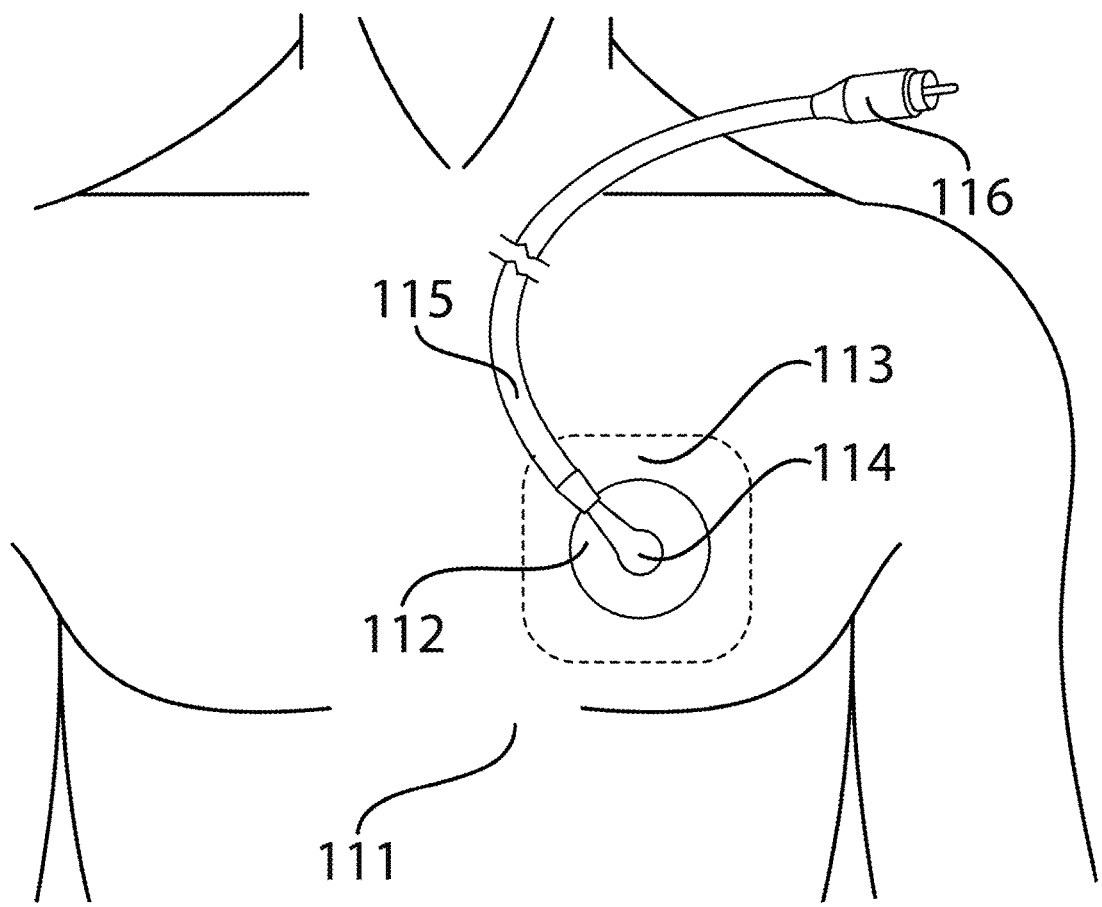

FIG. 11 in an illustrative embodiment depicts two of many possible configurations of the transportable, removable and or reusable epidermal patch ULF emitter apparatus and system attached to a patient 111 (may be attached to anywhere on the patient), illustrating two of many possible epidermal patch emitter systems in a circular configuration 112 and or a square configuration 113 encompassing an 0.6180 Hz sine wave micro-emitting apparatus 114, for administering the narrow and specific 0.6180 Hz frequency having an emitted power ranging between about 0.01 to 2 watts, emitting an accurate sine wave with narrow and specific window of frequency variance (accuracy) within 0.0001 Hz or more specific administered during the 15 minute exposure sessions, preferably within a complete treatment schedule for ULF repair and enhancement therapy to the patient, further illustrating an attachment cable 115 having a cable attachment terminal 116 connected to the frequency generating system and or amplifier system (not shown).

Figure 12:
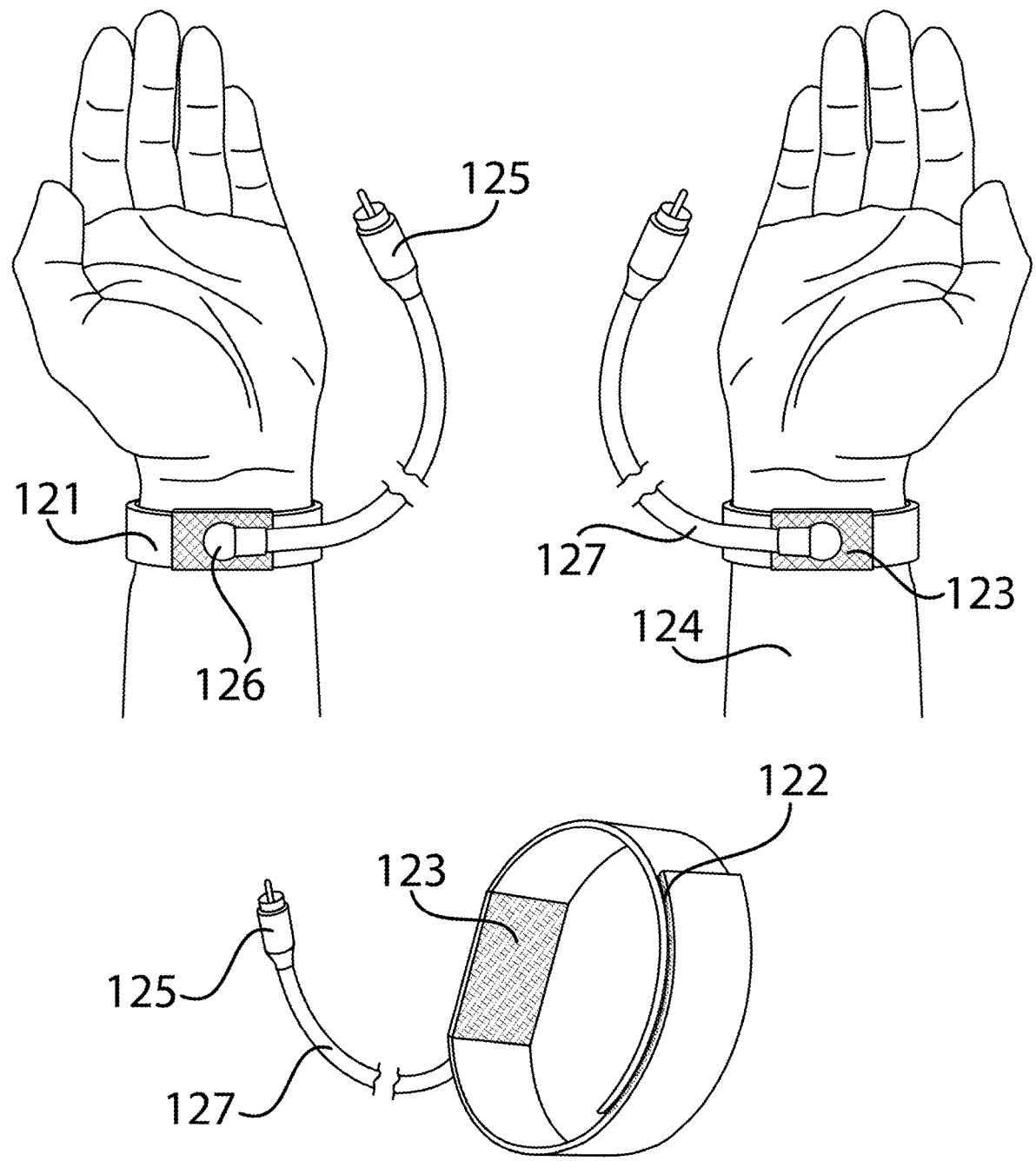

FIG. 12 in an illustrative embodiment depicts one of many possible configurations of the transportable wristband ULF emitter apparatuses and system 121 including attachment terminals having suitable attachment means 122 such as but not limited to Velcro®, having a frequency emitter 123 for administering the narrow and specific 0.6180 Hz frequency having an emitted power ranging between about 0.01 to 2 watts, emitting an accurate sine wave with narrow and specific window of frequency variance (accuracy) within 0.0001 Hz or more specific administered during the 15 minute exposure sessions, preferably within a complete treatment schedule for ULF repair and enhancement therapy to the patient.

Note this figure depicts in an illustrative manner that is simplified for illustrative purposes the ULF emitting wristband terminals positioned and or secured on a patient's wrists 124 illustrating one of the many possible locations, such as legs, feet, waist, chest, and the like, further depicting the cable attachment point 125 to the frequency generator and or amplifier (not shown) and or the cable attachment point to the wristband attachment terminal apparatus 126, and further depicting the connecting cable 127.

Figure 13:
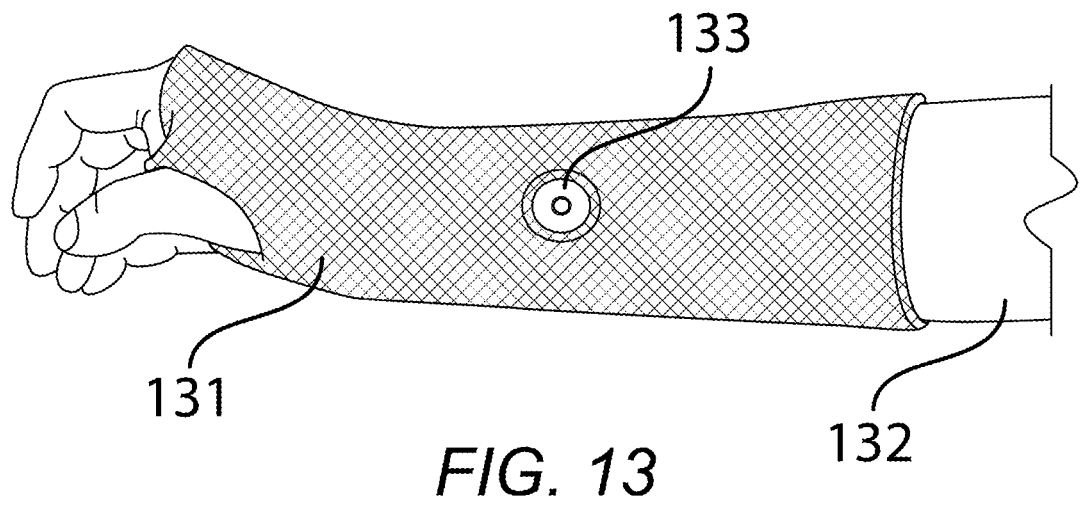

FIG. 13 in an illustrative embodiment depicts a tensioning cast apparatus 131 encompassing the patient's arm 132 and having an embedded ULF emitter apparatus and system 133 for administering the narrow and specific 0.6180 Hz frequency having an emitted power ranging between about 0.01 to 2 watts, emitting an accurate sine wave with narrow and specific window of frequency variance (accuracy) within 0.0001 Hz or more specific administered during the 15 minute exposure sessions, preferably within a complete treatment schedule for ULF repair and enhancement therapy to the patient. Attachment cable not shown.

Figure 14:
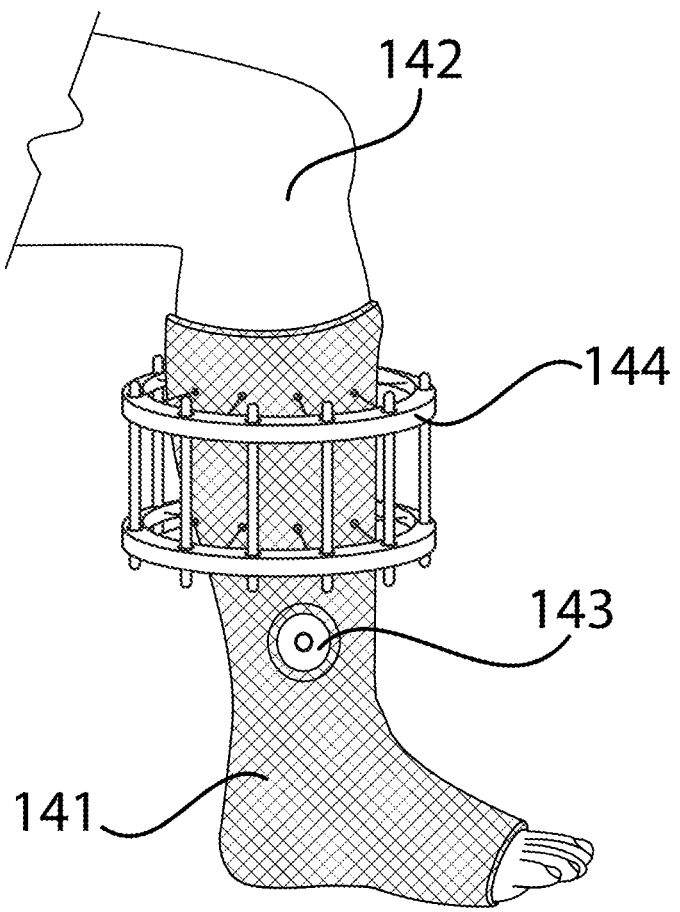

FIG. 14 in an illustrative embodiment depicts a tensioning cast apparatus 141 encompassing the patient's leg 142 and having an embedded ULF emitter apparatus and system 143 for administering the narrow and specific 0.6180 Hz frequency having an emitted power ranging between about 0.01 to 2 watts, emitting an accurate sine wave with narrow and specific window of frequency variance (accuracy) within 0.0001 Hz or more specific administered during the 15 minute exposure sessions, preferably within a complete treatment schedule for ULF repair and enhancement therapy to the patient, and further depicting an optional external fixation system 144. Attachment cable not shown.

Figure 15:
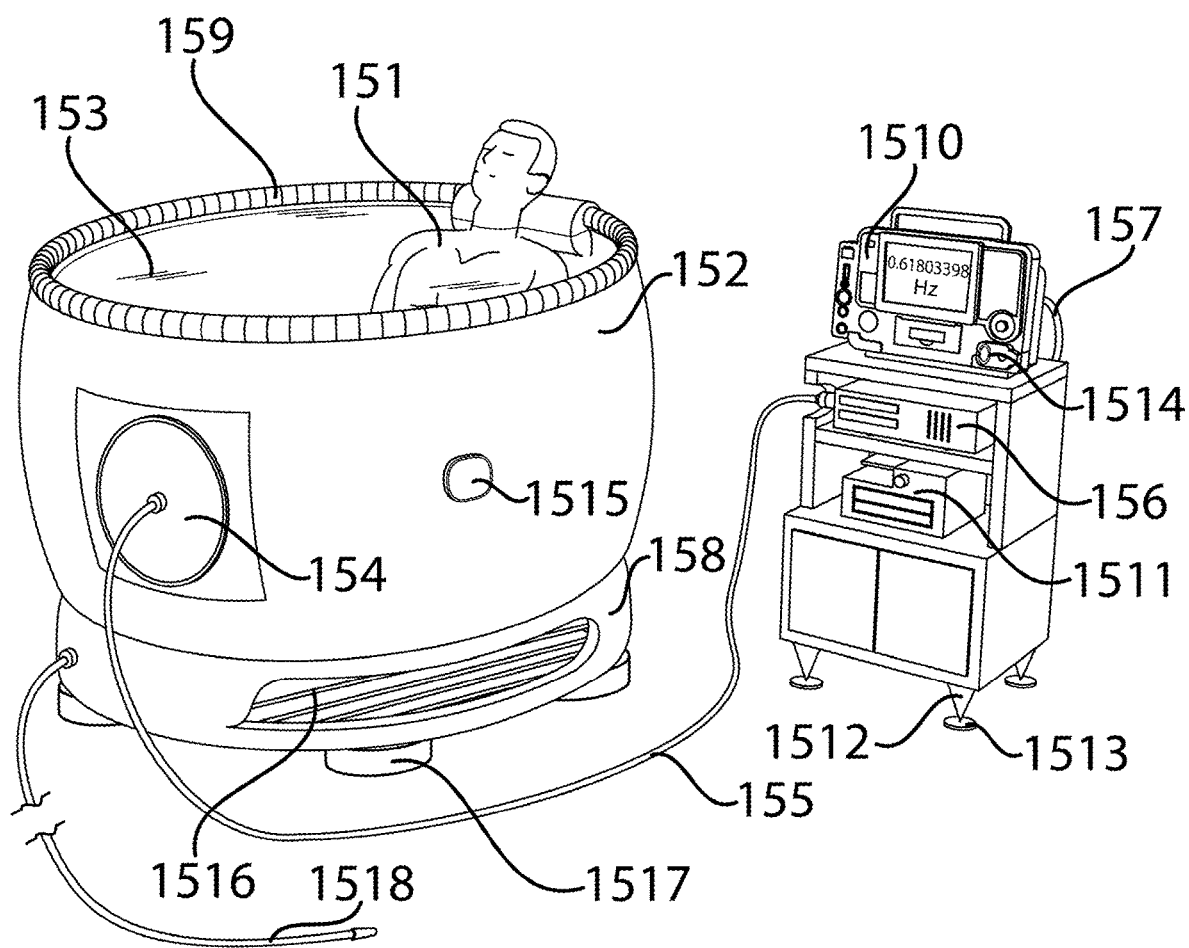

FIG. 15 in an illustrative embodiment a human patient 151 receiving ULF therapy in one of many possible configurations of an immersion water tank system 152 having temperature and or salinity regulated (optimized) water 153, further depicting a ULF emitter system 154, attachment cable 155 coupled to the amplifier 156, that is connected via an interconnect cable 157 to the frequency generator. Power cord not shown. The immersion water tank apparatus preferably includes an interference frequency dampening and or supporting ring collar base secured on the base 158, and or a frequency/vibration dampening ring around the edge of the immersion water tank 159. An optional adjustable patient safety supporting harness (not shown). The immersion water tank apparatus further includes faraday cage shielding characteristics employing electro-conductive materials as needed to achieve the needed faraday frequency interference canceling effects for accurately administering to the human patient a complete treatment schedule administering the narrow and specific 0.6180 Hz continuous sine wave frequency having an emitted power ranging between about 2 to 10 watts administered from a ULF generator 1510 continuously maintaining a narrow and specific window of frequency variance within 0.0001 Hz during the 15-minute exposure sessions for non-invasive systemic ULF repair and enhancement therapy, preferably having a resting and testing period (pause time) of about 3 to 5 hours between exposure sessions, preferably within a complete treatment schedule as needed observed with the illustrated ULF monitoring apparatus 1511. FIG. 15 further depicts an interference frequency canceling and or dampening cone 1512 and the corresponding frequency dampening receiving pedestal 1513.

FIG. 15 further depicts a ULF treatment system comprising a safety mechanism (apparatus) to identify the authorized operator(s) or practitioner(s) such as by scanning a finger, thumb, palm and or hand, and or employing other suitable encoding safety mechanism 1514, while further producing previously unavailable safety in the field of systemic human cell enhancement and or longevity assurance treatment schedules.

FIG. 15 further depicts the immersion water tank apparatus and system of the current invention that encompasses a monitoring display 1515 depicting the parameters and or metrics of the immersion water tank apparatus such as monitoring and or displaying temperature, exposure time (dosing), salinity, frequency, wave form, pH, oxygen content, the patient's bio-metrics.

FIG. 15 depicts a cut away view of a baffle interference frequency canceling/dampening apparatus 1516, and further depicts interference frequency canceling/dampening isolation mounts/feet 1517. FIG. 15 further depicts an optional grounding cable 1518.

Figure 16:
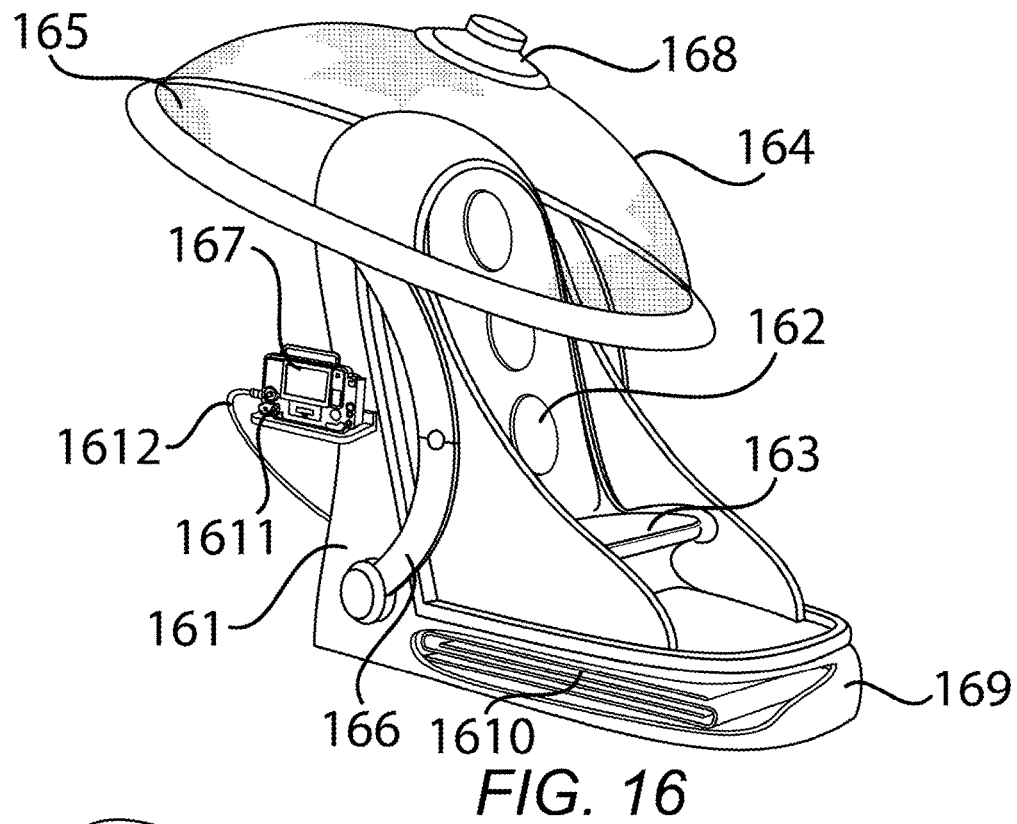

FIG. 16 depicts in an illustrative embodiment ULF generating and emitting pod apparatus for administering the narrow and specific 0.6180 Hz continuous sine wave frequency having an emitted power ranging between about 2 to 10 watts comprising a faraday shielding treatment pod dome in an open position 161 encompasses a cut away view of a baffle interference frequency canceling/dampening apparatus 162 forming a patient seat 163 enclosed by an elongated oval wave guide faraday shielding apparatus having interference frequency dampening characteristics for shielding and or canceling, further illustrating a domed transparent shielding canopy 164 for wave guide frequency shielding window formed therein composed of wire/mesh and or net faraday shielding materials 165 such as polypropylene dampening and or having metallic net wire interference frequency shielding materials, such as silver, copper, gold, and or other suitable electro-conductive mesh and or net materials. The bottom of the front of the dome shaped canopy is pivotally attached to the front of the base by hinged assembly 166 and may be locked in the open position on the base by a plurality of latches that are conjointly operated by an external lever and or an internal lever. The weight of the wave guide extending dome canopy upon opening is borne by a pair of side gas or spring struts wherein the diameter of the domed polypropylene interference frequency shielding canopy permits a human patient to sit within the dome shaped ULF treatment pod chamber seat for the patient to receive the narrow and specific 0.6180 Hz sine wave frequency generator 167 and one of the frequency emitting systems 168 continuously maintaining the narrow and specific window of frequency variance (accuracy) within 0.0001 Hz during the 15 minute exposure sessions comprising a complete and or programmable treatment schedule, preferably having a resting and testing period (pause time) of about 3 to 5 hours between exposure sessions, for ULF repair and enhancement therapy, and further permits the polypropylene and or wire mesh dome shaped interference frequency shielding enclosure chamber cover to be transportable and to fit through a standard double door opening in a direction perpendicular to the axis of the wall.

FIG. 16 further depicts the enclosure treatment dome pod's 161 ability to optimize and or regulate the 02 percentage within the therapy chamber pod (not shown) and adjusted to range between about 19.5 to 23.5%, and or regulating the chamber and patient's temperature (not shown), to optimize the ULF treatment schedules particularly for a patient in ultra-critical condition.

FIG. 16 further depicts the domed frequency treatment pod 161 and components of the treatment pods door hinge 166, the adjustable seat 163 for the human patient, the driver/frequency emitter 168, the platform 169, including a cutaway view of the ULF input and or output regulating baffle apparatus and system 1610, pre-programmed computer controllers for programming a complete frequency therapy treatment schedule as needed and further includes in real time monitoring of the patient's vitals, including a safety mechanism (apparatus) to identify the authorized operator(s) and or practitioner(s) such as by scanning a finger, thumb, hand and or palm, and or other suitable programmable safety encoding mechanisms 1611. The interconnect cable 1612 connects the frequency generator system and or the amplifier system to the frequency emitting system.

Figure 17:
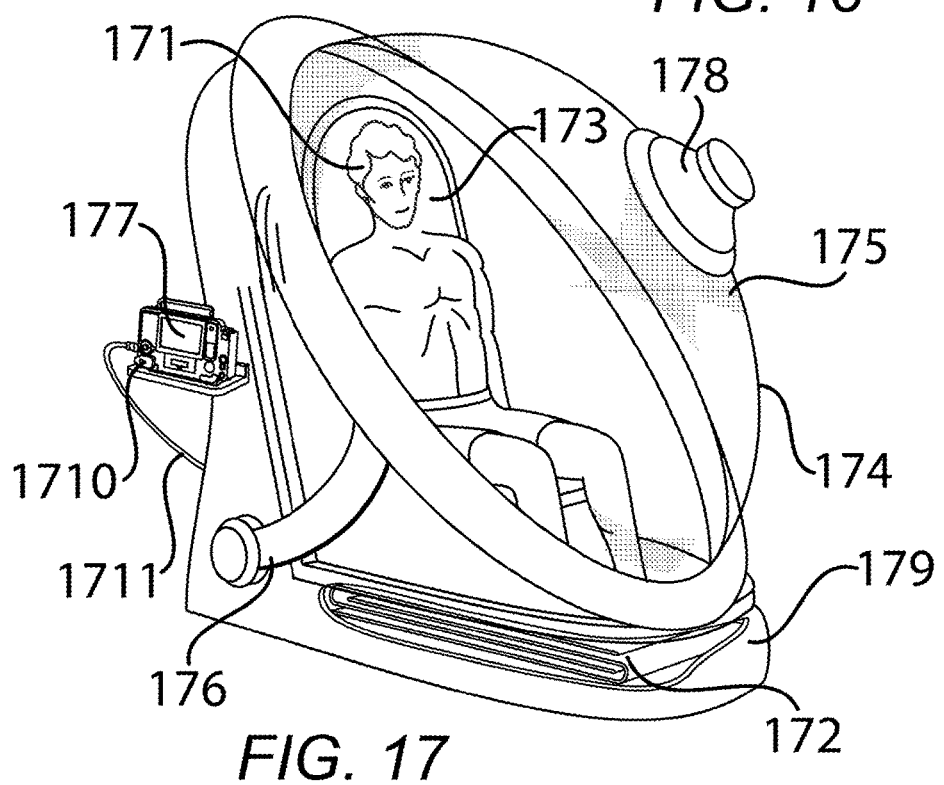

FIG. 17 illustrates a side view of an individual patient 171 seated in a ULF dome shaped treatment pod in the closed position that encompasses a cutaway view of an adjustable interference frequency baffling system 172 and an adjustable seat 173 enclosed by an shield elongated oval wave guide system further encompassing dampening interference frequency characteristics, having a domed shaped canopy 174 comprising a faraday frequency shielding transparent domed wave guide window formed therein made of suitable dampening materials such as polypropylene and or embedded wire/mesh shielding materials 175, such as silver, copper, gold, and or their alloys, and or other suitable electro-conductive wire mesh and or net materials as needed to achieve the needed faraday interference frequency shielding and or canceling effects. The bottom of the front of the domed canopy is pivotally attached to the front of the base by hinged assembly 176 and may be locked in the closed position on the base by a plurality of latches that are conjointly operated by an external lever and or an internal lever. The weight of the polypropylene wave guide extending faraday dome shielding canopy upon opening is borne by a pair of side gas or spring struts wherein the diameter of the polypropylene domed faraday interference frequency shielding and or canceling enclosure permits a patient to sit within the frequency treatment chamber for shielding of interference frequencies and an accurate dosing of the narrow and specific 0.6180 Hz administered continuous sine wave frequency employing one of many possible frequency generators 177 and or one of many possible frequency emitter systems 178 that can continuously maintaining the narrow and specific window of frequency variance (accuracy) within 0.0001 Hz or more specific as needed during the 15 minute exposure sessions within a complete treatment schedule administering the narrow and specific 0.6180 Hz continuous sine wave frequency having an emitted power ranging between about 2 to 10 watts preferably having a resting and testing period (pause time) of about 3 to 5 hours between exposure sessions for ULF repair and enhancement therapies as needed or desired, and further permits the polypropylene domed enclosure chamber to be transportable and fit through a standard double door opening in a direction perpendicular to the axis of the wall.

FIG. 17 illustrates the domed frequency treatment pod's ability to adjust and or regulate o2 percentage ranging between 19.5 to 23.5% (not shown), as well as further regulating the patient's temperature (not shown), in the therapy chamber as needed to optimize the administration of the ULF therapy.

FIG. 17 illustrates a ULF treatment pod components of the pod door hinge 176, a seat 173 for the human patient 171, the driver/frequency emitter 178, the pod's platform 179, a cut away view of the frequency input and or output frequency canceling baffle system 172, illustrates one of many possible pre-programmed computer controllers for programming the patient's complete frequency therapy treatment schedule including monitoring the patient's vitals, in real time including a safety mechanism (apparatus) to identify the authorized operator(s) and or practitioner(s) such as by key code, scanning a thumb, finger, palm (hand), and or other suitable safety encoding mechanisms 1710. The interconnect cable 1711 connects the frequency generator system and or the amplifier system to the frequency emitting system.

Figure 18:
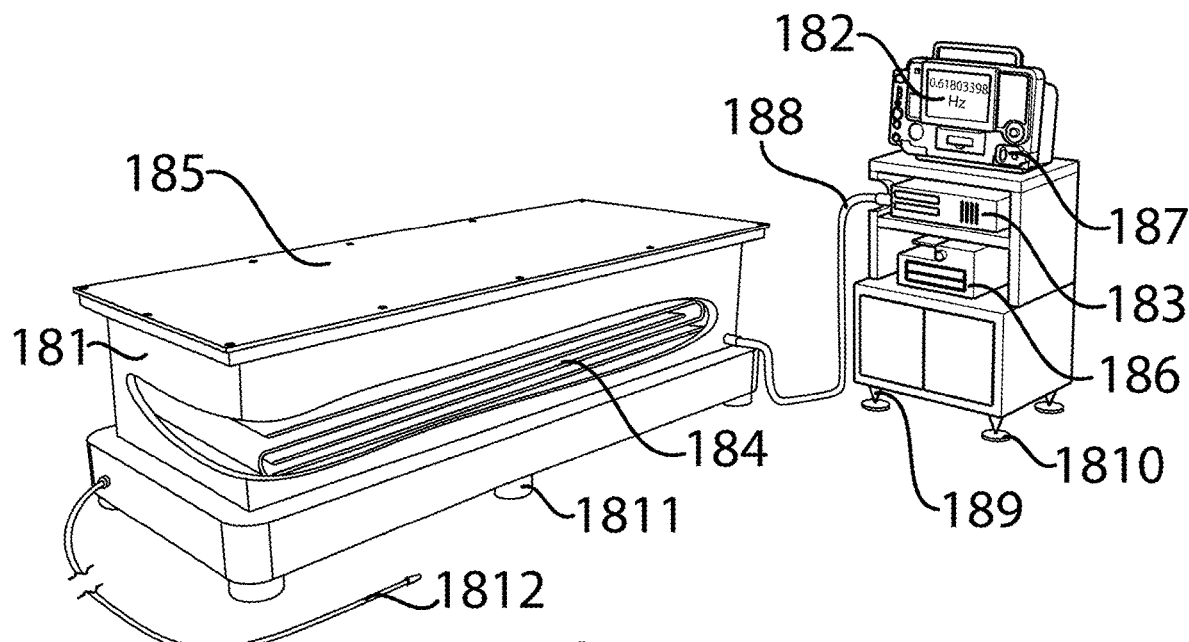

FIG. 18 illustrates one of many possible therapy treatment vibrating table apparatus configurations 181 for a complete ULF treatment schedule administering the narrow and specific 0.6180 Hz continuous sine wave frequency having an emitted power ranging between about 0.01 to 2 watts for systemically treating and or stimulating the human patient's entire body (not shown) (it shall be appreciated that other frequency targeted tissues are treated). The frequency treatment table apparatus comprises a ULF generator 182 and or amplifier 183 that is simplified for illustrative purposes further encompasses a cutaway view of an interference frequency canceling input and or output baffle apparatus 184 forming an adjustable supporting platform/bed 185 for the patient to lie down upon that may be enclosed by a frequency regulating wave guide system (not shown) further encompasses interference frequency dampening and or canceling characteristics, having a faraday frequency shielding enclosure formed therein and or made of suitable shielding materials such as dampening polypropylene having wire mesh and or net having interference frequency shielding materials, such as silver, copper, gold, and or their alloys, or other suitable electro-conductive wire mesh and or net materials as needed to achieve the preferred faraday interference frequency shielding, dampening, and or canceling effects, and further depicts one of many possible configurations of the invention's amplifiers, and computer controlled device for programming the ULF therapies including monitoring the patient's vitals and other biometrics 186, providing safety mechanisms (apparatus) to identify the authorized operator such as by scanning a thumb, finger, and or hand (palm), and or other suitable safety encoding mechanisms 187, and for accurately controlling the frequency source emitter for accurately administering the narrow and specific invention's 0.6180 Hz sine wave frequency having a narrow and specific window of frequency variance within 0.0001 Hz administered during the 15 minute exposure sessions 3 times per day having a resting and or testing pause time of about 3 to 5 hours between exposure sessions or as needed within a complete treatment schedule to a human patient for repair and or enhancement therapy. The cable 188 connects the amplifier system to the frequency emitting system. FIG. 18 further depicts an interference frequency canceling and or dampening cone 189 and the corresponding frequency dampening receiving pedestal 1810, further depicting vibration isolation mounts 1811. FIG. 18 further depicts an optional grounding cable 1812.

FIG. 18 further depicts a frequency table treatment system as well as further optimizing the temperature, oxygen content, and or environmental conditions (not shown), and the like, to optimize the 0.6180 Hz sine wave frequency therapy such as administered in an emergency situation and or for ULF treatment to a patient in ultra-critical condition.

Figure 19:
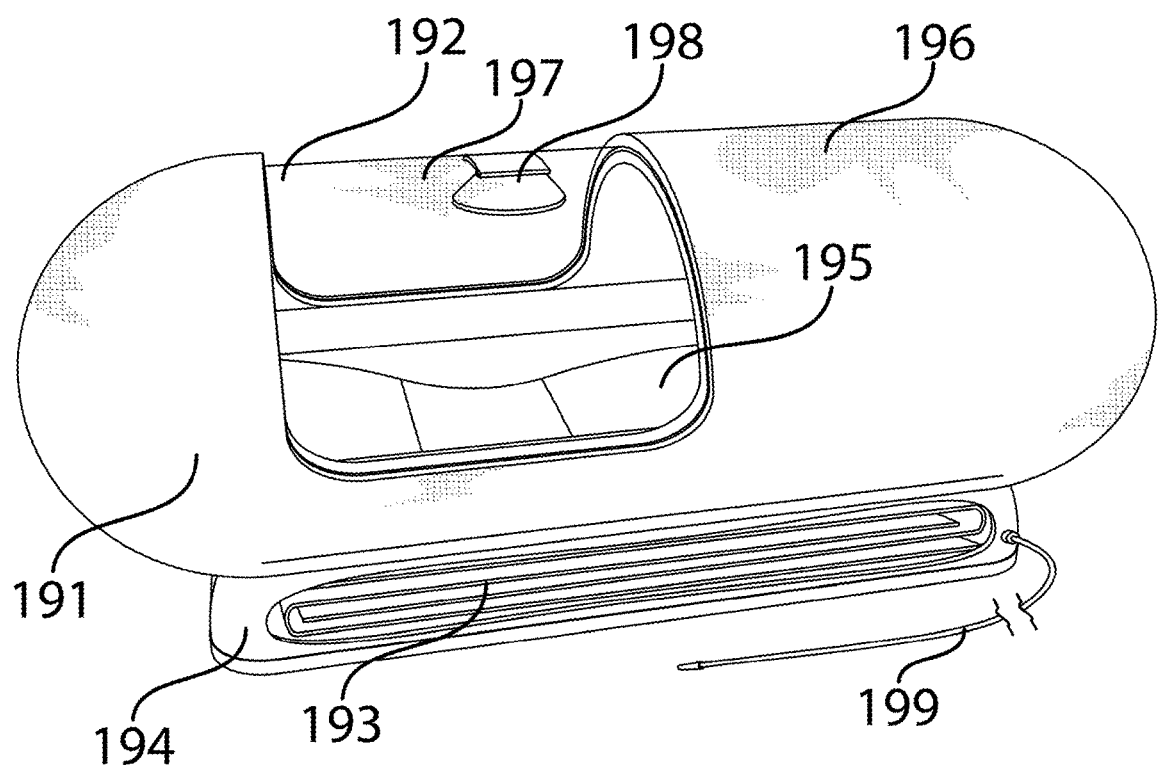

FIG. 19 illustrates one of many possible configurations of a ULF emitting treatment therapy encompassing a containment shell system 191 having a sliding chamber door 192 that includes a cutaway view of the ULF input and or output frequency regulating baffle system 193 forming a supporting platform 194, further depicting an adjustable bed 195 and an enclosed faraday shell containment capsule having a wave guide regulating system 196 further encompassing interference frequency dampening characteristics, with formed therein and made of suitable materials such as mesh reinforced polypropylene dampening and or interference frequency shielding materials, preferably silver, copper, gold, wire mesh and or net and or other suitable alloys and or other electro-conductive wire mesh and or net materials 197 as needed to achieve the interference frequency and faraday shielding characteristics including dampening/canceling effects. The human patient lies within the frequency generating and emitting containment shell having a ULF emitter/driver system 198 suitable for accurately administering the narrow and specific 0.6180 Hz frequency preferably emitting a sine wave having an emitted power of about 2 watts or more and having a narrow and specific window of frequency variance (accuracy) within 0.0001 Hz administered in 15 minute exposure sessions 3 times per day having a resting and or testing pause time of about 3 to 5 hours between exposure sessions or as needed within a complete treatment schedule for systemic repair and human enhancement therapies and further permits the containment shell to be transportable and fit through a standard double door opening in a direction perpendicular to the axis of the wall. FIG. 19 further depicts an optional grounding cable 199.

FIG. 19 further depicts a frequency containment shell treatment pod's ability to adjust to optimize and or regulate o2 with percentage in the pod's therapy chamber preferably adjustable ranging between about 19.5 to 23.5% (not shown), further including (regulating) the treatment pod's temperature (not shown) to help optimize the administration of the ULF administration therapy such as for patients in critical and or life threatening condition, such as burns, infections, and or radiation poisoning, etc.

Figure 20:
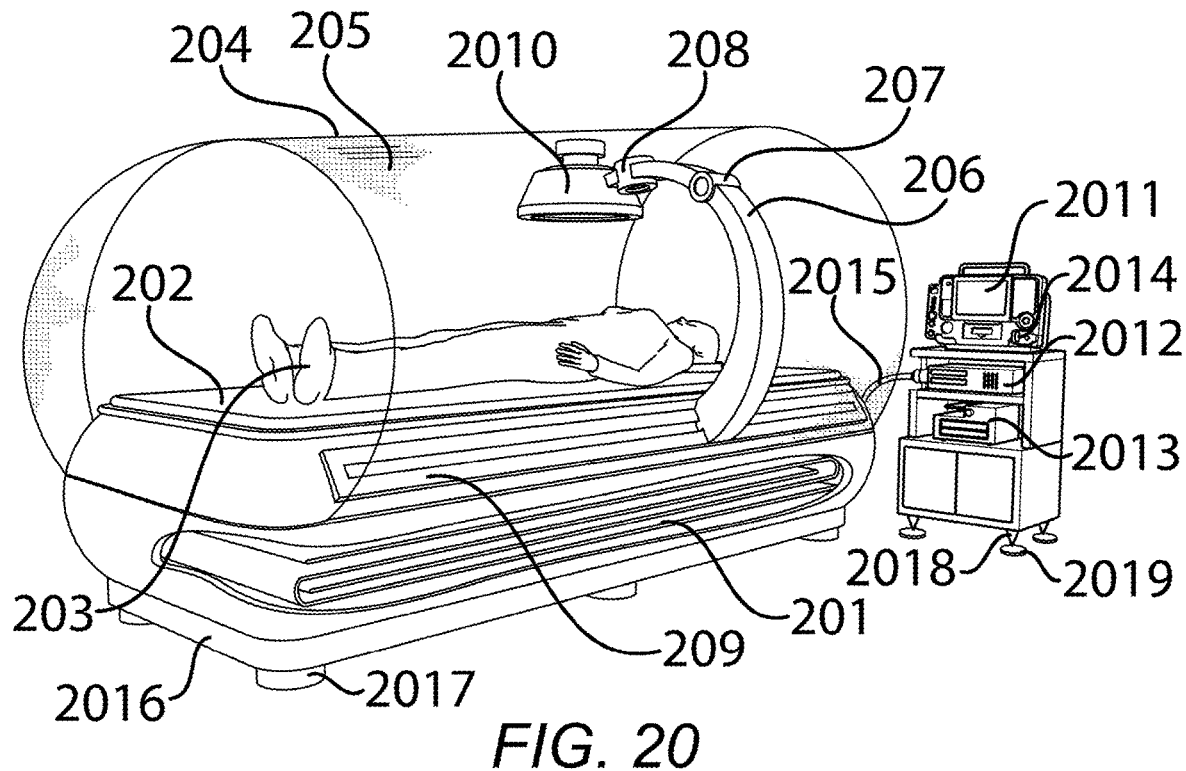

FIG. 20 in an illustrative embodiment depicts one of many possible transportable sealable ULF emitting treatment capsule is simplified for illustrative purposes that depicts a cutaway view of input and or output interference frequency regulating baffles 201 forming a supporting platform 202 for the patient 203 to lie down on that may be enclosed by an elongated capsule wave guide regulating and or shielding system 204 further encompassing interference frequency dampening characteristics and or faraday shielding, having a large capsule frequency shielding transparent domed cover wave guiding window formed therein made of suitable materials such as polypropylene encasing wire/mesh having interference frequency shielding mesh and or net configurations and materials 205, such as silver, copper, gold, and or other suitable alloys, and or other suitable electro-conductive wire mesh and or net as needed to achieve the needed interference frequency dampening shielding and or canceling effects, and further depicts having a mechanized frequency emitter source positioning arm 206 having vertical pivoting means 207 and horizontal pivoting means 208, such as but not limited to servo motors, that slides along the longitudinal railing system 209 up and down the length of the pod's treatment bed for accurately adjusting the three dimensional position (distance) of the frequency emitter source 2010 to accurately administer to a patient the narrow and specific 0.6180 Hz continuous sine wave frequency having an emitted power ranging between about 2 to 10 watts from one of many possible frequency generator systems 2011 to continuously maintaining the narrow and specific window of frequency variance (accuracy) preferably within 0.0001 Hz during the 15 minute exposure sessions 3 times per day having a resting and or testing pause time of about 3 to 5 hours between exposure sessions or as needed preferably within a complete treatment schedule for frequency stimulation repair and enhancement therapy or as needed.

FIG. 20 further depicts the treatment pod's ability to optimize and or regulate the o2 percentage inside the treatment chamber, adjustable between about 19.5% to 23.5% (not shown).

FIG. 20 further depicts the treatment pod's ability to optimize and or regulate the temperature inside the treatment chamber, preferably adjusted to range between about 87 to 93 degrees Fahrenheit and or adjusted as needed (not shown).

FIG. 20 further depicts one of many possible configurations of an amplifier 2012, and computer-controlled device 2013 for programming the ULF stimulation therapy to a patient and or monitoring the patients vitals and biometrics, including a safety mechanism (apparatus) to identify the authorized operator(s) and practitioner(s) such as by key code, scanning a thumb, finger, palm (hand), and or other safety encoding mechanisms 2014, further depicting a cable 2015 attaching the frequency amplifier to the frequency emitter system.

FIG. 20 further depicts a stabilizing and interference frequency dampening platform 2016, further depicting frequency dampening isolation mounts/feet 2017.

FIG. 20 further depicts an interference frequency canceling and or dampening cone 2018 and the corresponding frequency dampening receiving pedestal 2019.

Figure 21:
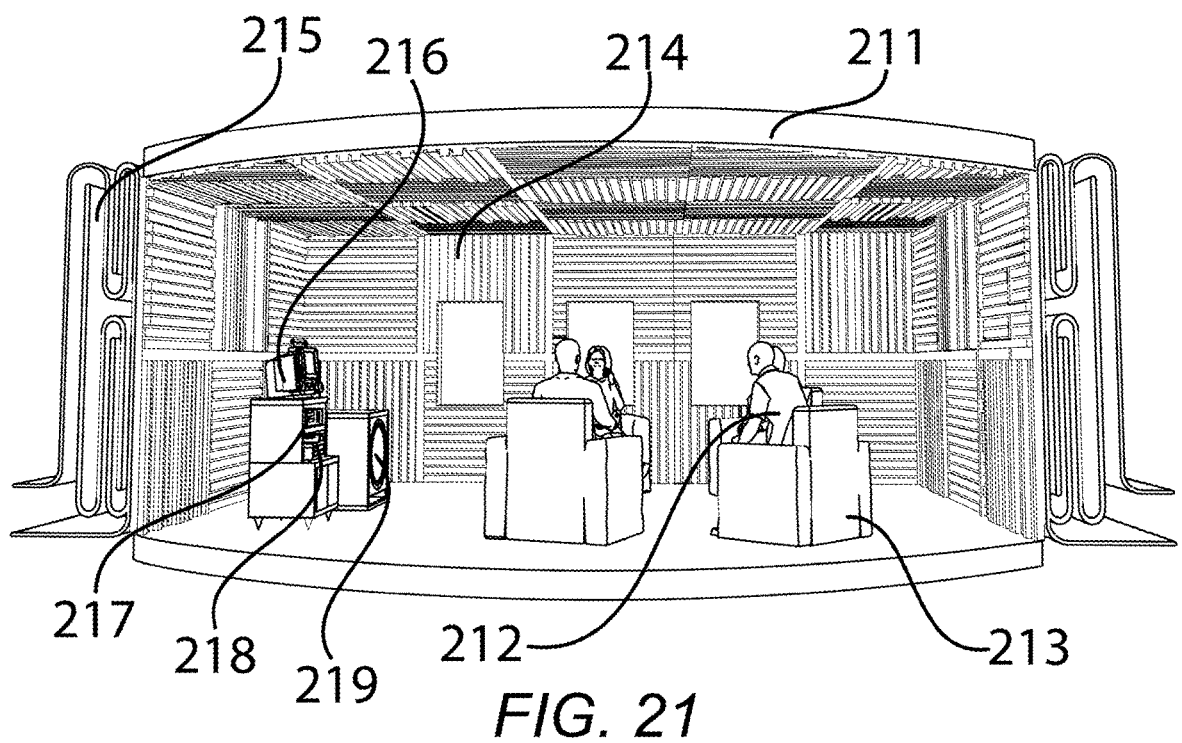

FIG. 21 in a illustrative embodiment depicts one of many possible configurations for an isolated frequency treatment room having a faraday cage ULF chamber 211 depicting 4 human patients 212 sitting in chairs 213 exposed to the invention's ULF continuous sine wave of 0.6180 Hz having an emitted power ranging between about 2 to 10 watts, and 214 depicts a cutaway view of an interference frequency dampening wall baffle system, 215 depicts a cutaway view of interference frequency dampening external baffles to obtain an accurate window of variance of 0.0001 Hz administered during the 15 minute exposure sessions 3 times per day having a resting and or testing pause time of about 3 to 5 hours between exposure sessions or as needed preferably within a complete treatment schedule.

FIG. 21 illustrates one of many possible configurations of the ULF therapy generator (frequency emitting source) 216, including an amplifier 217, computer controller 218 and one of many possible frequency emitter systems 219 for emitting the narrow and specific 0.6180 Hz continuous sine wave frequency as per the disclosed complete treatment schedules for systemic human patient repair and enhancement. FIG. 21 further illustrates a cut away view of the interference frequency isolating and or dampening baffled floor and or wall 214 system having a cutaway view of external interference frequency canceling input and or output baffles 215. The isolated ULF therapy treatment room may further include ambient oxygen regulation (from about 19.5 to 23.5%) to optimize the patient's frequency stimulation therapy (not shown). In a prophetic example the ULF therapeutic field effect (field saturation), from the ULF emission source emitting a continuous sine wave frequency of 0.6180 Hz having a narrow and specific window of frequency variance of 0.0001 Hz or more specific administered to a patient during the preferred 15-minute exposure sessions preferably having a resting and or testing pause time of about 3 to 5 hours between exposure sessions or as needed within a complete treatment schedule.

FIG. 21 illustrates a treatment room that encompasses a sufficient volume of the patient's electromagnetic field for producing a significant bio-stimulative therapeutic effect, as disclosed herein the current invention encompasses administering the ULF therapy to a patient in a frequency isolated room (chamber), preferably having a diameter ranging between about 12 feet to 30 feet preferably the frequency emitter distance (inverse square) ranging between about 6 inches to 12 feet from patient's body, depending upon the specific application.

Figure 22:
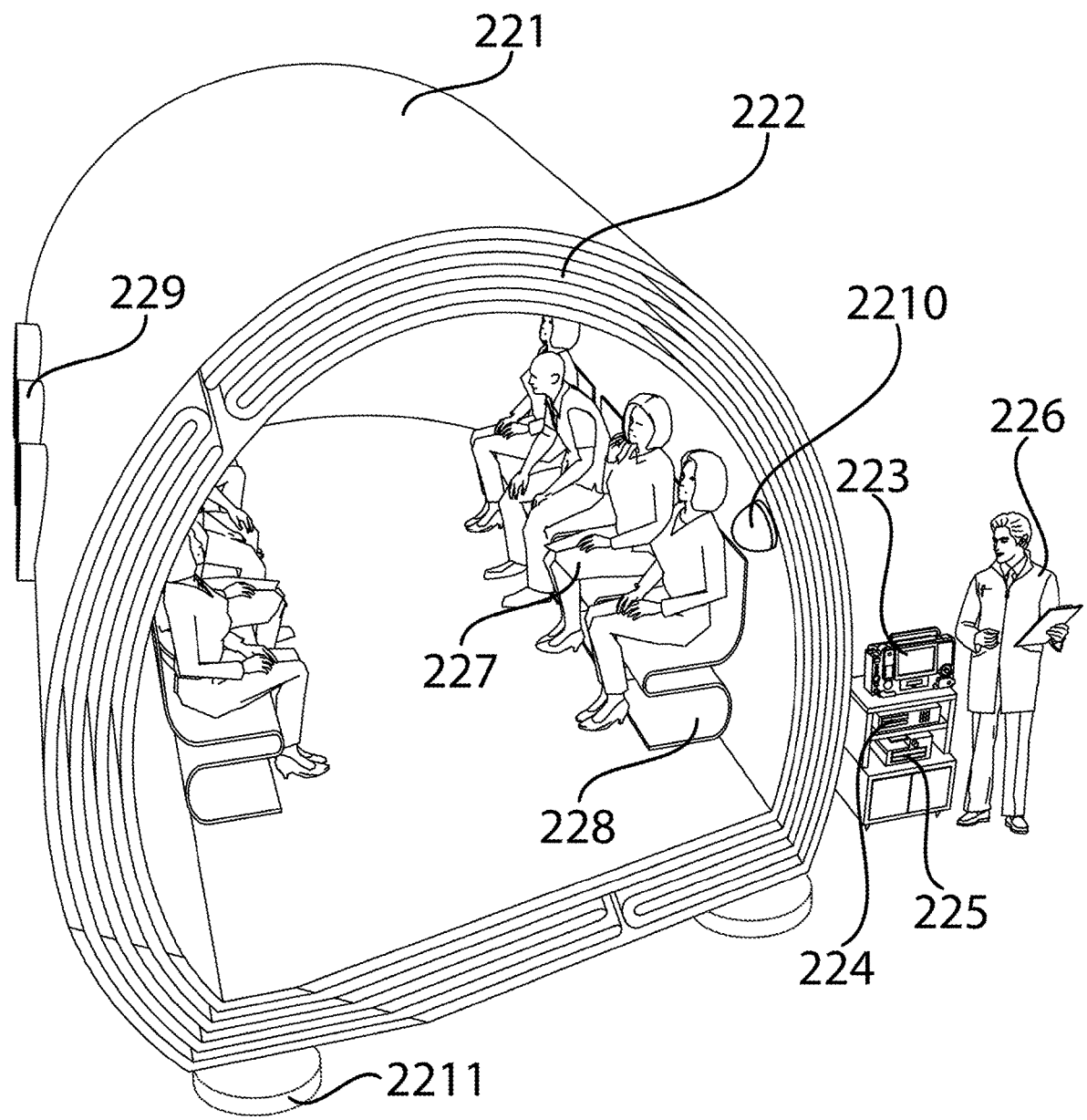

FIG. 22 in an illustrative embodiment depicts a perspective view with a cutaway of a hyperbaric room/chamber 221, comprising a cutaway view of an adjustable internal interference frequency baffling system 222, for administration of a complete ULF treatment schedule administering the narrow and specific 0.6180 Hz continuous sine wave frequency having an emitted power ranging between about 2 to 10 watts employing a frequency generator system 223, a frequency amplifier 224, and a computer controller 225, that is programmed and or operated by the authorized operator(s) and or practitioner(s) 226, further depicting a patient or patients 227 sitting in a seat or seats 228, further including an optional viewing window(s) 229, and an optional camera system 2210 for monitoring the patient(s). Further depicted is the interference frequency dampening/canceling system (isolation mount(s)) 2211.

Figure 23:
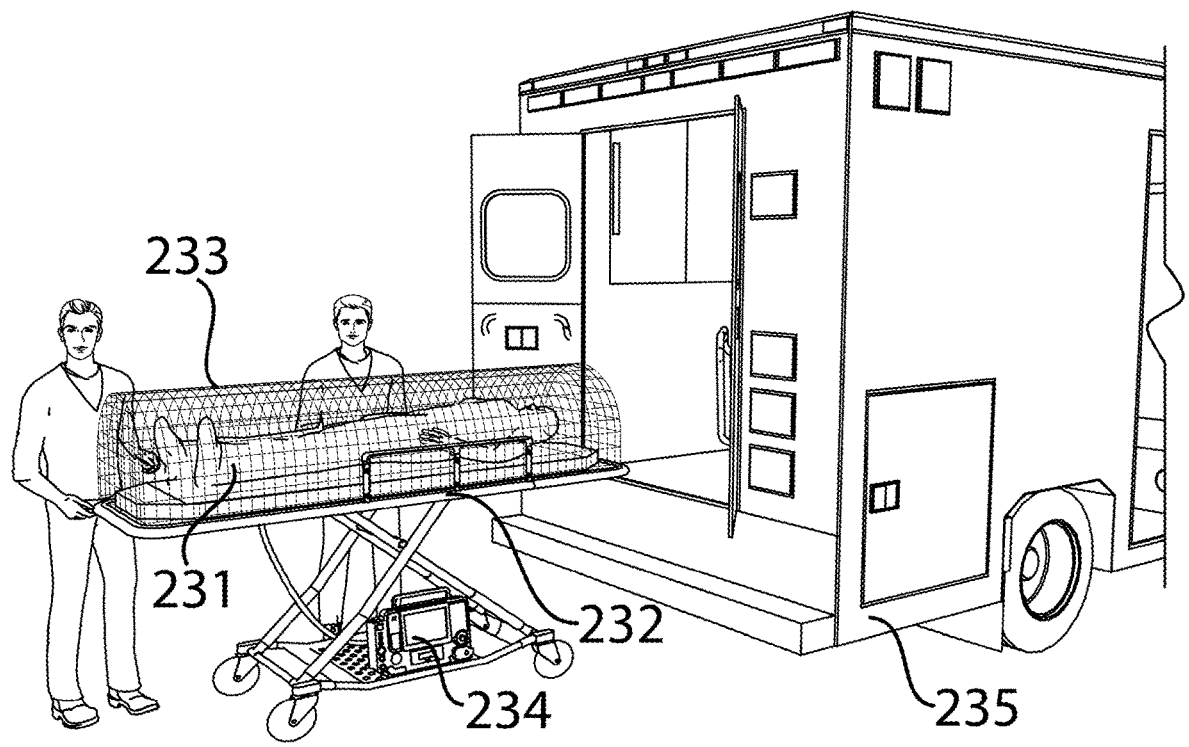

FIG. 23 in an illustrative embodiment encompasses one of many possible configurations of a human patient 231 being transported on a transported optionally adjustable gurney 232 positioned within a collapsible transportable semi-spherical faraday interference frequency shielding cage 233 that is constructed of suitable flexible materials such as wire mesh and or polypropylene having frequency canceling characteristics and or alloy materials, such as including silver, copper, gold, and or their suitable alloys, and or other suitable electro-conductive materials as needed to obtain the preferred faraday interference frequency canceling effects, and or having air-flow through characteristics. The transportable collapsible ULF treatment shielding chamber further optimizes the ULF treatment environment, such as administered to a patient in an emergency or life-threatening situation, that monitors the patient's biometrics in real time, including administering an emergency ULF dosages having parameters and or outcomes as defined herein such as administering the narrow and specific 0.6180 Hz continuous sine wave frequency having an emitted power ranging between about 0.01 to 10 watts administering to the patient a 15 minute exposure of the 0.6180 Hz continuous sine wave frequency through one of many possible frequency generator systems 234 and ULF emitter systems having frequency variance within 0.0001 Hz during the emergency exposure session having a resting and or testing pause time of about 3 to 5 hours between exposure sessions or as needed and or preferably part of a complete treatment schedule as disclosed herein.

The transportable ULF shielding treatment cage may be used for onsite emergency frequency therapy, preferably in conjunction with the transportable handheld pistol wave guide emitter system ULF administration immediately to a patient before and or during transport, such as in an ambulance 5 to significantly improve the patient's survival and or recovery rate and enhance the long-term therapeutic effects, including extending the conventional 'Golden Hour'.

Figure 24:
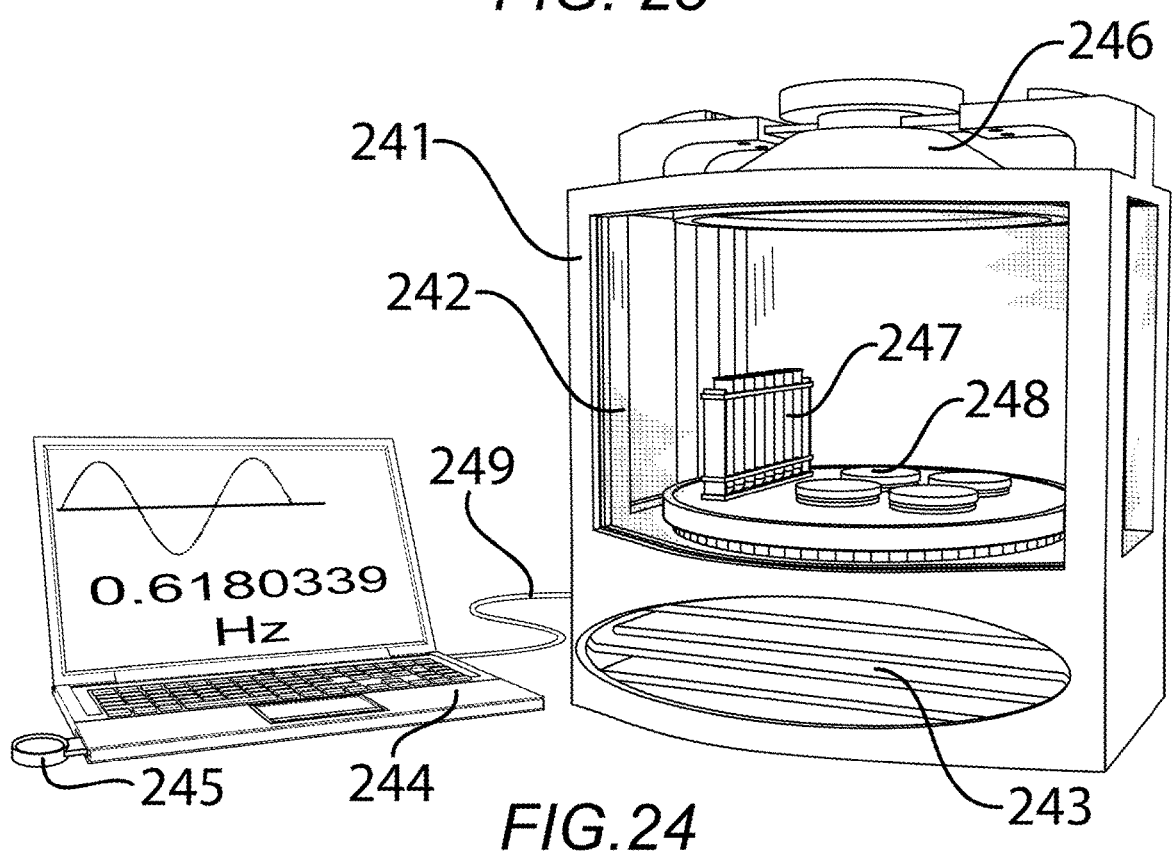

FIG. 24 illustrates one of many possible desktop frequency treatment culturing chamber's configurations having faraday interference frequency shielding enclosure 241 for ULF stimulation therapy administered for in vitro cell and or organ transplanting, repair and enhancement including but not limited to transplanting heart, lungs, spleen, liver, and the like, including ULF treatment for blood processing and or transfusions, the ULF exposure treatments repairing and enhancement for blood purification, preservation and or storage, further including enhancing all prior stem cell process(es) at any prior art step(s) such as but not limited to/frequency stimulating during culturing steps stimulating stem cell production in vitro for genetic repairing and enhancement such as enhancing CRIPSR processes, and the like, preferably constructed of an essentially air-impermeable polypropylene frequency canceling materials and or having encapsulated wire alloys for interference frequency shielding (faraday cage), including silver, copper, gold and or their alloys, and the like, and or other suitable electroconductive wire mesh and or net materials 242, to optimize biometric frequency stimulated conditions including adjusting the atmospheric pressures, including regulating the optimized atmospheric oxygen percentage adjusted to range between about 19.5 to 23.5% (not shown), and or to regulate the chamber's internal temperature (not shown), for optimizing cellular, blood, and or whole organ enhancement utilizing an adjustable gantry platform system to optimize the relationship for preferred watt dosing, further including a cutaway view of the input and or output frequency canceling baffles 243, further encompassing a suitable computer 244 mechanism (apparatus) to control and or monitor the ULF treatment schedule parameters, and further depicts a security device to identify the authorized practitioner or operator such as scanning a finger, thumb, palm and or hand, and or other suitable safety encoding mechanisms 245 for providing safe accurate ULF therapy dosing such as administering therapeutic intervention for human organ enhancement and or damaged cell or tissue repairing administered from a programmable ULF complete treatment schedule and or having accurate platform adjustments (inverse square) for accurately administering the narrow and specific 0.6180 Hz continuous sine wave frequency from a programmable controller employing one of many possible frequency generator systems (not shown) and one of many possible frequency emitter systems 246 for preferably emitting and maintaining a continuous accurate sine wave (continuous sine wave form is most preferred) having an adjustable and programmable power range between about 0.0001 watts to 2 watts, and having a narrow and specific window of frequency variance (accuracy) within 0.0001 Hz or more specific during the administered 15 minute exposure sessions, preferably having a resting and or testing period (pause time) of between about 3 to 5 hours between each exposure session, preferably within a complete treatment schedule, for ULF repair and enhancement therapy as needed or desired such as for ULF accurately dosing to test tubes 247, petri dishes 248, parts of or whole organs (not shown), etc. 249 depicts the cable coupled between the laptop system and the computer mechanism and the desktop frequency treatment culturing chamber.

Figure 25:
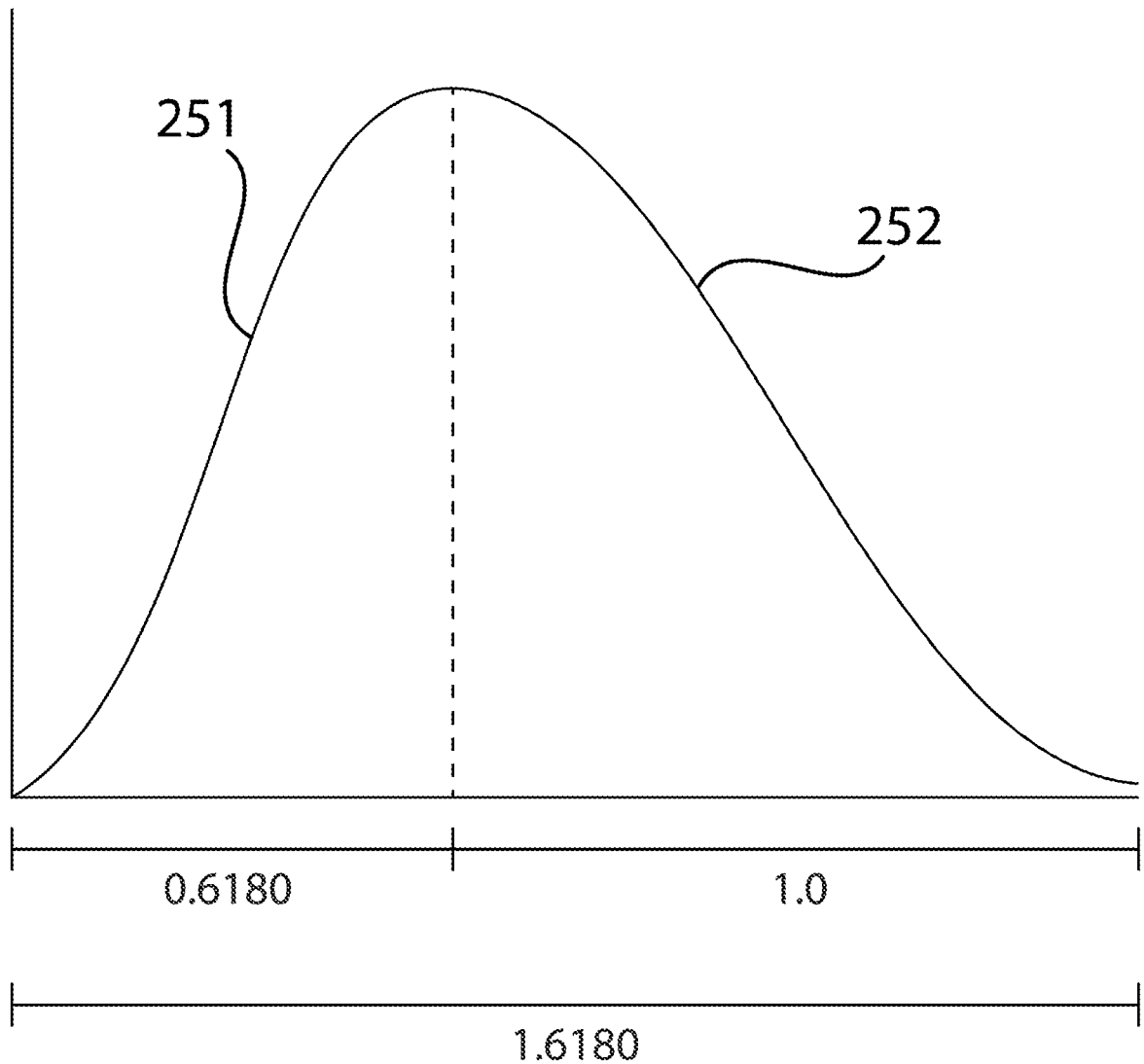

FIG. 25 depicts a wave form of the current invention having a ratio of the wave form incline 251 to the wave form decline 252 of 0.6180.

APPARATUSES FOR FREQUENCY THERAPIES

Figure 4:
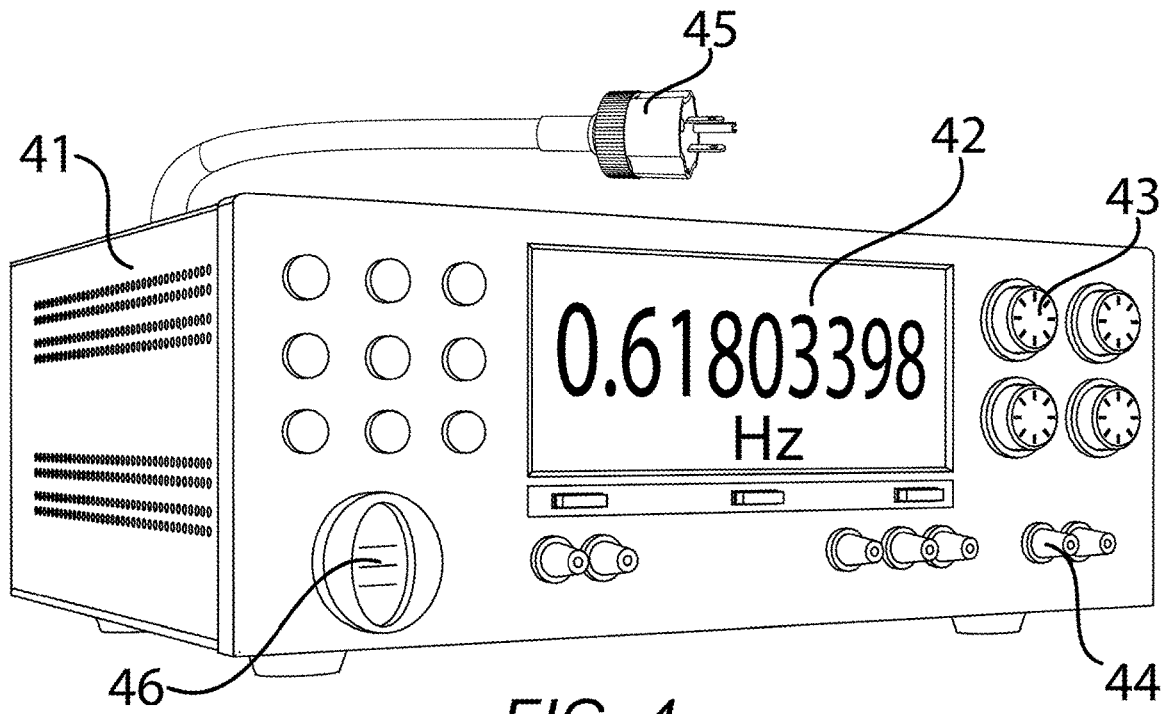

In several specified embodiments the apparatuses and methods of the current invention encompasses frequency generating and transmitting apparatus for transmitting and or indicating the power (watts), the preferred sine wave form, resting and or testing time(s) between exposure sessions, and or accurate exposure times of the emitted 0.6180 Hz frequency having a narrow and specific window of frequency variance (sufficient accuracy) within 0.0001 Hz or more specific as needed to the frequency amplifier and or emitter system during the 15 minute frequency exposure sessions, preferably having a resting and or testing period (pause time) of between about 3 to 5 hours between each exposure session, preferably within a complete treatment schedule for ULF repair and enhancement therapy as needed or desired, and further encompasses a safety mechanism (apparatus) to identify the authorized practitioner(s) or operator(s) such as key codes, scanning a thumb, finger, palm, whole hand, retinal scan, and or other audio and or visual encoding mechanism, further including a pin key pad, and or other suitable safety encoding mechanisms, and the like, reference FIG. 4.

The current invention simplifies complex operator(s) or practitioner(s) training and operation for the ULF frequency stimulation equipment as disclosed herein.

As discussed above, in a prophetic example the ULF therapy involves systemic therapeutic administration of FST energy to a human patient for obtaining a wide variety of localized and systemic bio-stimulatory and other desirable biological repairing and enhancement effects including complete disease remission, further including cancer and or tumor regression. In other prophetic examples, the FST comprises several devices that may be employed to administer the FST therapy to a human patient.

The ULF generating source illustrated by FIG. 4 comprises at least one power conduit (not shown) coupled to a power source (not shown). In some embodiments, the power conduits comprise an electrical conduit which is adapted to accurately transmit ULF 0.6180 Hz (frequency) signals and pre-selected watt (power) dosage such as employing ULF generator diode and or ULF generation emitting diode, and the like, to a wave guide frequency emitter of the current invention. In certain embodiments, the watt (power) conduit comprises an ULF conduit (e.g., ULF waveguide) which accurately transmits ULF sine wave signal of 0.6180 Hz and power to the emission output area of the ULF emitting system through an optional frequency, power, wave form monitor/indicator, reference FIG. 5, while continuously maintaining a continuous narrow and specific window of variance (accuracy) of 0.0001 Hz or more specific as disclosed herein while preferably producing and maintaining an accurate continuous sine wave or optional saw tooth wave form. Note administering a continuous sine wave is most preferred.

In certain embodiments, the ULF system of the current invention encompasses optional control panels, fuse(s), surge breaker(s), power indicating light(s), alarm system(s), flashing light(s), brakes, locks, and the like (not shown).

interconnects and or transmitting cables, including coaxial cables, that optionally filters out transmitted frequencies that are outside of the narrow and specific 0.6180 Hz frequency, and further include further narrowing the window of variance to be more specific then the 0.0001 Hz window of variance as disclosed herein.

In certain embodiments, the ULF system of the current invention encompasses a safety mechanism that controls, regulates, and or operates the frequency generating apparatus (machine) such that the system is incapable of producing and or emitting frequencies outside of the narrow and specific 0.6180 Hz frequency range.

In certain embodiments, the ULF system of the current invention optionally encompasses wireless ULF transmission such as IR wireless communication, satellite communication, broadcast radio, Microwave radio, Bluetooth, induction cooling, and the like.

In certain such embodiments, the ULF generating source comprises at least one ULF generating apparatus, and/or waveguide system, which accurately transmits the frequency transmitter received via the frequency conduit. In still other embodiments, the computer controlled ULF generating and emitting apparatus contains a power source (e.g., a battery) and or the power conduit is substantially internal to the ULF 0.6180 Hz therapy administration apparatuses.

In certain such embodiments, the ULF generating apparatus is coupled to a ULF monitoring apparatus which may optionally serve as a further wave guide, reference FIG. 5.

Frequency Stimulation Parameters

It is desirable to administer to a human patient an efficacious amount (therapeutic dose or dosage) as needed of FST energy for systemically and or frequency targeting internal tissue to be treated using FST source preferably accurately positionable outside, near, and or in direct contact with the human patient's body, as illustrated in FIGS. 6, 7, 8, 9, 10, 11, 12, 13 and 14 as disclosed herein.

Figure 1:
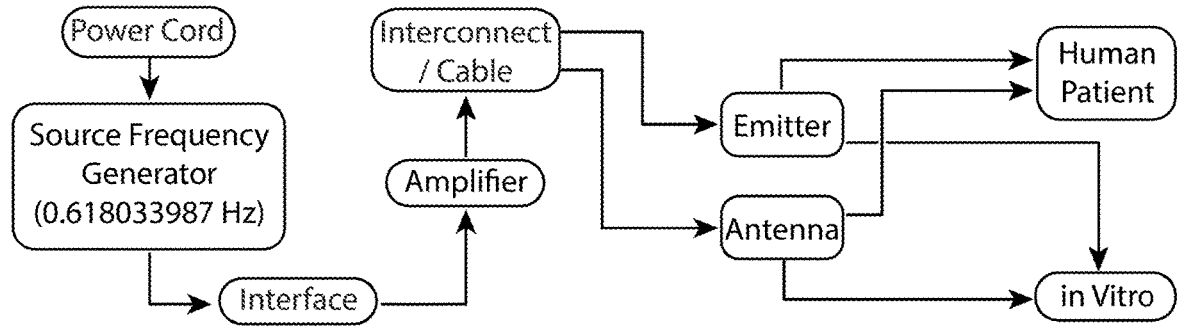
FIG. 1 illustrates a schematic representation (flow chart) of the ULF treatment components of the current invention, encompassing the power cord, frequency generator transmitting the narrow and specific 0.6180 Hz sine wave frequency and continuously producing a narrow and specific window of frequency variance (accuracy) of 0.0001 Hz or more specific as disclosed herein from one of many suitable amplifiers of the current invention, that are connected through interface cables and or interconnects, which amplifies and transmits the power to be administered from one of many possible emitter and or antenna systems to administer the ULF treatment schedule to a human patient and or to in vitro processing systems as described herein.

The current invention encompasses administering treatment schedules and applications for the ULF therapy, with predefined parameters and criteria for producing the desired field saturation effects, reference FIG. 1.

In a prophetic example the inventors theorize that the resistance of the skin and or human physiology is such that the permeability to electrical current (skin resistance) has a maximum capacity of less than about 0.2 amps.

In a prophetic example the inventors theorize that the ULF frequency administration structures all of the RNA and DNA in the environment to their preferred structure in accordance with the 0.6180 ratio.

The current invention encompasses that the preferred ULF 0.6180 Hz sine wave frequency administration encompasses that the absorbed watts (power) by the human patient is between about 0.2 watts and 1 watt, or more as needed, and further that the administered power may be adjusted as needed to suit a preferred absorbed watt dose as needed.

In an exemplary embodiment that the current invention encompasses that the human patient preferably absorbs about ⅒th of the frequency power (watts) that they are exposed to; for example, about 0.2 watts when exposed to about 2 watts.

In certain exemplary embodiments, the ULF apparatuses and methods preferably administered optimal watts and complete ULF stimulation energy densities to the intended frequency targeted damaged tissue, within acceptable margins of error as described herein providing preferred dosing (absorption) characteristics.

In an exemplary embodiment, the current invention encompasses that the electrical current that is administered to a human patient is preferably below about 0.2 amps to prevent overdriving the physicality of the human patient and or experiencing frequency and or power resistance.

In a specified embodiment, the current invention encompasses that the preferred power (watts) emitted from the ULF emitter systems of the current invention is about 0.01 to 10 watts, as disclosed herein such as but not limited to apparatuses such as wrist band, frequency emitting pistol, Ultra-Low Frequency Vibration Table, removable epidermal patches, antenna systems, Rotary Driver system (reference FIG. 6), Ultra Low Frequency Vibration generator, Speaker drivers, Ultra Low Frequency Pulse Generator, Ultra-low frequency driver of the current invention employing stealth technology and or frequency canceling cones, Ultra Low Frequency Pulse Resonator, Electrostatic Loud Speaker (ESL) Panel, Ac2ated Sound®, Electromagnetic Driver systems. Acoustic Surface Technology, Antenna systems (reference FIG. 7), Piezoelectric Cantilever Beam (reference FIG. 8), Tesla ASTROD Device available from www.ElectroHerbalism.com, tesla coil systems, Ultra-low Frequency transducers, such as but not limited to immersible underwater transducers, flextensional transducers, hydroacoustic, electromagnetic, and or active material-based, and the like, Ultra Low Frequency Drivers, pencil driver systems, leaf springs, and the like that meet the pre-defined parameters and or criteria disclosed herein. The current invention further encompasses that any ULF emitter system may be modified as needed to accurately meet the invention's pre-defined parameters and or criteria disclosed herein, further including driver/emitter component materials not disclosed herein.

The current invention as disclosed herein eliminates the common prior art limitation of producing excessive heat.

In certain embodiments, an administered surface wattage of the 0.6180 Hz sine wave frequency energy is provided for sufficient ULF energy penetration to the patient's whole body.

The determination of the administered dosage required surface wattage, which is relatively higher than the watt to be absorbed by the human patient's body (or other) tissue being frequency treated, takes into account factors that attenuate wattage as it travels through the patient's intervening tissue, including the weight of the human patient. The watt power and or other treatment schedule parameters are then determined according to the results of such calculations.

The current invention encompasses administering a complete ULF treatment schedule administering a 0.6180 Hz sine wave frequency having an emitted power of about 0.0001 watts or more, of about 0.001 watts or more, of about 1 watt or more, about 2 watts or more, about 4 watts or more, about 6 watts or more, about 8 watts or more, about 10 watts or more, or 10 watts or less and any range between and including the watt values provided.

The current invention encompasses administering a ULF treatment exposure session administering a 0.6180 Hz sine wave frequency for a time period of about 5 minutes or more, about 8 minutes or more, about 10 minutes or more, about 12 minutes or more, about 15 minutes or more, about 20 minutes or more, about 20 minutes or less, and any range between and including the ULF exposure session time values provided.

As an example, deviations by more than about 15% from standardized height to weight ratios, such as BMI and the like, would result in a drop off of efficacy as the patient's mass increases.

The current invention encompasses that the preferred emitted watts (power) is related and dependent to the distance (inverse square) from the ULF emitter source to the human patient and for in-vitro and or in vivo treatment schedules.

The current invention further encompasses administering, to a human patient, the ULF therapy having a voltage up to about 20 volts, depending upon the application and or a variety of factors such as but not limited to dosage and or distance (inverse square) between patient and emitter system, emitter system employed, complete treatment schedule and apparatus and method of administering the frequency therapy such as from pistol emitter system, immersion tank system, treatment pod, treatment capsule, open air emitter system, treatment room system, wrist band emitters, in vitro culturing chamber, frequency vibration table, and the like. Reference FIG. 2.

The current invention encompasses a transportable hand held frequency emitting pistol for administering the narrow and specific 0.6180 Hz frequency therapy having an accurate sine wave form of the narrow and specific 0.6180 Hz frequency exposure maintaining a window of variance of 0.0001 Hz to a human patient in an emergency environment by administering the 15-minute frequency exposure session having an emitted adjustable power ranging between about 0.01 to 5 watts administered to a patient about every 3 to 5 hours or as needed.

The current invention encompasses that the ULF therapy sessions (treatment schedules) encompass a preferred wattage dose of what the human patient is exposed to (directly experienced) is below about 10 watts, further including ULF administration within in vitro culturing chamber(s) to cells, organs, blood transfusions, and the like.

The current invention encompasses that the preferred exposure distance of the human patient from the antenna frequency emitting apparatus ranges between about 28 cm (11 inches) and 152 cm (5 feet), adjusted as needed depending upon the application, such as employing an immersion tank therapy.

In a prophetic example the various parameters of the generated and emitted 0.6180 Hz sine wave frequency from the antenna frequency emission surface of the frequency emitter system are advantageously selected to stimulate systemic suppression and or complete remission of conditions, disorders and or diseases and or to stimulate systemic enhancement characteristics while controlling, inhibiting, preventing, minimizing, and or eliminating discomfort to the human patient.

The current invention apparatuses and methods encompasses that the current invention is incapable of producing ULF administration beyond the pre-programmed safety features' parameters outside of the preferred treatment criteria and or parameters as defined herein.

Frequency Therapy

The following section discusses theories and or potential action mechanisms, as they currently appear to the inventor, regarding the selection of the narrow and specific therapeutic continuous sine wave frequency of 0.618033987 Hz preferably having a narrow and specific window of variance of 0.0001 Hz or more specific of ULF generating and emitting frequency for stimulation of human enhancement therapy described herein. The scope of the claims of the current invention is not to be construed to depend, relevance, or specifics of any of these theories and or potential action mechanisms. Thus, the claims of the current application are to be construed without being bound by theory or by a specific mechanism.

In a prophetic example in certain embodiments, administering of the non-invasive and drug free ULF therapy of 0.6180 Hz frequency dosing places practical limits on the narrow and specific sine wave frequency treatment schedule administered to the human patient that is selected in view of one or more of the following considerations:

(1) the ability to systemically stimulate mitochondrial function in vivo; (2) the significantly ability to penetrate systemic tissues; (3) the FST complete absorption in the frequency targeted tissue; (4) the efficacy in ischemia models in vivo (inside the body); (5) the dosing of FST generating sources administering the desired dosing (watts) within the complete ULF treatment schedule administering a preferred sine waveform; (6) the ability to systemically stimulate human genetic repair and enhancement within a human patient; (7) the ability to significantly improve and enhance conventional stem cell therapies including enhancing stem cells, and further including enhancing the patient's tissues to which those cells are delivered: (8) the ability to increase and or enhance the stem cell bio-active secretions; (9) the ability to stimulate the production and or release of the human patient's own (autologous) stem cells (ranging between about 50 million into the billions of stem cells per 15 minute exposure session); (10) the ability to provide suppression and or complete remission of any known injury, condition, and or disease; (11) the ability to provide suppression and or complete remission of cancer, (12) the ability to administer an accurate frequency of the narrow and specific 0.6180 Hz sine wave frequency having a window of variance (accuracy) of 0.0001 Hz or more specific as disclosed herein; (13) the ability to administer the non-toxic non-invasive ULF therapy within the preferred power (watts) range between about 0.01 watt and about 10 watts; (14) the ability to accurately administer the ULF treatment schedules within the preferred amperage range: (15) the ability to accurately administer the ULF therapy within the preferred voltage range; (16) the ability to use a computer controller system to accurately adjust and control the parameters of administration of complete ULF treatment schedules.

In other exemplary embodiment encompasses that the combination of these effects is a result of a narrow and specific sine wave frequency administered to a patient as a non-toxic therapeutic frequency treatment including in vivo and or in vitro applications. These factors may be combined in certain embodiments to create therapeutic gain and or complete remission from a wide variety of conditions, disorders and or diseases as disclosed herein. This is an object of the invention.

In a specified embodiment encompasses administering to a human patient an accurate sine wave form. A continuous sine wave form is most preferred, or an optional continuous saw tooth wave may be administered.

In a specified embodiment encompasses that administering a complete ultra-low frequency treatment schedule emitting a 0.6180 Hz frequency in a continuous sine wave form having a wavelength of about 15 nm and an amplitude of about 24.27 nm is most preferred.

In a specified embodiment encompasses that the continuous wave form has a ratio of the wave form incline to the wave form decline of 0.6180, reference FIG. 25.

In a specified embodiment encompasses that the continuous wave form has a ratio of the wave form decline to the wave form incline of 0.6180.

In a specified embodiment, the current invention encompasses administering to a human patient any periodic waveform including the following: Sine wave, saw tooth wave, square wave, Triangle wave, further including an accurate custom wave form and or wave forms as needed. Sine wave and or Saw tooth wave form are preferred, continuous sine wave is most preferred.

The current invention further encompasses custom wave forms not specifically defined herein.

Note, the Fourier series describes the decomposition of periodic waveforms, such that any periodic waveform can be formed by the sum of a (possibly infinite) set of fundamental and or harmonic components. Finite-energy non-periodic waveforms are encompassed by the current invention may be analyzed into sinusoids by the Fourier transform.

Note, other waveforms are commonly referred to composite waveforms and are often described as a combination of a number of sinusoidal waves and or other basis functions added together.

While the emitted wave form has an ultra-low frequency of 0.6180 Hz, the inventors theorize that specific harmonics of higher frequencies will specifically affect the cellular structures on the human patient.

In a specified embodiment encompasses that the administered ULF 0.6180 Hz treatment schedule therapy, preferably produces and maintains an accurate continuous sine wave absorption and transmittance through the patient's intervening tissue, and further encompasses that the therapeutic gain of the ULF sine wave energy distance (inverse square) delivery is a function of emitter power, frequency, amperage, and or voltage that may be calculated and adjusted as needed, including to a specific patient.

The inventors theorize that for administering biometrical training, the more stable the administered sine wave frequency and accurate shape of the waveform the higher the coherence experienced by the human patient biological system.

The current invention encompasses a supporting apparatus such as but not limited to adjustable seats, beds, and or supporting harnesses, that provide a variety of ergonomic movements and position adjustments to the patient's body before, during, and or after the ULF treatment therapy to further enhance biological entrainment to the 0.6180 Hz frequency as disclosed herein, such as moving the ankles, hips, or spine in accordance with the accurate and specific 0.6180 Hz frequency, reference FIGS. 15, 17, and 18.

In certain embodiments, the ULF generator will be programmed (e.g. with non-transmissive materials) to emit an accurate continuous, or optionally pulsed, sine, saw tooth, rectangular, oval, or other geometric wave shape or form in the selected length. Note continuous saw tooth or sine wave is preferred. Continuous sine wave form is most preferred.

In certain exemplary embodiments encompasses preferably a single frequency emitting FST source is preferably employed as an ULF emitter for ULF stimulation therapy to a patient so as to reduce and or eliminate frequency interference from employing multiple frequency emitter systems simultaneously.

The current invention encompasses a single frequency generating source for administering the 0.6180 Hz sine wave therapy through multiple frequency emitting systems.

The current invention preferably encompasses a single frequency generating source for administering the 0.6180 Hz sine wave therapy through a single frequency emitting system.

The ULF stimulation (frequency generator) source preferably accurately generates a continuous sine wave of 0.618033987 Hz continuously maintaining a narrow and specific window of variance (accuracy) of 0.0001 Hz or more specific as needed depending upon the application.

In certain embodiments, the FST generating source comprises one or more ULF generator diodes, which each provide accurate 0.618033987 Hz continuous sine wave frequency generation.

In certain embodiments, the ULF generator system includes at least one continuously accurately emitting frequency generator diode having a continuous sine wave frequency of 0.618033987 Hz.

The current invention encompasses modifying/upgrading any electrical components, including those of the frequency generator, frequency amplifier, frequency emitter system, and the like, such as to upgrade to the invention's disclosed specs such as but not limited to diodes, electrodes, capacitor, and the like to suit the application and its pre-defined parameters and or criteria as defined herein.

The current invention further encompasses ULF component systems such as but not limited to frequency generator systems, amplifier systems, frequency emitter systems of the current invention employing stealth enclosure (not shown) technology and or frequency canceling cones, reference FIG. 15 and FIG. 20).

Frequency Generator Systems

In several specified embodiments encompasses in an apparatus aspect an accurate sine wave ULF generation producing device (at 0.6180 Hz), also known as ultra-low frequency generator, function generator, and the like which accurately generates the 0.6180 Hz continuous sine wave frequency while maintaining the preferred narrow and specific 0.6180 Hz frequency within a narrow and specific window of variance (accuracy) of 0.0001 Hz or more specific as disclosed herein such as but not limited to the following, reference FIG. 4:

Siglent SDG1032X 30 MHz Function/Arbitrary Waveform Generator. Frequency range: 0.000001 Hz (1 µHz) to 30.2 MHz, available from www.siglent.eu Stanford Research DS345 Synthesized Function Generator. Frequency range: 0.000001 Hz (1 pH-z) to 30.2 MHz, available from www.bellnw.com Siglent Technologies SDG2042X Arbitrary Waveform Generators, ranging from 0 Hz to 40 MHz, available from www.amazon.com, and or EasyWave software.

Siglent SDG1025 Function/Arbitrary Waveform Generator, ranging from 0 Hz to 25 MHz, available from www.amazon.com Agilent 8165A Function Generator. Frequency range: 0.0001 Hz to 50 MHz, available from www.valuetronics.com Siglent Technologies SDG810 Siglent Single Channel ranging from 0 Hz to 10 MHz Signal Generator, Waveform available from www.amazon.com.

Pasco PI-9587C Digital Function Generator/Amplifier. Frequency range: 0.001 Hz to 99,999 Hz, available from www.pasco.com Pasco PI-8127 Function Generator. Frequency range: 0.001 Hz to 100 kHz, available from www.pasco.com DJB Microtech A2-2503.50 Function Generator with built in 10 W Amplifier. Frequency range: 0.001 Hz to 10.00 MHz, available from www.djb.co.uk MHS-5200A Digital DDS Dual-channel Signal Generator Source Frequency Meter 13N2 operates at a frequency range of 0.01 Hz to 25 MHz available from www.banggood.com.

Kuman 0.01 Hz to 30 MHz High Precision Dual-channel DDS Arbitrary Signal Waveform Generator Counter, Frequency meter, Modulation Function FY6600 available from www.amazon.com GB4000 Function Generator which operates at frequencies ranging between about 0.1 to 20 million Hz, available from https://www.quantumbalancing.com/gb4000.htm.

Koolertron 0.1 Hz to 15 MHz High Precision DDS Signal Generator Counter, Arbitrary Waveform Generator Function Frequency Meter 266 MSa/s (15 MHz) available from www.amazon.com.

Koolertron 0.1 Hz to 30 MHz DDS Signal Generator High Precision Dual-channel Arbitrary Waveform Generator Frequency Meter 200 MSa/s (30 MHz) available from www.amazon.com.

Low Frequency Impulse Magnetotherapy Device available from https://www.theinstituteofnaturalhealth.com/about1-clflj Further encompasses a variety of signal generators available Do It Yourself designs for Infrasound devices and Infrasonic converters, available on www.techlib.com.

The ITorus and or Table Top ITorus V3 available from ipyramids.net.

The current invention encompasses that the ULF 0.6180 Hz sine wave frequency generator systems may be modified as needed to accurately meet the invention's pre-defined parameters and or criteria disclosed herein.

In certain such embodiments, the power conduit interface (e.g., flexible circuit board), may be coupled to an ULF conduit within a ULF component, such as the ULF generator system, the amplifier system, the emitter system, and or the computer controller, which produces accurate frequency transmission characteristics to the ULF emitter apparatus. The frequency transmitter interface of certain embodiments comprises a frequency generating and emitting device which accurately transmits the 0.6180 Hz sine wave frequency while maintaining the preferred narrow and specific 0.6180 Hz frequency within a narrow and specific window of variance (accuracy) of 0.0001 Hz or more specific. In other embodiments, the power conduit interface is adapted to be coupled to an electrical conduit which provides electrical power to the ULF generating and emitting apparatuses. In certain such embodiments, the power conduit interface comprises one or more in line filters diodes, the output of which is distributed among the ULF system.

The current invention encompasses a ULF generator system that includes an integrated amplifier.

The current invention encompasses ULF generator systems that are analog and or digital. Analog ULF generator system is preferred for sine wave generation.

The current invention apparatuses and methods encompasses electrical (frequency) signals from the power source and or frequency generating system to the amplifier and or frequency emitter system for accurately emitting and administering the ULF therapy to a patient. In such embodiments, the power conduit interface comprises circuitry adapted to distribute the electrical signal to appropriate portions of the FST emitting apparatus.

In addition, in a prophetic example the current invention frequency generator systems and or amplifier incorporates safety mechanisms (apparatuses) to identify the authorized operator(s) and or practitioner(s), and or encompassing optional interlocks may be provided so that the ULF generator apparatus may not be activated (operated) unless the appropriate safety measures are taken as needed to provide sufficient safety and or security in the field of ULF therapy including human repair and enhancement, further including significant expansion of normal mortality and or enhancement of stem cell therapies in general.

The inventive therapeutic frequency generating apparatuses further includes a power supply operatively coupled to the ULF frequency generator and incorporating a programmable computer controller operatively coupled to the ULF generating source and or to the power supply. The programmable computer controller is preferably configured to control the ULF generating and transmitting source so as to produce and maintain an accurate predetermined treatment schedule administering a continuous sine wave form, administering the ULF therapy to a human patient's body having an adjustable emitted power ranging between about 0.01 to 10 watts and a patient absorbed power of ranging between about 0.001 to 1 watts (note about $\frac{1}{10}$th of emitted power is absorbed).

The source of certain embodiments is responsive to the trigger switch by emitting ULF generation only when the safety trigger switch is actuated (not shown).

Frequency Monitoring

In several specified embodiments, the apparatuses and methods of the current invention encompasses a variety of transportable frequency and or watt indicating and or monitoring apparatuses including connection cords, and or indicating screens for frequency, watts, wave form selection, and or programmable treatment schedule selection dials, reference FIG. 5.

The current invention encompasses a control circuit comprising a securable programmable computer controller according to embodiments described herein. The control circuit is configured to adjust the pre-programmed timing and or frequency including wave form and or watts (power) of the ULF therapeutic energy (frequency) emitted by the FST generating and emitting source to generate a predetermined treatment schedule corresponding to a predetermined stimulation energy delivery profile to the human patient's body, such as a predetermined subsurface wattage, preferably producing and maintaining an accurate continuous sine wave form, and or dose/timing.

In certain embodiments, the programmable controller comprises a logic circuit, a clock and or counter coupled to the logic circuit, and or an securable operator input/interface coupled to the logic circuit. The clock of certain embodiments provides a programmable timing signal to the logic circuit so that the logic circuit may control and or monitor the FST dosage timing and or preferred intervals in real time of the administered FST therapy, reference FIGS. 15, 18, 20, 21, 22, 24

Examples of ULF dosing and or timing intervals include, but are not limited to the total frequency exposure treatment times, wave form of applied ULF therapy, and or the preferred time and or dosing intervals between the administered FST therapy.

The computer interface may comprise a user interface and or an interface to a sensor system(s) monitoring at least one parameter of the ULF generating and emitting FST therapy.

In certain such embodiments, the computer programmable controller is responsive to the patient monitoring the feedback signals from the sensor systems to adjust the ULF generating and emitting treatment parameters if needed to optimize the human patient's repair and enhancement. The adjustable programmable computer controller may thus provide closed-loop monitoring and or adjustments of various frequency dosing levels and or treatment schedule's parameters to optimize the human patient's personalized in real time frequency treatment therapy to the individual human patient the feedback signals provided by the interface from an operator are indicative of parameters that may include, but are not limited to, human patient characteristics (e.g., weight, age, fat percentage), selected applied watts, wave form, emitter distance to the patient, frequency exposure time, the resting and or testing intervals (pause time), and or watts/timing profiles for the applied ULF and emitting FST therapy.

In certain embodiments, the computer logic circuit is coupled to a ULF generator system and wave guide frequency emitter and or driver system.

In certain embodiments, the logic circuit is responsive to signals from a sensor monitoring system including at least one parameter of the pre-programmable treatment schedule(s) to monitor and or control the applied ULF generating and emitting source. Other embodiments include, for example, biomedical sensors including, but not limited to, a biomedical sensor from the group consisting of: a blood flow sensor, a blood gas (e.g., oxygenation) sensor, an ATP production sensor, blood, saliva, and or urine pH sensors, stem cell secretion monitors and or sensors, oximeter sensors, pulse oximeter sensors, ECG (electrocardiogram) sensors, gene expression sensors, heart rate sensors, heart rate variability sensors, temperature sensors, stem cell activity sensors, and the like.

Such biomedical sensors may indicate in real time feedback information to the computer's logic circuit. In certain such embodiments, the logic circuit is responsive to signals from the various sensors system having tunable dynamic response characteristics in real time.

The logic circuit may thus provide closed-loop in real time monitoring the individual patient's vitals and or providing a tailored tunable (customized) dynamic response adjustment of various parameters of the applied ULF stimulation therapy to optimize the treatment schedule for enhancement therapy and complete treatment schedule for the individual patient. This is an object of the invention.

As an option a frequency generator apparatus may connect to a cell phone and or other suitable transmitter to monitor in real time the human patient's treatment status such as in an emergency.

The current invention encompasses that the apparatuses and methods may as an option employ a frequency amplifier that provides the frequency measurements, such as with an oscilloscope measurement/reading and or indicating apparatus.

The current invention encompasses that the apparatuses and methods may as an option employ a spectrum analyzer.

The current invention encompasses that the apparatuses and methods may as an option employ a wide variety of signal processing methods and apparatuses not specifically described herein.

Frequency Amplifiers

In several specified embodiments, the current invention apparatuses and methods encompass employing a variety of amplifier systems for the frequency generation having the criteria (parameters) of being able to accurately amplify the narrow and specific 0.6180 Hz sine wave to maintain a narrow and specific window of frequency variance (accuracy) within 0.0001 Hz or more specific as administered during the 15 minute exposure sessions within a complete treatment schedule.

The current invention encompasses employing any suitable ultra-low frequency amplifier, that may be modified to accurately amplify the continuous sine wave frequency of 0.6180 Hz with a variance (accuracy) of 0.0001 Hz, or more precise, during the 15-minute exposure sessions, preferably within a compete treatment schedule, or as needed.

In several specified embodiments encompasses in an apparatus aspect that encompasses sufficiently accurate ULF amplifying device (at 0.6180 Hz continuously maintaining a narrow and specific window of frequency variance (accuracy) within 0.0001 Hz or more specific as disclosed herein as needed during the preferred 15-minute exposure sessions), also known as ultra-precise amplifier such as but not limited to the following: the 2555A Precision AC/DC 100A Current Calibrator Transconductance Amplifier made available from Valhalla Scientific, the NPC120SG High Performance Piezo Stack Amplifier and the NPC300DIG Single Channel 330 mA High Performance Piezo Stack Amplifier made available from Newport, the P3000 Precision Series Power Amplifier made available from Electro-Voice, the MAX40100 Precision, Low-Power and Low-Noise OP Amp made available from Maxim Integrated, the LT1115 Ultra-Low Noise, Low Distortion, Audio OP Amp made available from Linear Technology, the AD797 Ultra-Low Distortion, Ultra-Low Noise OP Amp made available from Analog Devices, the ISL28134 Ultra-Low Noise, Zero Drift Rail to Rail Precision OP Amp available from Intersil, and the like.

As an option the frequency generation and or amplifier system may employ an inline filter system to mitigate (cancel/filter) interfering and or undesirable interference frequencies, such as but not limited to a high pass filter system to filter out interference frequencies above and or below 0.6180 Hz.

In an exemplary embodiment encompasses that the current invention an analog amplifier is preferred for amplifying the ULF 0.6180 Hz frequency therapy treatment to a human patient producing and maintaining an accurate sine wave.

In a specified embodiment encompasses that the current invention a digital amplifier is preferred for amplifying the ULF 0.6180 Hz frequency therapy treatment to a human patient producing and maintaining an accurate saw tooth wave.

In several specified embodiments, the current invention encompasses employing a variety of electrical signal cables (Interconnects) and or driver cables for transmitting the 0.6180 Hz sine wave signal within the specified criteria and or accurate parameters as required as disclosed herein.

In several embodiments, the predetermined total system watt utilization is a watt density of at least about 5 watts. The predetermined total ULF system power watt density in exemplary embodiments is typically selected from the range of about 5 watts to about 100 watts, preferably from about 5 watts to about 40 watts. In some embodiments, watts above and or below these values may be used.

As an example to deliver the predetermined dosage watts at the energy level and or dose(s) of the patient's tissue or tissues, a required, relatively greater wattage of the ULF therapy stimulation energy is calculated taking into account attenuation of the ULF stimulation therapy energy as it systemically travels, passing from the skin surface through various tissues including, muscle, fat, bone and or brain tissue. Factors known to affect the ULF penetration at the location of the affected regions, particularly the weight, size, depth, volume of the area to be frequency treated by ULF stimulation therapy are taken into account as needed.

In a prophetic example the inventors theorize that since the ULF administered power level is so small, there is no need for additional safety systems for the operator(s) and or practitioner(s).

In a prophetic example the inventors theorize that continuous unshielded exposure to an administered power level of about 10 watts could be detrimental to a human operator(s) and or practitioner(s), however all the ULF systems which administer up to 10 watts of power are shielded. If the ULF administered power were to increase above 100 watts; the operator(s) and or practitioner(s) would need to be suitably frequency shielded.

In a prophetic example, the inventors theorize that the patient's tissue and or tissues attenuation characteristics are a distance and density dependent relationship, of the cellular structure; i.e. not all cells are the same distance away from the source, so therefore they will take a little longer dose and or time. As an example, the ones that are closest will vibrate the most accurate; the ones that are farther away will vibrate at a distance and tissue density phase difference from the administered sine wave frequency characteristics.

As a further example bone is denser then skin, skin is more dense than internal organs, internal organs are more dense density than blood, blood is less dense than plasma. All of those density differences alter the effectiveness of the 0.6180 Hz sine wave administration to the patient. Additionally, the inventors theorize that the ULF therapy administers the 0.6180 Hz frequency as a sine wave, and the administered sine wave encounters frequency attenuating resistance from all of those cells and tissues in a density dependent manner; i.e. the more dense, the more resistance, and the ULF sine wave frequency administration further depends upon the harmonics of the 0.6180 Hz frequency to provide significant beneficial effects on the patient's cellular structures, further including sub-cellular structures.

For example, to obtain a desired wattage adjustments are made in wattage applied depending on human patient characteristics, such as but not limited to weight tissue depth, and the amount and or content of any intervening tissues. The ULF energy may have a predetermined wattage range at the subdermal tissue. It is theorized by the inventor that systemic ULF stimulation of tissue is most effective when exposing with watts of FST 0.6180 Hz of emitted power ranging between about 0.01 to 10 watts and a patient absorbed power of ranging between about 0.001 to 1 watts (note about ¹⁄₁₀th of emitted power is absorbed). In some embodiments, the watt range is selected up to about 100 watts depending upon clinical application and or desired performance.

In certain embodiments, wattage above and or below these values may be adjusted as needed.

The inventors theorize that these watt ranges are especially effective at producing/inducing the desired systemic ULF bio-stimulative effects for systemic human repair and enhancement, including stimulating production of new enhanced stem cells having enhanced secretions, further including stimulating the patient's cells and tissues to be healthier, stronger and more functionally effective.

In other specified embodiments, lower power (watts) are used to generate the desired effects locally on the patient's targeted tissue(s) such as when employing the transportable frequency emitting pistol, reference FIG. 9, wherein the wave guide frequency emitting pistol apparatus of the current invention administers a 0.6180 Hz sine wave frequency at a power ranging between about 0.01 watts to about 2 watts, preferably about 1 watt, depending upon the distance between the emitting surface and the patient (inverse square).

Frequency Emitter Systems

In several embodiments, the current invention encompasses employing any suitable frequency emitter system that accurately produces the narrow and specific 0.6180 Hz sine wave frequency and continuously maintaining a narrow and specific window of variance (accuracy) of 0.0001 Hz or more specific as disclosed herein and administering the preferred parameters and or criteria as defined herein, such as but not limited to, wave form, preferred power (watts) duration, and the like. Reference FIGS. 6, 7, 8, 9, 10, 11, 12, 13, 14.

In a preferred ULF frequency emitter system encompasses administering a complete ultra-low frequency therapy treatment schedule administering the narrow and specific 0.6180 Hz continuous sine wave frequency therapy to a patient employing an antenna emitting system that ranges between about 4 inches to 14 feet from the patient's body, preferably ranging between about 1 foot to 5 feet.

In a preferred ULF frequency emitter system encompasses an antenna emitting apparatus for the administration of the narrow and specific 0.6180 Hz sine wave frequency having an emitted power of about 2 to 10 watts, preferably producing and maintaining an accurate continuous sine wave producing the narrow and specific window of frequency variance (accuracy) within 0.0001 Hz or more specific administered during the 15 minute exposure sessions preferably within a complete treatment schedule for ULF systemic repair and enhancement therapy as needed or desired in both immersion and or open air ULF applications of the current invention that is simplified for illustrative purposes. Note the antenna housing and or support system is not shown for illustrative purposes. The preferred length of the antenna system, down the C-axis from emitter source base to tip, is preferably between about 11.8 inches and 3 feet. The preferred angle of the antenna cone apex is 33 degrees providing a conical wave guide transmitter having wire/mesh transmitting materials made from wire and or mesh materials such as silver, copper, gold, and or their alloys, or other suitable electro-conductive wire mesh and or net materials configured into an expanding diamond shape.

The ULF emitter of other embodiments may also comprise antenna systems having power capacities outside of these preferred limits, including their exposure intensity.

In a preferred apparatus aspect, the current invention encompasses a frequency emitter antenna style for open air treatment sessions such as a treatment room, treatment pods, treatment capsules, frequency containment shells, in vitro culturing chamber, and the like, to accurately and sufficiently produce and transmit the ULF sine wave form of the current invention through the air medium. Reference FIG. 16, 17, 19, 20, 21, 22, 23, 24.

In a preferred apparatus aspect encompasses an immersible frequency emitter antenna for immersed patient water treatment environments such as the immersion tank and the like, to accurately and sufficiently produce and transmit the ULF sine wave form of the current invention transmitted (administered) to a patient through a water medium.

The current invention encompasses a single frequency generating source for administering the 0.6180 Hz sine wave therapy through multiple frequency emitting antenna systems.

The current invention preferably encompasses a single frequency generating source for administering the 0.6180 Hz sine wave therapy through a single frequency emitting antenna system.

Depending upon how much power (watts) is being transmitted through the antenna system, the antenna as an option may be smaller (shorter) as needed to achieve a similar effect, preferably having a length down the C-axis from cone apex to tip between about 11.8 inches and 3 feet.

In a preferred embodiment, the antenna length matches the distance that these antenna tips are from the patient, for example if the antenna is about 3 feet long (down the central axis), the antenna tip is preferably about 3 feet away from the patient, and if the antenna is about 11.8 inches away from the patient, then the antenna is preferably about 11.8 inches long (down the central axis).

Note the matching length of the antenna and the distance from the patient provides a preferred and optimized relationship (geometry) of the bisection of a wavelength on a larger scale (dosage/distance relationship).

In several specified embodiments the current invention encompasses a computer programmable rotary driver system encompassing having an adjustable RPM (revolutions per minute) range, and or having a different number of adjustable blades as needed, and or having adjustable prop pitches (angle) for optimizing the adjustable high SPL (sound pressure level) preferably in conjunction with an adjustable input and or output frequency regulating baffling system to obtain an optimized ULF therapy room enclosure having minimum preferred dimensions as disclosed herein for administering the narrow and specific 0.6180 Hz frequency therapy, preferably producing and maintaining an accurate continuous sine wave providing an emitted power ranging between about 1 to 100 watts, preferably emitting about 2 to 10 watts, and or having a narrow and specific window of frequency variance (accuracy) within 0.0001 Hz administered during the 15 minute exposure sessions within a complete treatment schedule for systemic ULF repair and enhancement therapy as needed or desired. Reference FIG. 6.

The current invention encompasses employing a TRW-17 Transducer (a rotary driver) that generates from 1 to 20 Hz and is available from Eminent Technologies at 255 East Palmer Street, Tallahassee, Fla. 32301. Reference FIG. 6. Note, is preferably modified as needed.

The current invention further encompasses ULF emitter systems such as but not limited to Ultra Low Frequency Table, Rotary Driver system (reference FIG. 6) Ultra Low Frequency generator, Ultra Low Frequency Pulse Generator. Ultra-low frequency driver Ultra Low Frequency Pulse Resonator, Electrostatic Loud Speaker (ESL) Panel, Ac2ated Sound®, Electromagnetic Driver systems, Acoustic Surface Technology, Antenna systems (reference FIG. 7), Piezoelectric Cantilever Beams (reference FIG. 8), Tesla ASTROD Device available from www.ElectroHerbalism.com, tesla coil systems, Ultra-low Frequency transducers, such as but not limited to underwater transducers, flextensional transducers, hydroacoustic, electromagnetic, and or active material-based drivers, and the like, Ultra Low Frequency Driver, pencil driver systems, leaf springs, and the like, provided that they meet the specific parameters and or criteria disclosed herein and or may be suitably modified to meet the disclosed parameters and or criteria herein.

In several specified embodiments encompasses an ultra-low frequency driver system having a preferred configuration of the frequency emitter/driver external enclosure having a stealth frequency reflecting exterior cabinet enclosure (not shown) for significantly reducing and or eliminating undesirable interference frequencies by reflecting the undesirable interfering frequencies away from the emitter system, further including frequency canceling cones, three legs (supporting), six legs, for accurately administering the narrow and specific 0.6180 Hz frequency preferably producing and maintaining an accurate continuous sine wave having an emitted power of about 2 watts or more, and having a narrow and specific window of frequency variance (accuracy) within 0.0001 Hz or more specific as needed during the 15 minute exposure sessions within a complete treatment schedule for ULF human repair and enhancement therapy.

In several specified embodiments the current invention encompasses a Piezoelectric Cantilever Beam ULF emitter system having components including clamping setup, proof mass, polymer beam, stopper, piezoelectric elements, supporting frame, supporting spacers. Reference FIG. 8.

The ULF emitting apparatus and method of certain embodiments preferably exposes the human patient's entire body including the frequency targeted area of the human patient, as illustrated in FIGS. 8, 15, 16, 17, 18, 19, 20, 21, 22, 23. In other embodiments, the ULF generating and emitting apparatus and method targets certain target areas for frequency therapy, reference FIGS. 9, 10, 11, 12, 13, 14.

In certain embodiments, at least a portion of the ULF emitting apparatus and method is within a frequency path from the FST generating source to the patient. In such embodiments, the ULF emitting apparatus and method is substantially transmissive within a narrow and specific continuous frequency of 0.6180 Hz, for the ULF targeting and or administration of the FST emitted by the output emission area of the frequency emitting system(s). Emitting ULF systems are further adapted to reduce interference reflections of the FST frequency. By reducing interference reflections, the ULF continuous emitting apparatus and method increases the dose of FST transmitted to the human patient and significantly improves the frequency absorption and or reduces the need to administer a higher watt dosage. In certain such embodiments, the ULF filtering apparatuses and methods reduces interference reflections that comprises one or more frequency filtering coatings, films, layers, membranes, etc. in the frequency path of the transmitted FST which are adapted to reduce interference frequency reflections.

The current invention encompasses administering the ULF therapy to the human patient(s) from a transportable hand held pistol frequency emitting apparatus, reference FIG. 9, and or transportable wristband frequency emitter apparatus, reference FIG. 12, so as to substantially reduce the distance (inverse square) between the patient and the ULF emitting apparatus in the ULF path of the narrow and specific 0.6180 Hz continuous frequency that would otherwise result in at least a portion of the FST propagating from the FST source to the human patient to be reflected back towards the ULF generating and emitting source.

In addition, certain embodiments of the ULF generating and emitting apparatus and method comprises a faraday interference frequency shielding apparatuses having suitable material for interference frequency canceling and or shielding characteristics for obtaining interference frequency shielding therein of wire formed in a mesh such as polypropylene and or metallic materials, such as silver, copper, gold, and or other suitable electro-conductive wire mesh materials having faraday frequency shielding and or canceling effects.

The current invention further reduces interference generated reflections between the ULF generating apparatus and the ULF emitting apparatus and further reducing interference reflection thereby improving accuracy of the corresponding absorption of the ULF generated and emitted therapy frequency.

Figure 3:
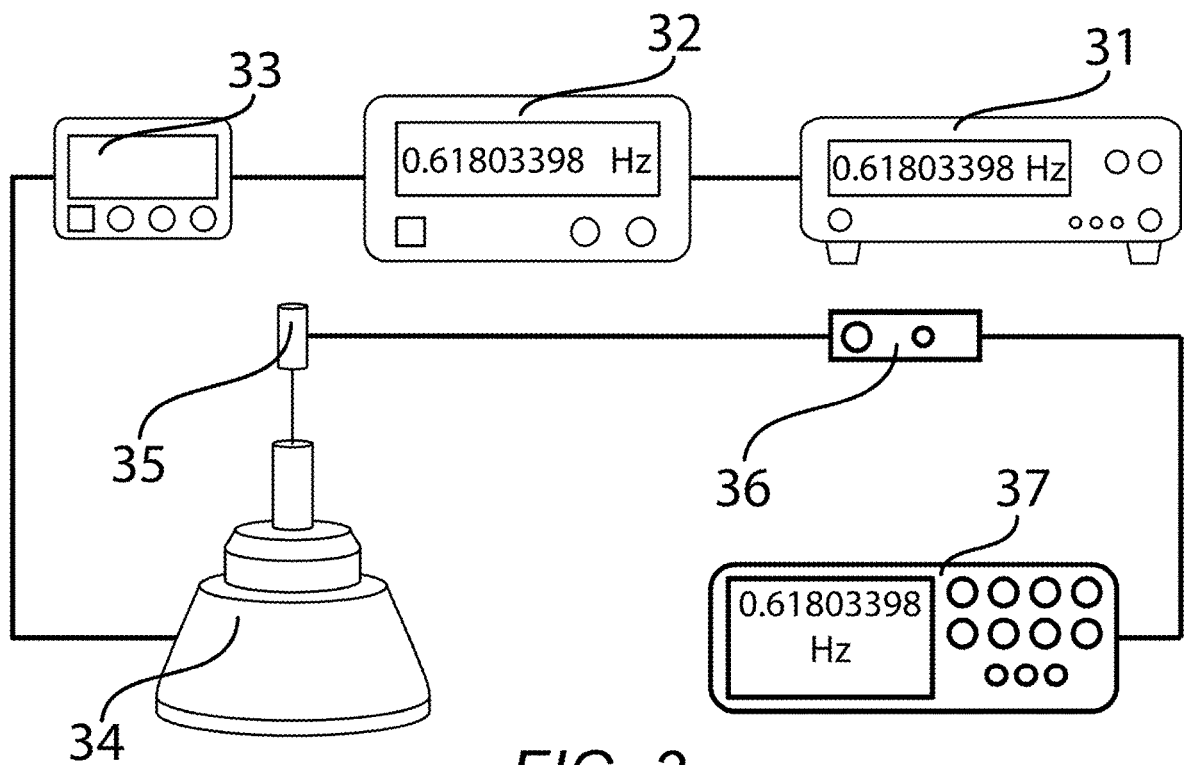
FIG. 3 illustrates one of many possible configurations of a schematic diagram of the ULF therapy having a 0.6180 Hz sine wave frequency emitter depicting the frequency generator 31, power amplifier 32, timer 33, one of many possible frequency emitter/resonator systems 34, further depicting ULF monitoring components including frequency sensor 35, signal amplifier 36, and or power sensors/monitor 37, and or optionally encompassing a safety mechanism (apparatus) to identify the authorized operator such as from scanning a finger, thumb, and or hand (palm), and or other suitable safety encoding mechanisms, for administering the narrow and specific 0.6180 Hz frequency, and emitting an accurate continuous sine wave, having an emitted ULF power ranging between about 0.01 to 10 watts, preferably about 5 watts, and or an absorbed power ranging between about 0.2 to 1 watts, preferably about 0.5 watts (note about 1/10th of emitted power is absorbed), and preferably emitting a narrow and specific window of frequency variance (accuracy) within 0.0001 Hz or more specific administered during the 15 minute exposure sessions (within a complete treatment schedule) for ULF genetic enhancement therapy as needed or desired.

The current invention encompasses employing monitors for indicating and or displaying the ULF energy administered to the human patient, reference FIG. 3 and FIG. 5, providing the ULF emitting apparatus and method distributing the ULF stimulation therapy energy preferably over the human patients entire body to be treated, thereby advantageously lowering the required wattage, to alter the total FST output distribution to reduce frequency inhomogeneity.

The current invention encompasses that accurate dosing of the ULF administration may be estimated from calculations and other experimentations for determining doses and or treatment schedules for individual patient.

The ULF emitting apparatuses' dosing is based upon calculations and is adapted to the positioning between the ULF generating source and the human patient's body.

In certain such embodiments, the ULF emitting apparatus and method is mechanically adjustable so as to accurately adjust the transmitting position and or power of the ULF wave guide emitting FST source relative to the human patient's body, reference FIG. 20. Other optional configurations of the frequency transmitting apparatus are compatible with embodiments described herein.

In certain embodiments, the ULF administration apparatus and method provides a reliable reusable interface between the FST emission apparatus and the patient. In such embodiments, the ULF human enhancement apparatus and method may be cleaned and or sterilized between uses particularly between uses by different human patients. In other embodiments, the ULF generating and emitting apparatus provides a reusable interface between the FST apparatus and the patient's body.

In certain such embodiments, the ULF stimulation emitting source physically moves the apparatus relative to the human patient, reference FIG. 20. In other embodiments, the apparatus and method does not move the ULF emitting source but redirects the emitted ULF stimulation to different locations. In an example embodiment, as illustrated in FIG. 20, the mechanized frequency emitter source mechanized positioning arm having vertical pivoting means and or horizontal pivoting means slides along the longitudinal railing down the length of the treatment bed for accurately adjusting the position of the frequency emitter source to administer the narrow and specific 0.6180 Hz continuous sine wave frequency from one of many possible frequency generator systems of the current invention.

In certain embodiments, the human patient is in a seated adjustable reclining position so as to position the human patient in a preferred pre-engineered proximity (distance) to the ULF stimulation source as described herein, to accurately administer the ULF therapy to a human patient's body including frequency targeted portions. This is an object of the invention.

The ULF emitter system(s) of the current invention is preferably removably coupled to a power supply, which in certain embodiments comprises a battery and or in other embodiments comprises an 50 Hz and or 60 Hz alternating current source. The FST frequency emitter wave guide is also removably coupled to the ULF generating and transmission source. An optional logic circuit is responsive to the signal from the timer or clock and or to the authorized operator's programmable input from the operator interface to transmit a control signal to the ULF emitting wave guide system. In response to the control signal from the logic circuit, the ULF emitting wave guide and frequency stimulation emitter adjusts and or controls the power applied to the ULF emitting stimulation source. Other control circuits besides the control circuit are compatible with embodiments described herein.

The ULF emitting apparatus optionally may encompass one or more temperature sensors (e.g., thermocouples, thermistors) which generate electrical signals indicative of the real-time temperature of the output ULF emitting apparatus and or other portions of the ULF generating and emitting device as needed (not shown).

Figure 2:
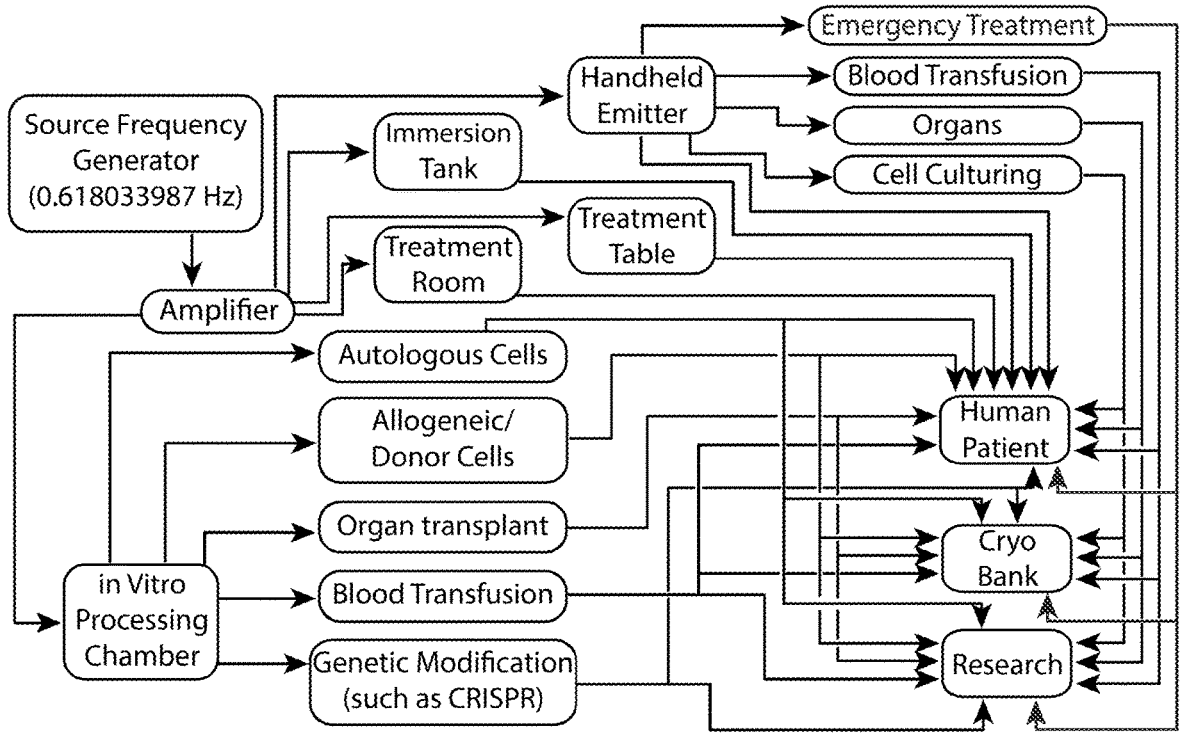
FIG. 2 illustrates a flow chart of the current invention's many possible ULF treatment schedule therapies methods and treatment apparatuses of the current invention.

In certain other embodiments, the output frequency emitting apparatus is rigid such as in an immersion tank, pod, frequency treatment capsule, containment shell, vibrating table, treatment room, hyperbaric chamber, that is sufficiently accurate and frequency transmissive at the 0.6180 Hz sine wave frequency to accurately and sufficiently transmit through the human patient's entire body, reference FIG. 1 and FIG. 2.

Vibration Isolation Mounts

In other preferred embodiments of the current invention, shown in FIGS. 18, 20 and 22, the ULF treatment system encompasses one of many possible configurations systems of the adjustable frequency isolator mount supporting structure. As seen in FIGS. 18, 20, and 22, the current invention interference frequency canceling and attenuating support mounts and or feet preferably conforms to the frequency treatment system's lateral dimensions, as an example.

The preferred isolating mount apparatus of the current invention is Failsafe EF RA 500 available from TRELLEBORG Industrial AVS, Mission Supply Mansfield, Tex. USA Tel: 817 453 1900 Fax: 817 453 0800 www.missionsupplyonline.com sales@missionsupplyonline.com.

Another preferred isolating apparatus for the ULF apparatuses of the current invention is Model Number ET5253 available from ITT Enidine Inc. 7 Centre Drive, Orchard Park, N.Y. 14127 Phone: 716-662-1900 Fax: 716-662-1909, Email: industrialsales@enidine.com, Email: aviationsales@enidine.com, www.enidine.com.

Additionally, the current invention further encompasses employing isolators, reference FIGS. 18, 20, and 22, that further contribute to "adjust" the interference frequency dampening effect of any undesirable and interfering frequencies to the administered 0.6180 Hz sine wave frequency to maintain the narrow and specific 0.0001 Hz window of frequency variance, and further reduce the undesirable amplitude peaks and to accurately spread the amplification due to improved resonance over a more accurate frequency spectrum as needed. As an option, further attenuation and canceling characteristics may be provided such that the apparatuses In a specified embodiment, the current invention may encompass modifying/retrofitting any suitable vibration isolating apparatuses as known within the art.

The current invention encompasses employing adjustable interference frequency canceling and or dampening baffling system as needed to maintain the accurate narrow and specific administration of the 0.6180 Hz sine wave frequency administration.

Vibration Canceling Cones

In several specified embodiments, the current invention encompasses methods and apparatuses for the attenuation and canceling of undesirable (interfering) frequencies from the employment of the symbiotic cooperation of isolation cones and receiving pedestals (reference FIGS. 15, 18, and 20), as stated in the current invention, and their undesirable frequency attenuation and canceling characteristics in conjunction with the current invention frequency canceling characteristics, comprised of metal and or other suitable wave/frequency canceling materials, and preferably being paired, such as having four to eight cones or more depending upon the supporting frame system, preferably accurately positioned near the ultra-low frequency ULF generator, amplifier, and or emitter of the current invention.

In several specified embodiments, the current invention encompasses that the frequency canceling methods and apparatuses in the form of inventive interference frequency canceling cones apparatuses may be mounted onto any apparatus as disclosed herein, reference FIGS. 15, 18, and 20.

The ULF apparatus is preferably mounted on a interference frequency canceling isolation framework or foundation, preferably as generally depicted in FIGS. 15, 18, and 20, having a series of inverted interference frequency canceling cones and the receiving pedestals that supports and attenuates and cancels interfering frequencies that are encountered during the inventive process and operations of a complete ULF treatment schedule therapy, such as canceling a variety of proximate interfering frequencies such as encountered from generators, amplifiers, etc., further including canceling pneumatic vibrating actions from the ULF emitter system vibrator and the supporting members, which contribute to the isolation of the motion of the base. Preferably, four or more such dimensionally positioned isolation support systems are preferred and configured, as needed. Four such isolation supports are most preferred.

The vibration canceling cone systems are preferably positioned and installed near the ultra-low frequency antennas/emitters, and may further be employed with additional adjustable baffling systems and or other isolation systems.

In other exemplary embodiments, the current invention encompasses a method and apparatus for attenuating and canceling a wide of undesirable frequencies above and below 0.6180 Hz preferably by employing two or more right side up (not shown) and two or more inverted (upside down) frequency attenuating and canceling metallic canceling cones, with the inverted cones preferably employing frequency receiving canceling pedestals.

In a specified embodiment, the current invention encompasses, in a method aspect, that the frequency attenuating and canceling inverted (upside down) cones, preferably having a corresponding undesired frequency-canceling receiving pedestal or pedestals as needed (reference FIGS. 15, 18, and 20).

In other specified embodiments, the current invention encompasses apparatuses and methods preferably having mounted interference frequency attenuating and canceling characteristics, in the form of a series of metallic cones as frequency attenuating and canceling systems, further including securing on their preferred pre-engineered locations on any of the ULF apparatuses of the current invention.

In several specified embodiments, the current invention encompasses, in an apparatus aspect, having a wide variety of interference frequency attenuating and canceling characteristics, preferably in the form of metallic cones having a supersonic or subsonic configuration, preferably having right side up (not shown) and/or inverted (upside down) placement and mounting as illustrated in FIGS. 15, 18 and 20. Note supersonic cone configurations are most preferred.

In other exemplary embodiments the current invention encompasses that the frequency canceling cones may include sonic, supersonic, and pyramid configurations scaled and configured, as needed, for capturing and eliminating any undesirable or encountered interfering frequency and waves (frequencies) by capturing and attenuating those interfering frequencies and, for all practical purposes, (virtually) canceling the interfering, waves and frequencies, further including the synergistic cones' corresponding receiving pedestals. The symbiotic combination of the preferred super-sonic cone configurations and their interference frequency canceling receiving pedestals is most preferred (reference FIGS. 15, 18 and 20). Sonic and supersonic, cones are most preferred.

Frequency Emitting Pistol

In some embodiments, a single stimulating emergency targeted treatment site is frequency stimulated, such as in emergency ULF administration environment employing a transportable hand held style pistol frequency emitting wave guide apparatus of the current invention, reference FIG. 9. In some embodiments, the specific emergency targeted treatment site is selected from the group consisting of heart, head, lungs, liver, pancreas, kidney, spleen, intestine, bones, bone marrow, skeletal or smooth muscle, skin, and the like, and or combinations thereof.

In several specified embodiments the current invention encompasses a programmable transportable hand held wave guide pistol that encompasses an on/off switch, frequency indicating window, wave form indicating window, power sources such as battery, power cord, power pack, etc., and or further including safety mechanisms (apparatus) that identifies the authorized operator by scanning a thumb, finger, and or palm, and or other suitable safety encoding mechanism, for controllably emitting the narrow and specific frequency of 0.6180 Hz having a narrow and specific window of frequency variance (accuracy) within 0.0001 Hz or more specific to a human patient as needed during a 15 minute exposure sessions preferably within a complete treatment schedule for ULF emergency repair and enhancement therapy as needed or desired, to controllably expose at least one predetermined area of a human patient's body to the ULF emergency therapy, reference FIG. 9.

In still other embodiments, the transportable hand held emergency therapy delivery apparatus and method for administering the ULF emergency stimulation therapy, as an example includes a handheld pistol frequency administering apparatus and method, as illustrated in FIG. 9. The handheld apparatus includes a ULF stimulation source and a ULF generating apparatus.

The transportable light weight pistol ULF emitter system is easily transported and may be employed for emergency onsite administration to a patient of an emergency ULF treatment schedule such as in an ambulance, a rescue helicopter or vehicle, a gurney, stretcher and or rescue basket, and the like. Reference FIGS. 9 and 23.

In an exemplary embodiment, the current invention encompasses as a variation of the invention that the handheld wave guide ULF emitting pistol apparatus may be employed during a wide variety of transplanting processes, procedures and or therapies.

In certain other embodiments, the human patient's body is not contacted by either the wave guide source and or an intervening apparatus.

Note the preferred administered power range for the pistol wave guide ULF emitter system ranges between about 0.01 watts to about 2 watts.

Note the preferred distance from the pistol wave guide ULF emitter system to the patient ranges between about 1 to 5 inches.

Frequency Emitting Epidermal Patch

The current invention encompasses administering a complete ULF treatment schedule from at least one removable and or reusable transportable epidermal patch ULF emitter apparatus and system, reference FIG. 11, attached to a patient (may be attached to anywhere on the patient), having many possible epidermal patch emitter systems configurations, including circular and square, and further encompassing an 0.6180 Hz sine wave micro-emitting apparatus, further encompassing an attachment cable having a cable attachment terminal connected to the frequency generating system and or amplifier system. Note the preferred power range for the epidermal patch emitter system ranges between about 0.01 watts to about 1 watt.

Frequency Emitting Wristband

In several specified embodiments the apparatuses and methods of the current invention encompasses frequency administration from a transportable wrist attachment terminal ULF emitting apparatuses, having an anode on one and a cathode on the other, that may be removably attached to the human patients wrists such as with Velcro®, as a frequency emitter transmitting source for administering the narrow and specific 0.6180 Hz frequency, preferably producing and maintaining an accurate continuous sine wave, or optional saw tooth wave, continuously maintaining the narrow and specific window of frequency variance (accuracy) within 0.0001 Hz or more specific as needed during the 15 minute exposure sessions preferably within a complete treatment schedule for ULF disease suppression and or to obtain complete disease remission and or enhancement therapy as disclosed herein by administering an emitted power ranging between about 0.01 watts to about 2 watts. Continuous sine wave is most preferred.

The current invention encompasses adjustable frequency emitting wearable terminals that may be positioned and or removably secured on the human patient's wrists, feet, arms, ankles, chest, head, and the like as some of many possible attachment locations, to administer the ULF therapy locally and or systemically through the human patient's entire body, reference FIG. 12.

In several specified embodiments the current inventions apparatuses and methods encompass a removable, reusable, transportable wristband reference FIG. 12 for ULF transmitting (emitting) surface being composed of electro-conductive materials such as but not limited to gold, silver, stainless steel, nickel, and the like, and or other suitable alloys, for targeted and or systemic frequency therapy applications.

The adjustable removable secured wrist straps, reference FIG. 12, are preferably fabricated from an elastomeric material to which is secured to a patient by any suitable securing means, such as mating Velcro strips, snaps, hooks, buttons, ties, and the like. Alternatively, the adjustable wrist hand/strap is a loop of elastomeric material sized appropriately to fit snugly over a particular patients body parts, such as a particular patient's wrists, arms and or legs, and or optionally removably secured around the human patient's chest and or head. The precise configuration of the strap is subject only to the limitation that the transmitting surface is capable of accurately transmitting the ULF generating and emitting ULF stimulation sources in a preselected secured position on the patient's body. In any case, the frequency stimulation transmitting sources are secured to the strap so that when the strap is positioned on the patient's body parts, the frequency stimulation emitting source is positioned in direct contact with the patient's skin so that the ULF of 0.6180 Hz sine wave frequency stimulation emitted by the ULF emitting source(s) is in directed contact to the patient's skin surface over which the device is secured. Various strap configurations and the optional spatial distributions of the ULF emission sources are contemplated so that the ULF generating and emitting frequency administering device can be adapted to treat different tissues including different damaged areas of the patient's body.

In some embodiments, a strap is not used and instead the ULF stimulation emitting source is removably attachable onto a patient thereby holding the ULF emitting source in position as needed. The removably attached adjustable straps is preferably constructed of a stretchable fabric and or mesh comprising materials such as Lycra and or nylon, and the like.

If filters, dispersion gratings, and or any other material lies between the FST frequency source and the patient's skin, any absorption or dispersion of the frequency stimulation energy by such material should be taken into account and the applied FST frequency therapy energy adjusted, if needed, to account for the material(s).

The ULF administration apparatus and method further comprises placing a removably wearable ULF wristband emitter apparatus (or other treatment site) in an operational block. The apparatus comprises a housing and a transmitting (emitting) apparatus. Each transmitting (emitting) apparatus encompasses a first portion which conforms to a corresponding portion of the patient's body when the apparatus is worn by the patient. The apparatus also encompasses a second portion which connects to the frequency generating device when the frequency generating device contacts the ULF emitting apparatus. The apparatus is substantially transmissive to the continuous sine wave ULF of 0.6180 Hz transmitted by the ULF generating device. Other configurations of the adjustable wearable transmitting apparatuses and method depicted in FIG. 12 are also conceivable and compatible with certain embodiments described herein.

Probe Emitter System

The current invention encompasses many possible configurations of a programmable transportable hand held frequency wave guide emitting probe, reference FIG. 10, that encompasses an on/off switch, a frequency indicating display, many possible adjustment controls, a battery power source, handle and further includes optional safety mechanisms (apparatus) that identifies the authorized operator(s) and or practitioner(s) by scanning a thumb, finger, and or hand (palm), and or other suitable safety encoding mechanism, for controlling dosage and administering the narrow and specific 0.6180 Hz sine wave frequency producing a narrow and specific window of frequency variance (accuracy) within 0.0001 Hz administered through the frequency emitting probe, producing a narrow and specific window of frequency variance (accuracy) within 0.0001 Hz administered during a complete ULF treatment schedule emitting an administered power ranging between about 0.01 watts and 2 watts, including a 15 minute emergency treatment exposure session, preferably having a resting and testing period (pause time) of about 3 to 5 hours between exposure sessions, for repair and enhancement therapy, to controllably expose at least one predetermined area of a human patient's body to the ULF stimulation therapy for targeted treatment such as vagina, rectum, open wound, and the like. The probe emitter system encompasses a diameter of about 25 mm (1 inch) and a length of about 300 mm (12 inches).

Immersion Tank Therapy

In several specified embodiments, the current invention apparatuses and methods encompasses a human patient receiving ULF therapy in a variety of suitable immersion tanks, reference FIG. 15, of the current invention having adjusted temperature and or salinity regulated water, further including a frequency generator, a ULF emitter system, power cord, amplifier, and an optional human patient supporting harness (not shown). The immersion tank apparatus of the current invention encompasses a frequency dampening ring and or base supporting collar system around the base, and or a frequency dampening ring system around the upper edge of the immersion tank. The immersion tank apparatus further encompasses faraday cage shielding characteristics employing electro-conductive wire net/mesh configured materials as needed to achieve the required faraday interference frequency shielding effects for accurately administering to the patient the narrow and specific 0.6180 Hz frequency continuously maintaining a narrow and specific window of frequency variance (accuracy) within 0.0001 Hz or more specific as disclosed herein as needed during the 15 minute exposure sessions and complete treatment schedules, while further producing previously unavailable safety in the field of human enhancement.

The apparatus and method further comprises a water immersion tank frequency therapy system in an operational block. The apparatus comprises a housing (body), a coupled generator system and or amplifier system, a monitoring/feedback system, and at least one water immersible antenna frequency emitting apparatus, reference FIG. 7.

The water tank immersion apparatus also encompasses the frequency generating device, the monitoring computer controlling system, and or the emitting antenna system being integrated within the immersion tank apparatus.

The ULF antenna emitting apparatus is substantially transmissive to the FST frequency transmitted by the frequency generating device. Other configurations of the water immersion tank than depicted in FIG. 15 are also conceivable and compatible with certain embodiments described herein for transmitting the ULF treatment to a patient through water.

In a preferred ULF immersion tank system encompasses at least one immersible antenna emitting apparatus for the administration of the narrow and specific 0.6180 Hz sine wave frequency having an emitted power of between about 5 to 10 watts (total for each antenna).

In a more preferred embodiment, the ULF immersion tank system comprises six different antennas surrounding the patient's body in the immersion tank at a pre-defined and adjustable distance from the patient of between about 1 feet to 5 feet, preferably about 3 feet depending upon the power that is administered.

As an option, the antenna length should match the distance that this antenna is from the patient, for example if the antenna is 3 feet long (down the central axis), preferably the tip needs to be 3 feet away from the patient, and if the antenna is 11.8 inches away from the patient, then the antenna can be 11.8 inches long, down the central axis.

In a preferred embodiment, the ULF administration apparatus and method encompasses a human patient being fully or partially immersed in a water immersion therapy tank containing adjusted salt water content providing optimized systemic ULF administration.

In certain embodiments, the ULF water immersible antenna emitting source is disposed on the interior surface of the water immersion tank and or containment chamber, reference FIG. 15, and holds the ULF antenna emitting apparatus in a water containment apparatus that is adapted to be removably coupled to the inside of the water immersion tank system, reference FIG. 15, such that the ULF antenna emitting output emission surface area may be advantageously placed in a selected position for systemic and or localized frequency treatments. In other embodiments, the ULF generating and emitting FST source, reference FIG. 7, may be an integral portion of the patient water immersion tank apparatus.

The apparatus and method further comprises placing the water immersible frequency emitting antenna apparatus, reference FIG. 7, within direct contact with the water immersion tank apparatus for the human patient's ULF administration therapy in an operational block. The water immersion tank apparatus and method further comprises frequency stimulating with FST frequency apparatus emitted by the frequency stimulation antenna emitting apparatus, reference FIG. 7.

The water immersion tank therapy apparatus and method encompasses employing one of any number of ULF antenna and or driver emitter systems such as but not limited to Electrostatic Loud Speaker (ESL) Panel, Ac2ated Sound®, Electromagnetic Driver system, Acoustic Surface Technology, immersible Antenna systems, Ultra-low Frequency transducers, such as but not limited to underwater transducers, flextensional transducers, hydroacoustic, and the like for the ULF to be accurately transmitted through the water and the patient.

In a preferred embodiment, the current invention preferably encompasses the water immersion tank therapy system encompasses an adjusted water temperature ranging between about 30.6 to 33.9 C/87 to 93 F.

In a preferred embodiment, the current invention encompasses the water immersion tank therapy system encompasses that the water having an adjusted pH range of about 7.4.

The immersion tank system complete treatment schedule timing and therapeutic window encompasses administering the ULF treatment schedule to a human patient in an immersion tank, and having the patient be exposed to the sine wave frequency of 0.61803 Hz for about 15 minutes, three times per 24 hours, preferably having a resting and testing period (pause time) of between about 3 to 5 hours between individual exposure session, with an administered power of ranging between about 2 to 10 watts depending upon the individual patient weight that may be adjusted as needed on a case-by-case basis, and or tailored to the patient for administering ULF to a patient for suppression and or complete remission from a disease or condition and or systemic enhancement therapy.

In certain specified embodiments, preparing the ULF emitting apparatus comprises cleaning the emitting surface portion of the ULF emitting apparatus through which the generated ULF is outputted.

In certain embodiments, calibrating the ULF emitting apparatus comprises verifying a watt range calibration of the ULF outputted from the ULF emitting apparatus. Such verification preferably comprises measuring the ULF, and or wave form, and or watt output measured in real time from the frequency emitting apparatus, and comparing the measured intensity to the expected frequency and wave form and or the pre-programmed watt intensity level, and making adjustments as needed.

Treatment Pod

In several specified embodiments the current invention encompasses ULF generating and emitting treatment pod, for administering a complete ULF treatment schedule emitting a 0.6180 Hz continuous sine wave having an emitted adjustable power ranging between about 2 watts and 10 watts reference FIGS. 16 and 17, having a faraday dome covered pod in an open and or closed position encompasses a interference frequency baffle regulating system forming a seat that may be enclosed by an elongated oval wave guide faraday regulating covering system having frequency interference frequency dampening, canceling and or shielding characteristics, further illustrating a large transparent domed canopy for frequency shielding the wave guide window formed therein made of wire mesh net shielding materials such as polypropylene and or metallic wire frequency dampening and or shielding materials, such as silver, copper, gold, and or other suitable electro-conductive wire mesh and or net materials. The bottom of the front of the domed shaped canopy lid or door is pivotally attached to the front of the base by hinged assembly and may be locked in the open position on the base by a plurality of latches that are conjointly operated by an external lever and or an internal lever.

The weight of the wave guide extending canopy dome upon opening is borne by a pair of optional side gas or spring struts wherein the diameter of the polypropylene domed interference frequency shielding wall permits a human patient to sit within the frequency treatment chamber for administering (generating and emitting) the narrow and specific 0.6180 Hz sine wave frequency continuously maintaining the narrow and specific window of frequency variance (accuracy) within 0.0001 Hz or more specific during the 15 minute exposure sessions (complete treatment schedule) for ULF disease suppression and or elimination, and enhancement therapy as needed, and further permits the polypropylene and or wire mesh frequency interference shielding dome chamber cover to be transportable and to fit through a standard double door opening in a direction perpendicular to the axis of the wall, reference FIGS. 16 and 17.

The dome treatment pod of the current invention, reference FIGS. 16 and 17, encompasses an ability to optimize and or regulate adjusting the o2 percentage within the therapy pod chamber preferably ranging between 19.5 to 23.5%, further regulating the chamber pod and or patient's temperature to optimize the complete treatment schedule ULF therapy such as in an emergency situation and or a patient in ultra-critical condition.

In several specified embodiments, the current invention encompasses a domed frequency treatment pod chamber having components of the pod's door hinge, a seat for the human patient, the driver/frequency emitter, the platform, having input and or output frequency canceling baffles, one of many possible pre-programmed computer controllers for programming (selecting) the frequency, wave form, dose, etc. (treatment schedules), and or monitoring the patient's vitals.

The current invention encompasses that the ULF treatment pod's system is preferably adjustable (selectable) between the two or more pre-programmed treatment schedule settings having, for example, one preprogrammed treatment schedule administered for prophylaxis from a wide variety conditions and or diseases, and a second preprogrammed treatment schedule for administering ULF therapy for suppression and or complete remission from a wide variety of disorders, conditions, and or diseases, or adjusted as needed, further including an optional customized treatment schedule.

Frequency Vibrating Table Therapy

In several specified embodiments, the apparatuses and methods of the current invention encompasses an ULF treatment table system or apparatus for administering a complete ULF treatment schedule emitting a 0.6180 Hz continuous sine wave having an emitted adjustable power ranging between about 0.01 watts and 5 watts for systemically treating a human patient's body (it shall be appreciated that other frequency targeted tissues are also treated), reference FIG. 18. The frequency table treatment therapy apparatus comprises a ULF generator that is simplified for illustrative purposes encompasses frequency regulating input and or output frequency regulating baffles forming a platform for the patient to lie down upon that is enclosed by a frequency regulating wave guide system that further encompasses interference frequency dampening characteristics and or faraday shielding (not shown), may optionally encompass a faraday frequency shielding enclosure (not shown) formed therein and made of suitable materials such as polypropylene having wire dampening mesh and or net frequency shielding materials, such as silver, copper, gold, and or other suitable electro-conductive wire mesh and or net embedded materials as needed to achieve the preferred faraday interference frequency shielding dampening and canceling effects. The ULF treatment vibrating table further encompasses one of many possible configurations of the invention's amplifiers, and or computer controlled device for programming the frequency therapy and optimizing and or monitoring the patient's vitals and other biometrics, including a safety mechanism (apparatus) to identify the authorized operator such as by scanning a thumb, finger, and or hand (palm), and or other suitable safety encoding mechanisms, for accurately controlling the frequency emitter source for administering the narrow and specific 0.6180 Hz frequency having a narrow and specific window of frequency variance (accuracy) within 0.0001 Hz or more specific during the 15 minute exposure sessions (and a complete treatment schedule) for administering to a patient ULF prophylaxis, repair and or enhancement therapy, reference FIG. 18.

The current invention encompasses a ULF treatment vibrating table system having two or more programmable settings (treatment schedules) one pre-programmed setting for treating a wide variety of diseases, conditions, and or injuries, and a second pre-programmed treatment schedule setting for systemic human enhancement, including genetic repair and enhancement.

The current invention further encompasses a frequency stimulation vibrating table system's ability to optimize and or regulate o2 percentage in the frequency stimulation therapy chamber to optimize the frequency therapy such as in an emergency situation and or a patient in ultra-critical condition adjusted between 19.5 to 23.5%, as well as further optimizing the temperature.

Frequency Containment Shell

In several specified embodiments the apparatuses and methods of the current invention encompass one of many possible configurations of a ULF treatment therapy emitting containment shielding shell system, reference FIG. 19, having a slidably chamber door, that encompasses ULF input and or output tunable frequency canceling baffle system composing a platform, further depicting an adjustable patient bed and an enclosed capsule faraday containment shell having a wave guide regulating system further encompassing dampening characteristics for interference frequency canceling formed therein and made of suitable materials such as polypropylene dampening and or wire frequency shielding materials, preferably from silver, copper, gold, and or other suitable alloys and or other electro-conductive wire mesh and or net materials as needed to achieve the needed interference frequency canceling characteristics including frequency dampening effects. The patient lies within the frequency emitting containment shell having a ULF emitter system administering the narrow and specific 0.6180 Hz frequency preferably producing and maintaining an accurate continuous sine wave having an adjustable total power utilization range between about 5 to 40 watts, and having an emitted adjustable power ranging between about 2 watts and 10 watts and having a narrow and specific window of frequency variance (accuracy) within 0.0001 Hz or more specific as disclosed herein during the 15 minute exposure sessions within a complete treatment schedule administered for disease suppression and or remission including systemic repair and human enhancement. The ULF emitting frequency therapy treatment containment shell system further permits the polypropylene frequency interference frequency shielding containment shell to be transportable and fit through a standard double door. Reference FIG. 19.

The current invention further encompasses the treatment containment shell's, reference FIG. 19, ability to optimize and or regulate oxygen percentage inside the therapy chamber ranging between about 19.5 to 23.5%, as well as further optimizing (regulating) the pod's internal temperature to optimize the ULF treatment schedules for patients in critical to ultra-critical conditions, such as but not limited to life threatening emergencies such as burns, infections, and or radiation poisoning.

Frequency Treatment Capsule

In several specified embodiments the current invention apparatuses and methods encompasses an accurate sealable ULF emitting treatment capsule, reference FIG. 20, encompassing frequency input and or output frequency interference regulating baffle system forming a supporting platform for the patient to lie down in that may be enclosed by an elongated capsule frequency wave guide regulating system, further encompassing a stabilizing and interference frequency dampening and or canceling platform, having interference frequency canceling and or faraday shielding characteristics, encompassing a large faraday frequency shielding transparent domed capsule wave guiding cover window formed therein made of suitable materials such as polypropylene encasing frequency dampening and or shielding wire mesh and or net materials, such as silver, copper, gold, and or other suitable electro-conductive wire mesh and or net shielding materials as needed to achieve the needed faraday frequency interference shielding, dampening, and or canceling effects, and further depicts having a mechanized frequency emitter source having adjustable positioning having vertical arm pivoting means and or horizontal pivoting means, further including roll, pitch and or yaw positioning means that slides along the longitudinal railing down the length of the treatment bed for accurately adjusting the position and dosage of the frequency emitter source for administering to a patient the narrow and specific sine wave 0.6180 Hz frequency continuously maintaining the narrow and specific window of frequency variance (accuracy) preferably within 0.0001 Hz or more specific as needed during the 15 minute exposure sessions (and complete treatment schedules) for ULF disease suppression and or complete remission therapy and or enhancement as needed or desired.

The current invention apparatuses and methods further encompasses the ULF treatment capsule's, reference FIG. 20, ability to optimize and or regulate o2 percentage in the chamber, ranging between 19.5 to 23.5%, as well as further adjusting the temperature as needed to optimize the frequency therapy such as in an emergency situation and or for treating a patient in an ultra-critical condition.

The ULF treatment capsules encompasses one of many possible configurations of an amplifier, a computer-controlling device for programming the patient's treatment schedule watts, exposure time, resting periods frequency and generating the ULF therapy and or optimizing and or monitoring the patient's vitals and other biometrics, including a safety mechanism (apparatus) to identify the authorized operator such as by scanning a thumb, finger, palm (hand), and or other safety encoding mechanisms.

Treatment Rooms and Chambers

The inventors theorize that the patient's frequency stimulated therapeutic field effect (exposure) having a narrow and specific accurate window of frequency variance of 0.0001 Hz or more specific as disclosed herein during the preferred 15 minute exposure sessions within a complete treatment schedule having a sine wave frequency of 0.6180 Hz that preferably is between about 0.5 meters (1.64 feet) to 1.2 meters (4 feet) from the patient's body, and most preferably about 0.91 meters (3 feet) from the patient's body.

In several specified embodiments the current invention encompasses apparatuses and methods for an isolated faraday cage ULF treatment room or treatment chamber having one or more human patients sitting in chairs and preferred being exposed to the continuous sine wave frequency ULF of 0.6180 Hz preferably having a sine wave form, and having frequency canceling baffle system and or interference frequency dampening characteristics to continuously maintain the necessary and required narrow and specific frequency window of variance (accuracy) of 0.0001 Hz or more specific during the patient's preferred 15 minute exposure sessions within a complete treatment schedule. The current invention further includes ULF therapy generator (frequency generating source), including an amplifier, controller and one of many possible emitter systems as disclosed herein for accurately generating and emitting the narrow and specific 0.6180 Hz frequency as per the disclosed complete treatment schedules for human patient repair and enhancement, reference FIG. 21. The current invention optionally encompasses frequency isolating and or dampening floor and or wall dampening system with frequency input and or output regulating baffles. The isolated ULF therapy room/chamber further includes oxygen regulation (about 19.5 to 23.5%) in the therapy chamber to optimize the patient's frequency therapy, such as in an emergency and or ultra-critical situation. The inventors theorize that the ULF therapeutic field effect (exposure), from the ULF generating source emitting and continuously maintaining a continuous sine wave frequency of 0.6180 Hz continuously maintaining a narrow and specific window of frequency variance (accuracy) of 0.0001 Hz of narrower during the 15 minute exposure sessions within a complete treatment schedule or schedules, the emitter having a sufficiently effective exposure (dose) preferably ranging between 6 inches to 12 feet from the patient's body.

Depending upon the specific ULF dosing applications, the current invention treatment room encompasses exposing a sufficient volume of the patient's electromagnetic field (dosing) to the selected ULF treatment schedule having significant bio-stimulative therapeutic effects, through administering the ULF therapy in an isolated room (chamber) preferably having a diameter of about 16 to 24 feet, reference FIG. 21.

In a specified embodiment current invention encompasses administering the ULF frequency complete treatment schedule to a human patient in an open air environment (no walls, no roof, etc.).

Hyperbaric Chamber Therapy

The current invention encompasses administering a complete ultra-low frequency therapy treatment schedule administering the narrow and specific 0.6180 Hz continuous sine wave frequency therapy to a patient as an adjunct therapy with a variety of hyperbaric chamber system therapies, including modifying currently existing hyperbaric chamber systems, reference FIG. 22.

Emergency Treatments

The apparatus and method of the current invention encompasses a human patient being transported on a gurney, reference FIG. 23, positioned within a transportable semi-spherical collapsible faraday frequency interference shielding cage that may be composed of a suitable flexible material such as polypropylene containing wire mesh and or net interference frequency dampening wire shielding materials, such as including silver, copper, gold, and or other suitable electro-conductive materials as needed to obtain the preferred faraday frequency interference shielding effects, and or having air-flow through characteristics, reference FIG. 23.

The transportable ULF flexible faraday treatment cage, reference FIG. 23, further optimizes the ULF administration, such as administered in an emergency and or life-threatening ultra-critical environment, and further optionally monitors the patient's biometrics, including administering a complete treatment schedule having parameters and or outcomes as defined herein such as administering to the patient a 0.6180 Hz sine wave frequency through one of many possible frequency generator and emitter systems as disclosed herein and ULF emitter systems, continuously maintaining a narrow and specific window of frequency variance (accuracy) within 0.0001 Hz or more specific as needed during the 15-minute exposure sessions within a complete treatment schedule, further including modifying and or adapting the faraday treatment cage to be coupled to a pre-existing emergency transport system.

The transportable ULF faraday shielding treatment cage may be used for emergency onsite frequency therapy, preferably administered immediately and or during transport, such as in an ambulance to improve the patient's survival rate and improving the long-term therapy effects by administering a 15 minute exposure session every 3 to 5 hours of the narrow and specific 0.618 Hz sine wave frequency continuously maintaining and narrow and specific window of frequency variance (accuracy) of 0.0001 Hz or more specific preferably administering to the patient an emitted power ranging between about 0.01 to 10 watts to significantly increase the patient's survival rate and or promote faster repair and recovery, and further includes ULF administration in a hospital and or clinical environment.

In Vitro Culturing Chamber

As an option or optionally the ULF energy may be applied (administered) directly to cell cultures in vitro (outside the body) and as it does travel through intervening body tissues, the preferred administered power (watt) range selected for the ULF administration to the cells is generally the same or less than the systemic human patient dose administration watt range of the ULF energy as it is emitted from the ULF apparatus. If filters, dispersion gratings, and or any other material lies between the FST frequency emitter source and the frequency targeted cell culture, any absorption and or dispersion of the frequency stimulation energy by such material should be taken into account and the applied FST frequency energy adjusted, if needed, to account for the material(s).

In several specified embodiments, the current invention encompasses apparatuses and methods employing an in-vitro ULF growth chamber for frequency treating cells, organs, reference FIG. 24, for repairing and enhancing cells, tissues, organs at any processing points or steps such as administering ULF to petri dishes, test tubes, portions and or complete human organs within the in vitro culturing chamber(s) such as but not limited to heart, lung, liver, kidney, and the like.

The current invention significantly reduces and or eliminates the slow, complex, and costly prior art steps of stem cell processing and or selection processes for other cell based therapies. This is an object of the invention.

In several specified embodiments the current invention encompasses interference frequency faraday shielded treatment chamber, reference FIG. 24, for in vitro 0.6180 Hz sine wave frequency treatment of cells, tissues and or organ repair and enhancement (including but not limited to heart, lungs, spleen, liver, kidney, and the like) further including frequency treatment of blood, and further including ULF exposure treatments for repair and enhancement of systemic cell processes such as but not limited to in vitro stimulation of three dimensional stem cell production, culturing, processing, repairing, augmenting, and or genetic repair and enhancing, and the like, such as augmenting and or enhancing CRIPSR process and procedures, preferably constructed of an air-impermeable polypropylene having interference frequency dampening and encapsulated shielding wire mesh and or net materials (faraday cage), further including silver, copper, gold, and or other suitable electro-conductive wire mesh and or net materials, to provide optimize biometric frequency conditions including whole organ enhancement utilizing an adjustable gantry platform to optimize the relationship for accurate and preferred dosimetry, further having frequency input and or output regulating baffle system, and further encompassing a safety mechanism (apparatus) to identify the authorized operator such as from scanning a finger, thumb, and or hand, key code input, and or other suitable safety encoding mechanisms for providing ULF therapy.

The current invention further encompasses providing therapeutic intervention for enhancement and damaged cell and tissue repair and or transplanting, whether it be from an accidents, surgeries, advanced age, and or genetics through a programmable ULF exposure(s) within a complete treatment schedule and providing accurate dosimetry for administering the narrow and specific 0.6180 Hz frequency preferably producing and maintaining an accurate continuous sine wave having an adjustable and programmable power range between about 0.0001 watts to 2 watts, and having a narrow and specific window of frequency variance (accuracy) within 0.0001 Hz or more specific as needed during the preferred 15 minute exposure sessions within a complete treatment schedule for human ULF repair and enhancement therapy as needed or desired, reference FIG. 24. Continuous sine wave form is most preferred.

As an option or variation of the current invention some ULF stimulation treated stem cells removed from the human patient's fat (adipose tissue) bone marrow blood, and the like having antimicrobial characteristics may remain in culture to maintain the cell line providing longer and or safer storage life for later use.

The in vitro culturing chamber, reference FIG. 24, a complete treatment schedule timing and therapeutic window encompasses exposing human cells, tissues and or complete organs, being exposed to the sine wave frequency of 0.61803 Hz for about 15 minutes, three times per 24 hours about every 3 to 5 hours, having an emitted power of up to about 2 watts and or an absorbed power of about 0.2 watts (note about ⅒th of emitted power is absorbed) depending upon cells, tissues and or complete organ's weight and or condition.

The current invention encompasses in vitro culturing chamber for administration ULF having a watt range and or time range for frequency stimulating petri dishes ranging between 0.0001 watt (0.1 mW—milliwatts) up to 4 watts preferably continuously maintaining a window of frequency variance (accuracy) of 0.0001 Hz or more specific during the preferred 15-minute exposure sessions within a complete treatment schedule.

The current invention's encompasses an in vitro culturing chamber system, reference FIG. 24, ULF administration apparatuses and methods illustrates a compact bench top system having a gantry style adjustable exposure platform for adjusting the exposure elevation having an adjustable exposure table height (inverse square) for accurately treating complete organs and or blood transfer pouches and the like, having adjustable exposure doses ranging from repair to enhancement, and further encompasses a polypropylene faraday interference frequency dampening/shielding including sealed faraday/windows, operator I.D., a programmable timer, a frequency emitter surface, sterilizer switch, controlled temperature and or oxygen levels.

Cancer Prevention Therapy

In a several exemplary embodiments of the current invention encompasses that the FST apparatuses and methods are administered to a human patient for obtaining systemic human enhancement of biological function, including cancer prevention (anti-tumor and or anti-metastasis) such as but not limited to enhancement of the tumor micro-environment pH, genetic expression, reducing and or eliminating the tumor's production of lactic and or carbonic acid eliminating tumor growth (acidotic tumor micro-environment), further including repairing proto-oncogenes.

From administering a complete prophylaxis treatment schedule preferably from 15 minute exposure sessions from a 0.6180 Hz sine wave form systemic administration to cells, tissue, and or organs appears to be a very significant factor in determining the relative efficacy of ULF stimulation therapy, and particularly with respect to systemically preventing cancer and or enhancing the function of the patient's organs in both healthy and diseased states from the administration of the narrow and specific 0.6180 Hz frequency stimulation sine wave to a human patient in need of such a therapy. The current invention encompasses administering a complete treatment schedule to a human patient depending upon a variety of factors such as patient's current biological environment, genetic predisposition, diet, medical history, and the like.

The current invention encompasses administering the ULF therapy for cancer suppression and or complete remission as a stand-alone therapy and or as an adjunct therapy with conventional cancer therapies, including pH therapy, chemotherapy, radiation, and or surgery, further including pain suppression and or complete elimination, and further includes repairing damage induced from a conventional cancer therapy, and further systemically enhancing the patient's cells, tissues, and organs.

The current invention encompasses administering a complete ultra-low frequency treatment schedule of the narrow and specific 0.6180 Hz continuous sine wave frequency therapy administered about every 7 years to a human patient for prevention of cancer, including a prophylaxis therapy for cancer, including reducing and or eliminating reoccurrence and or producing and maintaining a state of remission.

Cancer Therapy

In some prophetic examples encompasses administering a ULF complete treatment schedule therapy for obtaining prophylaxis against the tumor micro-environment, administered as a stand-alone therapy and or as an adjunct therapy with conventional cancer therapies, including radiation, chemotherapy, and surgery, to a human patient that will significantly eliminate the possibility of the patient's cancer growing environment (having anti-tumor and or anti-metastasis characteristics) as administering a complete treatment schedule reduces and or eliminates the probabilities for a patient experiencing malignant cancers, further including suppression and or complete remission of the cancer growing environment (i.e. tumor micro-environment).

As discussed herein, the current invention's ULF treatment schedules have a particularly interesting therapeutic potential as a stand along therapy and or as an adjunct therapy in combination with anti-cancer stem cell therapies, particularly for non-operable malignant tumors, in that the conventional prior art therapeutic regime for treating cancerous diseases produces localized acidosis induced pain excreted from the tumor micro-environment that induces tissues damage to human patients.

The therapeutic goal of the ULF treatment schedule is to selectively kill cancerous cells, rather than the patient's normal healthy host cells. As such, combating these significant treatment-induced side effects of conventional cancer therapies with the current invention's non-invasive and drug free ULF therapy obtains significant pain suppression and or elimination and further improves the patient's survival rate. This is an object of the invention.

As discussed more fully below, in a prophetic example, the use of ULF therapies preferably in combination with the current invention frequency stimulating apparatus and methods enhances the efficacy of the anti-tumor stem cell therapy in general and leads to a faster, safer, and significantly more pronounced therapeutic gain in human cancer patients, including benign and or malignant tumor suppression and or complete remission, further including inoperable tumors.

Moreover, ULF therapy, in several prophetic examples, positively impacts stem cells, and or their secretions, in human cancer patients in a non-invasive and drug free manner which makes administering a complete treatment schedule disclosed herein more advantageous as a stand-alone or as an adjunct therapy with conventional human cancer therapies. Additionally the ULF therapy, in several exemplary embodiments, not only significantly enhances the effects of endogenous stem cells, enhancing the patient's own (autologous) production and release of stem cells, it also positively affects stem cells such that the combination of the human patient's own stem cells yields synergistically enhanced anti-cancer therapeutic effects, further encompassing suppression and or elimination of tumor generated pain and or it's signaling, including complete remission.

Note, adult stem cells produced and released in a human cancer patient will not be rejected by the human patient. Further, because adult stem cells generally develop into related cell types, the risk that the adult stem cells will develop into cancer cells are significantly reduced and or eliminated. Therefore, in some options, non-embryonic stem cells may be used (e.g., adult stem cells). In some options, the preferred ULF complete treatment schedule stimulation of autologous (self-derived) adult stem cells are preferred in order to significantly minimize the risk of immune rejection of the human cancer patient's own newly produced and or released stem cells.

Human Enhancement Therapy

In a specified prophetic example, administering a complete ULF treatment schedule to obtain systemic augmentation, including systemic genetic repair and genetic enhancement (Note the average human has about 400 genetic defects), in a human patient requires administering a ULF complete treatment schedule.

In a prophetic example, for prophylaxis against cancer, the current invention encompasses administering a complete ULF treatment schedule ranging between about every 5 to 15 years, preferably administered about every 10 years or as needed.

The current invention's human enhancement therapy stimulates the production of enhanced stem cells in a human patient and or systemically enhances the enhanced biostimulative secretions (secretome) in order to treat a condition, disease or diseases, and thus represents possible previously unavailable ULF apparatuses and methods for obtaining systemic human enhancement stem cell therapies in general for systemically repairing and replacing diseased cells and tissue with enhanced cells and healthy tissue. This is an object of the invention.

In several embodiments described herein, ULF therapy is administered to improve and augment and enhance the effects of many prior art stem cell therapies. As described in more detail below, as a prophetic example, ULF therapy is administered in several embodiments to stimulate the production and or enhance the viability of stem cells, and or their secretion(s). In several prophetic examples and embodiments, the current invention encompasses enhancing stem cell secretion, production, and significantly improved viability in a human patient, and further stimulates a significantly more robust stem cell population producing and or releasing between about 50 million into the billions of stem cells in a single exposure session.

In some embodiments, stem cells exposed to ULF therapy significantly proliferate to a greater degree, have enhanced survival, have increased differentiation. In some embodiments, ULF administration enhances the activation and or differentiation of endogenous stem cells in a human patient.

In several embodiments and prophetic examples herein, the current invention encompasses administering a ultra-low frequency therapy treatment schedule administering the narrow and specific 0.6180 Hz continuous sine wave frequency therapy to a patient employing at least one antenna system contained to administer the stimulating frequency to systemically significantly enhance the patient's stem cells (including enhancing their secretions) employing a treatment system of the current invention from the group consisting of: an immersion tank system, a pod system, a frequency containment shell system, a treatment room system, a hyperbaric chamber system, a handheld pistol emitter system, a wristband emitter system, an internal probe emitter system, and a epidermal patch emitter system.

The ULF administration of certain embodiments stimulates the production and release of potentially billions of stem cells from the patient's own genetically compatible cells, as an example for treating a 70 kg or 150 lb. male human patient, from ULF administration of the narrow and specific 0.6180 Hz sine wave frequency within a narrow and specific frequency range having an emitter power of about 0.01 watts or more as needed and or an absorbed power of about 0.2 watts or more (note about 1/10th of emitted power is absorbed) as described herein.

Diseases of Unknown Etiology

In a prophetic example the current invention's ULF apparatus and method encompasses frequency treating a disease and or condition that was previously diagnosed as being 'untreatable' and or treating a disease of unknown etiology.

In a prophetic example the current invention's ULF apparatus and method encompasses frequency providing prophylaxis treatment for a disease and or condition that was previously diagnosed as being 'untreatable' and or treating a disease of unknown etiology.

In a prophetic example the current invention's ULF apparatus and method encompasses reducing and or completely eliminating the medical prior part need for diagnostics.

Psychological/Behavioral Enhancement

The ULF apparatus and method encompasses administering the narrow and specific 0.618 Hz frequency therapy to a human a complete ULF treatment schedule to a patient wherein the human patient is subjected to the therapeutic treatment schedule for ULF therapy-induced improvements and enhancements in psychological attitudes and or behaviors in human patient.

The ULF apparatus and method encompasses administering the narrow and specific 0.618 Hz frequency therapy to a human a complete ULF treatment schedule as a stand-alone therapy to a patient instead of, and or administering as an adjunct therapy, with counseling for repair and enhancement in psychological attitudes and or behaviors in a human patient.

The current invention encompasses in several prophetic embodiments employing a complete ULF treatment schedule for reducing and or eliminating psychological and or physiological damage, including DNA damage, from encountered emotional trauma, including inherited DNA damage encountered from generational emotional trauma, such as emotional scars that significantly increase attitudinal disorders, mental health disorders, mania, depression, manic depression, and or suicidal tendencies, further including increased the patient's learning capacity providing the patient with faster learning and a higher percentage of retention.

In a prophetic example the inventors theorize that emotional trauma creates 'scarring' of DNA on the molecular level, further leading to intergenerational damage, including the behavior of those traumatized including depression, post-traumatic stress disorder, and those mental health conditions.

In a prophetic example, this 'molecular scarring' in DNA is caused by a chemical process known as methylation, the process by which a methyl group is added to DNA, which has a 'dampening effect' on certain gene expressions, and further affect the health of the offspring, in particular creating a kind of anxious behavior.

The inventors theorize that the ULF therapy will optimize the magnetic form and resonance of the DNA double helix structure including its epigenetic and or morphogenetic processes and characteristics, such as but not limited to modifying methylation and histidine formation. The inventors theorize this will reduce and or eliminate epigenetic damage resulting from trauma resulting from the patient and or their genetic ancestors.

The inventors theorize that the ULF therapy will optimize the magnetic form and resonance of the DNA double helix structure, to further optimize the quantum vibrational characteristics electromagnetic interface characteristics of the DNA with the patient's physiology.

In a prophetic example, the current invention encompasses administering a complete treatment schedule to patient's suspect or diagnosed with emotional trauma and corresponding molecular damage, particularly administering a complete ULF treatment schedule to a child, preferably over the age of 7 depending upon the state and condition of the patient.

In a prophetic example the inventors theorize many psychological diseases are going to have a genetic component and or biological basis (physiological). As a prophetic example the inventors theorize that what is currently referred to as Post Traumatic Stress Disorder (PTSD), which is defined as a psychological disease or condition will actually be the result of a physiological disease or condition, such as Chronic Traumatic Encephalopathy (C.T.E.).

The current invention encompasses in several prophetic examples administering a complete ULF treatment schedule will significantly increase mental clarity and improve intelligence, such as by improving the patient's brainwave coherence, providing calm, clear, and or more creative thinking, further including faster learning, and further provides increased sense of well-being (i.e. mood elevator).

Heart Attack Therapy

In a prophetic example, the inventors theorize that ULF therapy is especially advantageous with respect to saving and or repairing and enhancing surviving, but endangered (dormant), cardiac cells and or neural cells after heart attack (e.g., in a danger zone surrounding the primary infarct after a cerebrovascular accident), that significantly extends the therapeutic repairing window beyond the conventional 'golden hour', and further provides previously unavailable heart attack prevention characteristics as needed in the medical art.

It is theorized by the inventor in a prophetic example that administration of the ULF therapy of the current invention is significantly extended the effective therapeutic treatment window of heart attack and or stroke.

Non-neural tissues are also subject to damage, aging and or disease. For example, cardiac tissue may be damaged after an adverse myocardial event, such as a myocardial infarction and or stroke, including hemorrhagic stroke. As discussed herein, blood cells may be damaged by chemotherapy and or radiation therapy exposure, and or aging. Liver cells may be damaged by toxins and or metabolic waste by products. These conditions, diseases and/or injuries, among others, are all candidates for administering ULF therapy of the current invention.

In a prophetic example the inventors theorize that administering a complete treatment schedule of ULF therapy exposure to infarcted cardiac tissue results in a statistically significant 60% increase in tissue ATP levels about two hours after a treatment schedule. Note the beneficial bio-stimulative effect of ULF therapy is maintained long after the treatment schedule is completed.

In a prophetic example the prolonged bio-stimulative effects are also due to stem cell releasing secretions producing preservation of mitochondrial function. The ULF therapy upon infarcted cardiac tissue potentially may exhibit over a 15% or more reduction in damaged mitochondria.

In a prophetic example the inventors theorize that the ULF therapy will significantly reduce free radicals in the mitochondria, thus significantly decreasing the mtDNA damage. The inventors further theorize this decrease in mtDNA damage, will result in a significantly increase stem cell propagation, as mtDNA integrity and health is a threshold for stem cell production and or maintenance.

The inventors theorize that preservation of existing tissue (neuroprotection) from indirect and or direct stem cell secretions may result from direct ULF stimulation of systemic tissues (e.g., such as by secretions producing ATP synthesis). Ischemia results in depletion of ATP in the ischemic zone due to pH reduction and lack of oxygen (hypoxia) and or glucose. The resultant lack of ATP, depending on severity, results in decreased cellular function. In extreme cases, energy depletion leads to cell depolarization, calcium influx, and or activation of inflammation necrotic and apoptotic processes. The administration of ULF therapy of the current invention stimulates the production of ATP in virtually all cell types, including cardiac tissue.

In certain exemplary embodiments, an apparatus and methods increases the production of adenosine triphosphate (ATP) to increase neurologic function in a human patient. The apparatus and methods comprises systemic ULF treatment of neurons with ULF therapy having a sine wave frequency of 0.6180 Hz.

Several exemplary prophetic examples and embodiments encompasses that administering a complete ULF treatment schedule of the current invention increases ATP concentrations in human patients, and are particularly advantageous because increases in cellular ATP concentration are related to cellular metabolism and are considered to be significant indications that the cell is viable and healthy.

In some prophetic examples and embodiments, administering a complete treatment schedule of ULF therapy administering a sine wave frequency exposure of 0.6180 Hz wherein a wide variety of positive effects on cellular metabolism in in-vitro and or in vivo cells are achieved.

In some specified prophetic examples and embodiments, the healthy cells functionally replace the damaged cardiac cells of the human patient, (e.g., ULF generated and emitted frequency passes through the patient's skin and or chest wall to frequency target cardiac tissue), thereby restoring and or enhancing cardiac function (partially or fully). Adverse cardiac events include, but are not limited to, myocardial infarction, aneurysm, ischemic cardiac tissue damage, congestive heart failure, cerebrovascular accident (stroke), atherosclerosis-induced events, and or coronary artery disease. In addition to cardiac conditions, disorders, diseases and or injury, in several embodiments, the current invention's ULF therapy provides a previously unavailable significant role in treating cardiac damage. Myocardial infarctions and strokes often result in substantial loss of function in portions of the myocardium. Generally, the myocardium is currently viewed in the prior art as comprising a terminally differentiated group of cells with limited capacity for self-renewal. Thus, ULF enhancement therapy to treat cardiac tissue damage represents great potential progress in helping post-infarction and or post-stroke human patients regain functionality, including administering ULF therapy to a human patient in ambulance and or emergency situations.

In several specified embodiments, the current invention encompasses a human patient being transported and treated on a gurney, reference FIG. 23, positioned within a transportable semi-spherical collapsible flexible faraday cage frequency shielding apparatus constructed of a suitable flexible shielding materials such as polypropylene having wire mesh, net interference frequency dampening and or canceling characteristics, such as including silver, copper, gold, and or their alloys, and or other suitable electro-conductive wire materials as needed to obtain the preferred faraday frequency interference shielding effects, and or having air-flow characteristics.

The transportable ULF treatment cage further improves the ULF treatment outcomes, such as in an emergency situation and or life-threatening ultra-critical condition, preferably additionally monitors the patient's biometrics, during emergency administering a ULF complete treatment schedule parameters and improved outcomes as defined herein such as administering to the human patient a 0.6180 Hz frequency preferably continuously emitting a sine wave form and continuously maintaining a narrow and specific window of frequency variance (accuracy) within 0.0001 Hz or more specific as needed during the preferred 15 minute exposure sessions within a complete treatment schedule.

The transportable light weight ULF shielding treatment cage may be used for administering onsite emergency frequency therapy, preferably onsite prior to and or during transport, to improve the patient's survival rate and improving the long-term therapy effects.

In a specified embodiment, the current invention encompasses a transportable vehicle having an ULF therapy shielding cage on board, such as in an ambulance, van, camper, intermodal, truck, train, and the like.

Treatment of Stroke

In several embodiments, as discussed herein, ULF therapy is significant if administered to a patient soon after an injury (e.g., for traumatic injury including onset of stroke). In several embodiments, a ULF complete treatment schedule is preferably administered to a patient as soon as possible after an injury, and or partially administering from an emergency ULF emitting pistol as needed.

The inventors theorize that ULF therapy is especially advantageous with respect for treating and or enhancing surviving but endangered neurons after stroke and or heart attack (e.g., in a danger zone surrounding the primary infarct after a stroke and or cerebrovascular accident). That significantly extends the therapeutic window beyond the prior arts traditional golden hour, to beyond many hours after the stroke has occurred, or potentially even years or decades following the cardiac and or stroke incidence.

Because oftentimes many hours pass before a human patient who has suffered a stroke receives medical treatment conventionally, the short time limit for initiating thrombolytic therapy thus excludes many patients from such treatment. Consequently, the current invention's transportable apparatus and methods may be used to treat a greater percentage of stroke patients, such as in emergency situations, further including administering onsite and or in an ambulance and the like.

A wide variety of stem cell secretion factors have been implicated in biological repair, including neuroprotection, in addition to VEGF, including BDNF, GDNF, EGF, FGF, NT-3, etc.

In several prophetic examples and embodiments, one or more of the enhanced stem cell secretion factors are up-regulated to promote neuronal (or other cellular) survival, repair, and or enhancement. In some prophetic examples and embodiments, FST significantly systemically increases one or more of the following: mitochondrial respiration, production of molecular oxygen, DNA synthesis, DNA repair and or DNA enhancement.

In addition, in a prophetic example the inventors theorize ULF complete treatment schedule generation and administration stimulates mitochondrial repair and enhancement of functions, and the like to work in myocardial infarction.

In certain prophetic examples the ULF therapy produces and maintains an accurate continuous sine wave emission form that stimulates human neuroprotection and or enhancement that may further result in decreases of toxic factors (e.g., antioxidant protection and or by reduction of deleterious factors to patient's cells, tissues, functions, and or survival). In some embodiments, regarding antioxidant protection, administering the ULF therapy will reduce and or repair damage induced by free radicals. By-products of free radical damage are found in damaged tissues following injury. Administering continuous sine wave is preferred.

Accordingly, in a prophetic example it is theorized that the current invention's ULF complete treatment schedule therapy may enhance cognitive and/or motor function in a human patient after a primary event occurs, in that it appears that the neural cells in a human patient need only be living, including dormant, to receive therapeutic gain from administering the inventive ULF therapy apparatuses and methods disclosed herein, including emergency therapy.

Because strokes correspond to blockages and or other interruptions of blood flow to portions of the brain, effects of increasing blood flow of said blocked vessels by administering the current invention ULF therapy in some embodiments may be of more significance in the efficacy of ULF for stroke victims. In other embodiments, systemically treating vessels with interrupted flow may be more beneficial.

Without being bound by theory and or a specific mechanism, in a prophetic example of administering a complete ULF treatment schedule emitting a continuous 0.6180 Hz sine wave to a patient having a stroke, reduction of infarct volume often occur in one of two ways or a combination of both: (i) preservation and or repair of existing tissue (neuroprotection), and or (ii) generation and or enhancement of new tissue (neurogenesis). In a prophetic example the potential effects of ULF therapy on neurogenesis are such that the frequency enhancing stem cell therapy significantly increases the number of new stem cells (potentially in the billions), and or it prevents the loss of new cells that are generated as a result of the direct ULF stimulation therapy in combination with enhanced stem cells secretions.

In other embodiments, the ULF stimulation therapy, including enhanced stem cell therapy, is used to treat the cell damage due to stroke. In one embodiment, cerebral ischemia (including focal cerebral ischemia), traumatic brain injury, and/or physical trauma such as crush and or compression injury in the CNS, including a crush and or compression injury of the brain, spinal cord, nerves and or retina, is preferably treated with a complete treatment schedule No. 2 or No. 3 in more severe conditions.

Thus, in some embodiments, ULF therapy encompasses an effect on one or more levels of the biochemical cascade that controls neuronal (or cellular) viability. After ischemia, the myocardial tissue that is not immediately lost is in a dormant state, and may remain dormant for a period of days or weeks or longer. More specifically, it is the mitochondria in the tissue that are dormant. If the mitochondria are still intact, exhibiting characteristic morphological changes that are not metabolically active. As such, even after an alkalizing pH increase and restored blood flow, the mitochondria may be unable to convert oxygen and glucose to useable (ATP) energy.

In a prophetic example, the inventors theorize administering ULF treatment schedule therapy will reactivate and further enhance dormant cellular metabolic activities.

In addition, in a prophetic example, the ULF therapy encompasses that administering a complete treatment schedule may be effective when initiated up to about 24 hours, or longer, after strokes, which is later than any other previously effective single therapy in the same preclinical stroke model. In several prophetic examples and embodiments, a complete FST treatment schedule provides a viable therapeutic schedule regime for the treatment of stroke (or other brain/neural injuries) that provides significantly long-lasting therapeutic gain (e.g., recoveries) in neurological functions. Thus, several embodiments are particularly significant as an alternative and or adjunct with pharmacological therapies and or surgeries. In some embodiments. FST optionally synergistically works with some pharmacological therapies and or surgeries. In another embodiment, FST may reduce the dose of drug(s) needed to achieve a comparable effect or outcome.

Given the propensity of neurological disorders and or acute neural injury to induce a loss of function of one or more neural cells, the disclosure herein encompasses the positive effects of ULF administration to organs, tissues and cells, in particular repairing and enhancing neural stem cells. Cultured healthy neurons may be used to investigate the effects of ULF and neural stem cell therapy employed in combination (as an adjunct therapy) to Treat mild and or Acute Neural injury.

In a prophetic example administration of a complete ULF treatment schedule achieves the goal of human neuroprotection, motor enhancement and or cognitive enhancement, and or repair and enhancement of stem cell secretion, production, and or enhanced viability, proliferation, differentiation, and the like.

As discussed above, increasing the therapeutic efficacy of enhanced stem cell therapy is desirable. As an option, FST may optionally be administered to cultured neural stem cells (or other cells) in vitro according to parameters disclosed herein, reference FIG. 24.

In certain embodiments, administering an apparatus and method of the current invention prevents stroke in a human patient. The term "preventing" in this context includes reducing the severity of a later heat stroke in a human patient that received the ULF in a complete treatment schedule as disclosed herein, for reducing the incidence of stroke, including heat stroke, in human patients that have received ULF complete treatment schedule therapy, as well as reducing the likelihood of onset heat stroke in a human patient that received ULF therapy treatment schedule. The apparatus and method preferably includes systemically administering ULF stimulation therapy preferably emitting continuous sine wave form to a human patient having a specific window of frequency variance (accuracy) of 0.001 Hz or more specific and a frequency of 0.6180 Hz sine wave wherein the narrow and specific frequency, chosen power (watts) and or dose of the ULF are sufficient to prevent, reduce the severity, and or reduce the incidence of stroke in the human patient, including suppression and complete remission.

In accordance with several prophetic examples and embodiments encompass ULF apparatuses and methods including treatment schedules for preventing stroke (prophylaxis), including heat stroke, in a human patient.

In a prophetic example, naturally-occurring growth factors in the adult human brain may spur the production of new nerve cells from administering the current invention's complete ULF treatment schedule therapy, and further enhances stem cells, including their secretions. After a stroke, neurogenesis commences with stem cells migrating to the damaged area(s) and becoming adult neurons.

In several embodiments, neutropenia is treated using the invention's ULF treatment schedule by frequency stimulating the production and release of enhanced stem cells from the human patient's own (autologous) cells into the patient's peripheral blood for repopulating the dwindling and or damaged cell numbers due to natural aging process, damage from injury and or disease. In some embodiments, such ULF therapy apparatuses and methods are used to treat Non-Hodgkin lymphoma, Hodgkin's disease, neuropathy, malignant cancers, benign tumors, and or side-effects of a therapy for Non-Hodgkin lymphoma, preferably with the administration of a complete treatment, preferably treatment schedule no. 3, or as needed.

In certain embodiments, a ULF apparatus and method for stimulating and enhancing hematopoietic stem cell (HSC) production and or release (mobilization) in a human patient preferably comprises administering a ULF therapeutically-effective dose or dosages of a therapeutic sine wave having a frequency of 0.6180 Hz with a narrow range of variance for administering ULF treatment schedule doses designed to increase the quantity and quality of hematopoietic stem cells in the bloodstream and enhances the human patient's systemic function.

Several exemplary and prophetic examples and embodiments of the current invention encompasses that the FST apparatuses and methods are administered to a human patient for obtaining systemic frequency stimulation for repair and enhancement of human biological function based in part on the previously unavailable innovative synergistic discovery that ULF administration of 0.6180 Hz preferably emitting a continuous sine wave continuously maintaining a narrow window of variance of 0.0001 Hz with sufficient watts (i.e., power) for the complete treatment schedules' systemic enhancement therapy administered to the patient's cells, tissue, and or organs appears to be a very significant factor in determining the relative efficacy of ULF stimulation therapy, and particularly with respect to systemically enhancing the function of the patient's organs.

Alzheimer's Therapy

In certain embodiments, an apparatus and method of ULF treating a human patient is disclosed. The method encompasses preferably systemically administering a complete ULF treatment schedule therapy to the human patient's entire body that is sufficient to prevent, reduce the severity, and or reduce the incidence of Parkinson's disease, C.T.E., Alzheimer's and the like, in the human patient, further including the ULF complete treatment schedule being administered as an adjunct therapy with a hyperbaric chamber therapy.

As discussed above, ULF therapy may be used to treat a wide variety of ailments, conditions, disorders, injuries and diseases, such as dementia, C.T.E. Alzheimer's, and the like in a human patient by treating and or curing the underlying disease (e.g. infection, aging, nutritional deficiency, injury, tumor). Note that currently in the medical prior art, most dementia cases are considered incurable.

The current invention encompasses employing ULF administration apparatuses and methods for the treatment of a wide variety of neurodegenerative disorders in a patient such as but not limited to dementia, Alzheimer's disease, Parkinson's disease, C.T.E., Hodgkin's disease, and further promotes faster recovery times and previously unavailable neuro-cellular enhancement from administering a complete treatment schedule as disclosed herein.

As an example, the most common causes of dementia is an underlying neurological condition, disorder, injury, and or disease, such as Alzheimer's disease, which is currently increasing in occurrence, as is the resulting dementia. Other non-limiting examples of causes of dementia may include aging, AIDS or HIV infection, including environmental toxins, Lewy body disease, Pick's disease, Parkinson's disease, Huntington's disease, drug and or alcohol abuse, brain tumors, genetics, hydrocephalus, and or kidney and or liver disease, and the like.

As discussed herein, injury and/or disease may result in the loss of function and or death of cells in a tissue afflicted with or indirectly impacted by disease and or injury. For example, age-related degeneration of tissues may lead to loss of function of neurons in the eye, loss of tactile sensations, reduced control over muscle movement, memory failure, among many other possible effects.

Additionally, generally elderly healthy individuals may also perceive some loss of cognitive function and or diminishment of memory that may occur in any of the four commonly designated phases of memory, namely learning, retention, recall and or recognition, and may be related to immediate memory, recent memory and or remote memory. Loss of motor function may occur as a result of any of a number of causes, including many of those discussed above for which there is also a loss of cognitive function.

In a prophetic example the current invention encompasses administering a complete ULF treatment schedule to reduce and or completely eliminate the loss of cognitive function and or diminishment of memory that may occur in any of the four commonly designated phases of memory, namely learning, retention, recall and or recognition, and may be related to immediate memory, recent memory and or remote memory.

Alzheimer's disease is another neurological disorder that affects numerous individuals globally, thus administering the current invention's ULF therapy for genetic repair and enhancement for repair and replacement of damaged, diseased neurons through the current invention's ULF therapy may compensate for the loss of function experience by Alzheimer's in human patients.

Apart from degenerative disorders, acute injury to neural tissues may lead to loss of neural functions. For example, traumatic brain injury (TBI) may yield cell damage and or death by both primary and or secondary mechanisms (discussed further below). Head injury in general, whether from chronic impacts to the head and or from inflammation of the brain, as occurs in C.T.E. diseases, due to encountered impacts, may also reduce the function of neurons. Additionally, spinal cord injury is one of the forms of acute injury to neural tissue. In a prophetic example administering the current invention's complete ULF treatment schedule therapy obtains repair and enhancement in this area of neurological disorders and to obtain repair and enhancement of function to organs and or limbs (partial or complete) that have lost function due to an injury, furthermore significantly increasing the patient's quality of life as well as significantly extending the normal lifespan of the human patient.

As discussed herein, numerous other conditions, disorders, and or diseases may be treated with ULF therapy. In several embodiments, the frequency stimulated cells produce dopamine to treat, and or lessen the symptoms, and or delay onset of neurodegenerative diseases, including Parkinson's disease and or C.T.E., and or other neural disease(s) not specifically mentioned herein in a human patient. This is an object of the invention.

C.T.E. THERAPY

In certain exemplary embodiments, apparatuses and methods for treating a human patient suspect or diagnosed with C.T.E. encompasses a pre-programmable apparatus to administer a complete treatment schedule as disclosed herein.

The length or duration for administration of the invention's ULF complete treatment schedules may depend on several factors, including the functional recovery of the human patient, such as expressed through the results of imaging analysis of the patient. In certain embodiments, one or more complete frequency stimulation treatment schedules' parameters may be adjusted in response to a feedback signal from a monitoring device (e.g., magnetic resonance imaging) monitoring the human patient.

In certain embodiments, an apparatus and method for treating a human patient having impairments, such as from neurodegeneration. The apparatus and method comprises providing administration of a ULF treatment schedule to a human patient diagnosed having impaired neurologic function affected by Parkinson's disease, Alzheimer's, C.T.E, and the like for frequency stimulation therapy and systemic human repair and enhancement and or for frequency stimulated stem cell enhancement, and or enhancement of stem cell secretion(s), for improving the production and release (including viability and or function) of neural cells, including stem cells, produced from the human patient (among other applications). This is an object of the invention and may further functionally augment and enhance and or replace (partially or fully) the damaged and or diseased neural cells of the human patient.

In certain embodiments, the current invention's apparatuses and methods encompass placing a ULF emitter system source in a near proximity, and or a pre-calculated distance, that is either located adjacent an area of the patient's targeted organ or organs in which the complete frequency treatment schedule is administered for localized and or systemic repair and or enhancement, including contralateral to such area, or a combination of the foregoing, and then administering ULF therapy complete treatment schedule to a human patient, including the preferred effective dosage or amount of ULF therapy for enhancing neurologic functions, such as by measuring and or monitoring dosage in real time including frequency, sine wave characteristics, watts, distance between patient and ULF emitting source, and or any combination therein for measuring and or monitoring systemically and or optionally measuring and or monitoring a targeted area or areas as needed to treat a patient, including those suffering from neurodegeneration and or a loss or diminishment of motor skills, cognition or cognitive or mental processes or functions, further including patients having generally normal cognitive and or motor functions (whether to repair and enhance such functions and or to pre-treat so as to prevent and or lessen stroke, including heat stroke, and or C.T.E.), and or to potentiate and/or otherwise obtain human enhancement, including enhanced stem cell therapies for a wide variety of neurological diseases, further including administering a ULF complete treatment schedule functioning as a neuro-protectant against C.T.E.

In a specified embodiment, the ULF wave guide emitter system is preferably placed in close proximity with a region of the patient's body. In certain embodiments, a surface wattage of the ULF energy sufficient for the ULF energy to penetrate the patient's entire body is determined. The determination of the required surface wattage, which is relatively higher than the watt to be absorbed by the human patient's body (or other) tissue being treated, takes into account factors that attenuate wattage as it travels through the patient's tissue, including the weight of the human patient (or other intervening tissues). The watt power and or other treatment parameters may then be adjusted according to the results of such calculations.

For example, ULF administration to a large population of neural progenitor cells such as to an individual human patient diagnosed with Parkinson's disease and or C.T.E. (e.g. by frequency delivery of the ULF to a frequency targeted region of the brain) and administration of the disclosed complete treatment schedule ULF stimulation therapy, including preferred inverse square dosing relationships, in some embodiments, induces the production and or proliferation of the neural progenitor cell's repair and or enhancement to a degree which compensates for the loss of speech and or motor control associated with neurodegenerative diseases, including Parkinson's disease and or C.T.E. disease, and the like.

In certain exemplary embodiments, a ULF apparatus and method for treating and or preventing Parkinson's disease and or C.T.E. is disclosed. The ULF apparatuses and methods encompasses non-toxically and noninvasively systemically treating the human patient's entire body with a complete treatment schedule as disclosed herein.

In several specified embodiments, an apparatus and method of treating or preventing Parkinson's disease and or C.T.E., and the like, is provided. The method comprises noninvasively treating the patient's entire brain by administering a ULF therapy within a complete treatment schedule including administering a sine wave 0.6180 Hz frequency stimulation to the patient having an emitted power ranging between about 0.01 to 10 watts having a wave guide output emission area adjustably positioned for systemic and or localized therapy, including ULF dosing a damaged portion of the human patients brain with an efficacious wattage, and ULF administration therapy.

In several specified embodiments, an apparatus and method encompasses administering a complete treatment schedule of the narrow and specific 0.6180 Hz continuous sine wave frequency therapy to a patient for frequency entrainment within the human brain to the 0.6180 Hz frequency as disclosed herein.

As an option the ULF therapy apparatus and method may further encompass a ULF amplifier and ULF emitter apparatus adjustably interposed between the FST generator source and the patient's body. The ULF generating, amplifying, and emitting therapy apparatuses are additionally adapted to filter out undesirable interference frequencies.

In certain embodiments, the current invention's ULF generation passes through the ULF emitting apparatus to preferably be systemically administered to the human patient such that the amplifying and emitting apparatus is in the ULF path propagating from the ULF generator over the entire human patient's body, including through the fluids tissues and bones, of the patient's head, and through the entire brain. In certain embodiments, the FST passes from a frequency emitter system through a transmissive medium, including air and or water, at a preferred distance while in other embodiments.

In certain embodiments, a ULF apparatus and method is administered for preventing Parkinson's disease and or C.T.E. disease in a human patient is disclosed. The apparatus and method comprises disclosing Alzheimer's, Parkinson's and or C.T.E. prevention in a human patient having a predisposition towards contracting Alzheimer's, Parkinson's disease and or C.T.E. disease.

In certain embodiments and prophetic examples, encompasses administering a complete ULF treatment schedule for treating a human patient suffering from the effects of neurodegenerative disease (e.g., C.T.E. and or Parkinson's disease) may administer a repairing dose in a complete treatment schedule and or a human enhancement dose in a complete treatment schedule as disclosed herein.

In certain embodiments, an apparatus and method of systemically administering ULF therapy for treating the central nervous system of a human patient is disclosed. The ULF apparatuses and methods of the current invention comprise identifying a human patient exhibiting symptoms or damage to the central nervous system due to Alzheimer's, Parkinson's disease and or C.T.E. condition or disease, and the like.

The current invention encompasses ULF administration of the narrow and specific 0.6180 Hz frequency therapy preferably producing and maintaining an accurate continuous sine wave preferably having an emitted power ranging between about 0.01 to 10 watts for systemic and or targeted frequency administration to the patient's brain having biostimulative and enhancement effects on the patient's neurology including the patient's thinking, knowing, perception, learning, memory (including immediate, recent, and or remote memory), and or decision making. Note symptoms of loss of cognitive function may also include changes in personality, mood and or behavior of the patient. Conditions or diseases affecting cognitive function such as but not limited to Alzheimers disease, Parkinson's Disease, dementia, AIDS and or HIV, infection, C.T.E. (Chronic Traumatic Encephalopathy) Cruetzfeldt-Jakob disease, head trauma (including single-event trauma and or long-term trauma such as chronic encountered impacts producing C.T.E. and or other traumas which may result from athletic injury), and the like.

The term (Chronic Traumatic Encephalopathy) C.T.E. as used herein and as defined by Bennet Omalu, is characterized by regionally selective neuronal death and deposition of the protein tau into neurofibrillary tangles and which occurs in the brain and slowly spreads throughout the brain, killing brain cells. This has been observed in a significant number of professional football and or hockey players, as well as members of the military.

While this is currently seen as being a result of repetitive head trauma, the inventors theorize a more complete understanding would be that the significant C.T.E. damage occurs when the encountered impact waves collide together inside the subject's brain causing a localized cavitation effect, creating an effect similar to when standing waves that are initially created reinforce each other and carry the frequency higher, and that this is when the brain damage occurs. Note this complete effect may happen extremely rapidly, often in billionths of a second.

Note in a prophetic example the inventors theorize that the encountered impact frequency that produces C.T.E. in a patient is within the very narrow and specific megahertz range, particularly in relationship to the potential range of generated frequencies in the electromagnetic spectrum from a safety helmet's encountered wave impact propagations.

In a prophetic example the inventors theorize that concussion is caused from an encountered impact causing temporary reduction in pH (transitory acidosis and or hypoxia), more specifically a temporary reduction in brain tissue and cells PHE and PHI and thus triggers a temporary stoppage of cellular communication.

In a prophetic example the inventors theorize that the encountered impact generated frequency range that produces concussion is within the narrow and specific kilohertz range, particularly in relationship to the potential range of generated frequencies in the electromagnetic spectrum from a safety helmet's encountered wave impact propagations.

Both primary and or secondary mechanisms of action may contribute to forming a "danger zone" for neurons, wherein the neurons in the frequency zone have at least temporarily survived the primary destructive impact frequency event(s), that are dormant and or at risk of dying due to chronic cumulative encountered impact processes having delayed harmful effects, including chronic traumatic encephalopathy.

In certain embodiments, encompasses administering complete a ULF treatment schedule further including calculating a preferred surface watt range (power) for exposure of the scalp of the human patient, generally ranging between about 0.01 to 10 watts and a patient absorbed power of ranging between about 0.001 to 1 watts (note about 1/10th of emitted power is absorbed) which corresponds to a preselected watt range and or absorbed dose by the frequency targeted area of the human patient's brain.

The ULF dosage range selected to be applied to the patient's brain depends on a number of factors, including, but not limited to the power (watts), the accuracy of the sine wave form, the selected ULF distance of the patient to the ULF emitter administering the ULF therapy, the type of CVA (ischemic or hemorrhagic), and or the human patient's weight, further including clinical condition(s), current and prior medical history, and further including the extent of the affected brain area.

The current invention further encompasses a complete ULF treatment schedule to be administered to a frequency targeted area of the human patient's brain (or other tissue) may also be adjusted to be optionally combined with any other therapeutic agent or agents, having biological stimulative effect. In such embodiments, the selected watt range may also depend on the distance to the patient (inverse square) and or the additional therapeutic agent or agents administered.

The current invention encompasses that the ULF therapy treatment schedules may significantly improve the supply of vital nutrients and or organelles to axons and or synapses to compensate, at least in part, for the reduced axonal transport that is potentially reduced in human patients with Alzheimer's, Parkinson's disease, and or C.T.E. condition or disease.

In a prophetic example encompasses the view of the hypothesis that axonal transport of essential nutrients is reduced in human patients diagnosed as having Alzheimer's, Parkinson's disease and or C.T.E., certain embodiments described herein advantageously disclosed ULF administration and complete treatment schedules to provide repair and enhancement of this reduction of axonal transport. In certain embodiments disclosed herein, preferably systemically administering ULF therapy, including the brain cells, stimulates an improvement of mitochondrial function within the frequency stimulated neurons.

In some prophetic examples encompasses administering a complete ULF treatment schedule to repair a variety of neurological degenerative diseases, such as dopaminergic impairment, amyotrophic lateral sclerosis, and/or dementia, and to further enhance the neurological environment of the human patient.

In some prophetic examples encompasses administering a complete ULF treatment schedule to repair and enhance impaired neural function that is a result of injury to the human patient's neurons, further including repairing secondary destructive mechanisms that includes any mechanism that leads to the generation and or release of neurotoxic molecules, including apoptosis, depletion of cellular energy stores due to changes in mitochondrial membrane permeability, release and or failure in the reuptake of excessive glutamate, reperfusion injury, and or activity of cytokines and or hypoxic induced acidotic pain and or inflammation, and further includes enhancing the patient's neurological function.

As described above, ULF propagation through tissue is absorbed by the tissue, and in a specified prophetic example embodiment encompasses that dosage calculations of the watts to be administered to a human patient is an emitted power ranging between about 0.01 to 10 watts and a patient absorbed power of ranging between about 0.001 to 1 watts (note about 1/10th of emitted power is absorbed), to preferably take into account the attenuation of the ULF administered energy as it propagates through the patient's tissues, such as bone and or brain tissue.

In several exemplary and prophetic examples and embodiments, the administration of a complete ULF treatment schedule stimulates stem cells, in in vitro and or in vivo applications, that may be employed in a wide variety of stem cell therapies to repair and enhance a wide variety of neurological conditions, diseases, and or injuries, including neural cells and tissues having impaired function due to degenerative neural disease such as Alzheimer's, C.T.E. and or Parkinson's disease, and the like.

In several prophetic embodiments, the ULF stimulated stem cells are produced from the human patient's own cells for the treatment of Alzheimer's, C.T.E. and or Parkinson's disease, and the like.

In certain prophetic examples and embodiments, progenitor cells such as stem cells are harvested and frequency stimulated in vitro that are repaired and enhanced with the administration of a complete ULF treatment schedule dosing as noted herein, and then are administered into the brain of a human patient who is suspect or diagnosed with having a C.T.E. condition, disease, and or exhibits symptoms of C.T.E. condition, disease, and or is clinically diagnosed having C.T.E. condition or disease.

Without being bound by theory or by a specific mechanism, the inventors theorize that sufficient systemic frequency exposure of 0.6180 Hz sine wave in proximity to the area thereby systemically produces a wide variety of enhanced effects. In a prophetic example, ULF therapy provides human neurologic function enhancement through administration of ULF therapy to a human patient that is sufficient to prevent, reduce the severity, and or reduce the incidence of Alzheimer's, Parkinson's and or C.T.E. condition or disease in the human patient, including complete remission.

As described more fully herein, the ULF generating and emitting apparatus may be utilized with various embodiments of the ULF methods. Similar ULF generating and emitting therapy penetration pathways occur in other embodiments that are preferably systemically administered and released in combination with the narrow and specific sine wave 0.6180 Hz frequency to other cells and tissues requiring cell repair, replacement and or enhancement of damaged tissues, whether it be for immediate treatment of a human patient, cryo-storage for future use, and or for conducting research, reference FIG. 2.

Spinal Cord Therapy

In certain prophetic examples and embodiments, progenitor cells may be preferably treated systemically with ULF therapy that targets the site of physical trauma such as to the spinal cord and or one or more nerves of a human patient as disclosed herein, such as administering the ULF complete treatment schedule as disclosed herein including administering emergency frequency treatment prior to, and or immediately following ULF stem cell therapy treatment schedules for repair and enhancement treatment schedules as disclosed herein. In several prophetic examples administering a complete ULF treatment schedule therapy stimulates the stem cell repair of damage to the spinal cord and or nerve(s), including severed nerves, and further systemically enhance the patient's biological system including significantly reducing and or eliminating pain and or numbness, such that the recovery and or prognosis is significantly improved in a human patient, as compared with those who do not receive such ULF therapy.

In several prophetic examples the apparatuses and methods encompass administering a complete treatment schedule of the narrow and specific 0.6180 Hz sine wave frequency therapy to a human patient for suppression and or complete remission of neuropathy, including reducing and or eliminating pain and or numbness in the feet and or hands.

In a prophetic example administering the current invention's complete ULF treatment schedule as an adjunct therapy encompasses significantly improving stem cell therapy performances, including the overall enhancement of the patient's stem cells over the prior art, as there is minimal lag time between the ULF therapy exposure and the systemic receipt of previously unavailable beneficial bio-stimulative and enhancement effects. In several embodiments, complete treatment schedules are administered.

Stem Cell Storage/Banking

The ULF apparatuses and methods of the current invention encompass collection for diagnostic purposes, such as but not limited to screening for a hematologic and or oncologic disease, a therapeutic purpose, such as autologous (self-derived) and or heterologous blood or blood component donation (allogeneic), and or to stimulate the enhancement and or production of stem cells prior to and or during transplantation, procedures and or transport and or storage purpose, such as but not limited to stem cell banking.

In certain embodiments, the ULF administration as a stand-alone treatment therapy and or as an adjunct treatment therapy enhances prior art stem cell therapies, particularly for enhancing, thus significantly extending the stem cell storage life.

In a prophetic example the current invention's non-toxic and non-invasive ULF stimulation therapy and stem cell therapy complies with current U.S. stem cell regulations.

Treatment of Eye Diseases

In certain prophetic examples and embodiments, the apparatus and method of the current invention encompasses administering a complete ULF treatment schedules to a human patient for repair and recovery of a wide variety of ocular/eye disorders, injuries, conditions and or diseases such as but not limited to Cataracts, Astigmatism, Glaucoma, Conjunctivitis, Retinopathy, Stye, Dry eye syndrome, Macular Degeneration including Age Related Macular Degeneration, Low Vision, Diabetic Eye Disease, and or ocular degeneration such as from advanced age, and the like.

Treatment of Hearing Diseases

In certain prophetic examples and embodiments, apparatus and method according to any claim encompasses administering a complete treatment schedule of the narrow and specific 0.6180 Hz continuous sine wave frequency therapy to a patient for suppression and or complete remission of a wide variety of auditory/hearing disorders, injuries, including Otitis Media, Acute Otitis Externa, Balance Disorders including Ménière's disease, Tinnitus, Cisplatin-Induced Hearing Loss, Sensorineural Hearing Loss, and the like, further including hearing regeneration and enhancement.

Treatment for Scar Tissue and Adhesions

In several prophetic examples and embodiments, the current invention encompasses administration of the ULF therapy apparatuses and methods to a human patient for systemic reduction and or elimination of scar tissue and adhesions such as from injury and or surgery, including converting scar tissue to healthy tissue systemically and or locally, and further including repairing scar tissue from events that occurred years and or decades prior to the ULF treatment.

In several prophetic examples and embodiments, the human patient's ULF exposure sessions additionally functions in a systemic anti-fibrotic, anti-adhesion levels of action, that locally and or systemically reduces fibrosis (and associated loss of organ function).

Burn Therapy

In several specified prophetic examples and embodiments encompasses apparatuses and methods for the ULF administration to a human patient within a complete treatment schedule for treatment of burns and or significantly reducing and or eliminating the prior art procedures for skin grafting, including reducing prior art complex skin transplanting processes further including the associated cost, time and pain, and further reduces the risks of infection and or scarring, and further promotes a shorter recovery time with less scarring.

In a prophetic example administration of the ULF therapy for the treatment of burns further overcomes many of the prior art limitations such as the costly treatment of painting and or spraying atomized stem cells for treating human patients having burns, and or the formation of scar tissue (note most tumors are formed in scar tissue).

Drug Addiction Therapy

In certain prophetic examples and embodiments encompasses the systemic administration of a ULF treatment schedule to a human patient for the suppression and or complete remission of drug and or alcohol addiction by administering a complete treatment schedule.

Wound Care Therapy

In certain prophetic examples the apparatus and methods of the current invention encompasses administering the narrow and specific 0.6180 Hz sine wave frequency therapy, preferably within a complete treatment schedule to a patient for wound care treatment (repair) such as reducing and or eliminating infection, scarring, adhesions, odor, and significantly improves recovery times, further systemically enhancing the patient from administering a complete ULF treatment schedule.

C.O.P.D. THERAPY

In certain prophetic examples and embodiments encompasses administering the systemic and or lung targeted ULF complete treatment schedule to a human patient for the suppression and or complete remission of C.O.P.D. Note C.O.P.D is the 4th biggest killer globally.

AIDS Therapy

In certain prophetic examples and embodiments encompasses apparatuses and methods for systemic administration of a ULF complete treatment schedule for the suppression and or complete remission of A.I.D.S. (auto immune deficiency syndrome) and other auto-immune deficiency diseases.

Pesticide Therapy

In certain prophetic examples and embodiments encompasses apparatuses and methods for the systemic administration of ULF therapy treatment schedules to a human patient for suppression and or complete remission of pesticide poisoning, including their symptoms, including inflammation, confusion, nausea, tissue damage, respiratory challenge, memory loss and the like.

Lyme Disease Therapy

In certain prophetic examples and embodiments encompasses apparatuses and methods for the systemic administration of ULF complete treatment schedule to a human patient for the suppression and or complete remission of Lyme disease and or restoring and enhancing the patient A.T.P. production from administering a complete treatment schedule, further including cellular detoxification and or cellular peptide rejuvenation.

Bacteria Therapy

In certain prophetic examples and embodiments encompasses apparatuses and methods for the administration of a systemic ULF treatment schedule to a human patient for the suppression and or complete remission of bacteria induced infection, including bacterial meningitis, otitis media, pneumonia, tuberculosis, upper respiratory tract infection, gastritis, food poisoning, eye infections, sinusitis, Methicillin-resistant *Staphylococcus aureus*, vancomycin resistant *Staphylococcus aureus, streptococcus*, and the like.

Therapy for Periodontal Disease

In certain prophetic examples and embodiments encompasses apparatuses and methods for the systemic and or targeted ULF administration of a complete treatment schedule to a human patient for the suppression and or complete remission of periodontal diseases, further including promoting shorter recovery time and or pain suppression and or elimination from a wide variety of dental therapies such as but not limited to treating of dental implants, dental surgery, periodontal disease, and the like, including selective reduction and or elimination of hypoxic bacteria in the periodontal cavity (there are over 600 varieties of bacteria in the oral region, and particularly in the periodontal pocket).

In other specified prophetic examples and embodiments encompasses that the apparatuses and methods of the current invention eliminates the need for a wide variety of temporary and or permanent implantable medical devices common in the dental prior art.

In a prophetic example, administering a complete ULF treatment schedule suppresses and or eliminates a wide variety of periodontal conditions and or diseases, and their resultant conditions and diseases such as but not limited to pain, heart disease, a wide variety of cancers, osteoporosis, Alzheimer's, premature aging, and the like, and further encompasses ULF administration before, during, and or after oral surgeries, tooth replacement, gum transplanting, and the like.

Dental Therapies

In certain embodiments encompasses apparatuses and methods for the systemic and or targeted ULF treatment administration of a treatment schedule as a stand-alone therapy and or as an adjunct therapy (before, during, and or after) to a human patient for a wide variety of oral cavity disorders, diseases, and procedures, such as but not limited to gum grafting, transplants, tooth implants, bone grafting, cosmetic procedures including surgeries, that is systemic, faster, and or safer, further including pain suppression and or elimination.

In a prophetic example, administering a complete ULF treatment schedule significantly improves teeth re-alignment, or the straightening of teeth of an average patient, if the person is wearing tensioning braces as an adjunct during ULF therapy, such as but not limited to braces, brackets, clear aligners (such as Invisalign®), bands, arch wires, elastomerics, patient ties, metal brackets, direct bon buccal tube, duraform arch wires, molar bands would significantly shorten the correction time involved in the orthodontic therapy.

Shock Therapy

In certain prophetic examples and embodiments encompasses apparatuses and methods for systemic administration of ULF therapy including emergency treatment, preferably followed by a complete treatment schedule to a human patient for suppression and or complete remission of bacterial induced shock, including promoting shorter recovery times.

Malaria, Sleeping Sickness, Dengue Fever Therapy

In certain prophetic examples, apparatuses and methods for systemic administration of a ULF treatment schedule to a human patient for suppression and or complete remission of malaria, sleeping sickness, and or Dengue Fever further including promoting faster recovery times.

Hemorrhagic Therapy

In certain prophetic examples and embodiments encompasses apparatuses and methods for the systemic administration of a ULF therapy treatment schedule to a human patient for suppression and or complete remission of hemorrhagic fever(s) such as Ebola, Congo, Zaire, Crimean, West Nile Virus, Marburg Virus and the like and or further encompasses promoting higher survival rates and or shorter recovery times, even in advanced stages.

Cold and Influenza Therapy

In certain prophetic examples and embodiments encompasses apparatuses and methods for the systemic administration of a ULF treatment schedule to a human patient for suppression and or complete remission of COVID, coronavirus infection, colds and or influenzas, including H1N1 and rhinovirus, and further encompasses promoting shorter recovery times.

Prostate Therapy

In certain prophetic examples and embodiments encompasses apparatuses and methods for the systemic administration of a complete ULF treatment schedule to a human patient for prostate therapy for repairing and enhancing prostate function, including treating enlarged prostate, further encompassing increased semen production that is further enhanced, and further promoting shorter recovery times.

In certain prophetic examples and embodiments encompasses apparatuses and methods for the systemic administration of a complete ULF treatment schedule to a human patient for increasing semen production and further enhancing the semen qualities and characteristics, including enhancing the semen's genetic profile.

Sexually Transmitted Diseases

In certain prophetic examples and embodiments encompasses apparatuses and methods for the systemic administration of a complete ULF treatment schedule to a human patient for prophylaxis, suppression, and or complete remission of a wide variety of sexually transmitted diseases and or sexually transmitted infections such as but not limited to Herpes Simplex Virus (I and II), genital warts, chlamydia, gonorrhea, syphilis, trichomoniosis, hepatitis, human papilloma virus, HIV/AIDS, and the like.

Erectile Dysfunction

In certain prophetic examples and embodiments encompasses apparatuses and methods for the systemic administration of a complete ULF treatment schedule to a human patient for erectile dysfunction therapy, including repairing and enhancing the bulbourethral glands, corpus spongiosum (or corpus cavernosum urethrae), the glans penis and the like, and further encompasses a long lasting effect, theoretically will be effective for 5 to 10 years, further including penis enlargement.

Vaginal Therapy

In certain prophetic examples and embodiments encompasses apparatuses and methods for the systemic administration of a complete ULF treatment schedule to a human patient for long lasting (theoretically about 5 to 10 years) vaginal repair and enhancement therapy, including tissue tightening, including reducing or eliminating stretch marks after giving child birth and weight loss, and further including Pre- and post-natal repair and enhancement therapy.

Childbirth Therapy

In certain prophetic examples and embodiments encompasses administering a complete ULF treatment schedule emitting a narrow and specific 0.6180 Hz sine wave frequency therapy before, during, and or after childbirth, including cesarean sections, to reduce maternal mortality.

In-Vitro Fertilization Therapy

In certain prophetic examples and embodiments encompasses an in-vitro cell culturing chamber that accurately administers the narrow and specific 0.6180 Hz sine wave frequency therapy for repair, augmenting, and or enhancing cells and tissues at any point during the IVF (In vitro fertilization) process, including administering the ULF therapy to the egg donors and or the egg recipients.

In certain prophetic examples and embodiments encompasses accurately administering a complete ULF treatment schedule administering the narrow and specific 0.6180 Hz sine wave frequency therapy to patient or patients before, during and or after conception.

In certain prophetic examples and embodiments encompasses accurately administering a complete ULF treatment schedule administering the narrow and specific 0.6180 Hz sine wave frequency therapy to a mother during the course of her pregnancy.

In certain prophetic examples and embodiments encompasses accurately administering a complete ULF treatment schedule administering the narrow and specific 0.6180 Hz sine wave frequency therapy to babies born prematurely.

In certain prophetic examples and embodiments encompasses accurately administering a complete ULF treatment schedule administering the narrow and specific 0.6180 Hz sine wave frequency therapy to babies after they are born, such as in a retrofitted and or inventive incubator system.

In certain prophetic examples and embodiments encompasses accurately administering a complete ULF treatment schedule administering the narrow and specific 0.6180 Hz sine wave frequency therapy to repair and enhance fertility within a human patient.

Allergy Therapy

In certain embodiments encompasses apparatuses and methods for the systemic administration of a complete ULF treatment schedule as a stand-alone therapy and or as an adjunct therapy to a human patient for suppression and or complete remission of a wide variety of allergies and their symptoms, and or further includes enhancing the effects of anti-allergy medication.

In certain embodiments encompasses apparatuses and methods for the systemic administration of a complete ULF treatment schedule, such as an emergency treatment schedule, as a stand-alone therapy and or as an adjunct therapy to a human patient for prophylaxis against a wide variety of allergies and their symptoms, including histamine responses, and or further includes enhancing the effects of anti-allergy medication.

Cosmetic Surgery/Skin Therapy

In several specified prophetic examples and embodiments encompasses apparatuses and methods for the systemic administration of a ULF treatment schedule as a stand-alone therapy and or as an adjunct therapy with cosmetic procedures such as but not limited to surgery, lasering, cosmetic product utilization, liposuction, and or cryogenic treatments, for administering to a human patient for non-invasively and non-toxically providing a wide variety of aesthetic and cosmetic benefits including significant reduction and or elimination of wrinkles and or scar(s) such as from wounds, plastic surgery, weight loss, age advancement, sun burn, and the like, further including reducing and or eliminating fine skin lines, wrinkling, such as face fissures and or crow's feet, and or sagging, thus tightening and or tonifying the patient's skin, increasing blood flow, reducing and or eliminating brown pigment spots, redness and or discoloration, balancing the skin tone, eliminating varicose veins, and or stimulating collagen production, including repairing and enhancing the interstitial matrix beneath the skin, restoring a youthful appearance, promoting the elimination of acne, and further including fat/adipose and or collagen transfer, and the like.

In several specified embodiments encompasses apparatuses and methods for the systemic and or targeted complete ULF treatment schedule administration to a human patient for non-invasive, non-toxic, non-surgical facelift and or systemic skin tonifying in general.

In several specified embodiments encompasses apparatuses and methods for the systemic and or targeted administration of a complete ULF treatment schedule to a human patient for reducing and or eliminating the need for prior art cosmetic skin transplanting and or grafting processes and procedures, including lasering, and or further promotes improved patient outcomes and or improved recovery (shorter recovery time) such as from scarring, infection, and the like, and that is non-invasive, faster, simpler, and significantly safer.

In several specified embodiments encompasses administering a complete ultra-low frequency treatment schedule therapy to a patient for adjunctive therapy for the palliative treatment of postoperative edema and or pain in superficial soft tissue and systemically enhancing the patient's biological system.

In several specified embodiments encompasses administering a complete ultra-low frequency treatment schedule therapy to a patient for facial skin tightening, body contouring, wrinkles (crow's feet), and systemically enhancing the patient's biological system to appear more youthful.

Hair Therapy

In a prophetic example the current invention's complete ULF treatment schedule encompasses administering a complete treatment schedule of the narrow and specific 0.6180 Hz sine wave frequency therapy to a human patient for treating and or enhancing alive, including dormant, hair cells (follicles) for suppression and or complete remission of thinning hair and balding.

In a prophetic example the current invention's complete ULF treatment schedule encompasses administering a complete treatment schedule of the narrow and specific 0.6180 Hz sine wave frequency therapy to a human patient as a stand-alone therapy and or as an adjunct therapy with hair transplant processes and procedure, and further encompasses culturing hair, and or spraying on ULF treated cultured hair follicle cells, and further includes encompasses thickening hair and or restoring the natural color of hair, furthermore enhancing and extending the life of the patient's hair.

EMF Sensitivity Therapy

In a specified embodiment the apparatuses and methods of the current invention encompasses administration of the ULF therapy treatment schedule administering to a patient a 0.6180 Hz frequency preferably emitting a continuous sine wave maintaining a window of frequency variance (accuracy) of 0.0001 Hz or more specific administering to a patient an emitted power ranging between about 0.01 to 10 watts and a patient absorbed power of ranging between about 0.001 to 1 watts (note about 1/10th of emitted power is absorbed), or dosed as needed, during the 15 minute exposure treatment sessions to ameliorate symptoms of hypersensitivity to electromagnetic fields or as needed in a patient in need of such a treatment.

Radiation Poisoning Therapy

In certain prophetic examples and embodiments encompasses apparatuses and methods for the systemic administration of the complete ULF treatment schedule to a human patient for suppression and or complete remission from a variety of radiation exposure symptoms, such as but not limited to fatigue, skin sores, memory loss, nausea, pain, confusion, and or damage, such as damage incurred during cancer therapies and or nuclear accidents or events, further including commercial airline pilots, military personnel, nuclear industry personnel, and further including background and or ambient radiation.

Note, in a prophetic example, longer treatment schedules (more exposure sessions) are required for patients having severe damage and or life threatening damage such as burns, radiation exposure damage, and or a high percentage of organ injury and or loss of function.

The current invention encompasses administering a complete treatment schedule of the narrow and specific 0.6180 Hz continuous sine wave frequency therapy to a patient for suppression and or complete remission of EMF (electromagnetic frequency) poisoning, such as from cell phone radiation, cell tower radiation, including 5G, Wi-Fi radiation, relay tower radiation.

Pandemic

In certain prophetic examples and embodiments encompasses apparatuses and methods for the systemic and or targeted administration of the complete ULF emergency treatment preferably as needed to a human patient for suppression and or complete remission of a wide variety of pandemic diseases, further encompassing diseases of an unknown etiology.

Profiling Potential Patients

In several specified prophetic examples and embodiments, the apparatuses and methods of the current invention encompass employing a variety of safety measures that do not permit any interference frequencies and or exposure treatment programs outside of the narrow and specific 0.6180 Hz sine wave frequency that do not conform to the pre-defined safety parameters as disclosed herein to treat a human patient.

The current invention preferably encompasses a patient interview that includes inclusion and or exclusion parameters such as mental disorders that are a direct result of the brain wave, brain cell functions, including injury or damage to brain cells, and or brain cell's DNA.

In a preferred embodiment, the current invention encompasses measuring the patient's blood plasma levels, including salinity, and or optionally electrolyte content, and further includes adjusting the immersion tank's salinity, and or optionally electrolyte content, to individually match the patient's plasma saline content, and its associated vibrational frequency, to reduce the frequency distortion arising from transmissive differences between the patient and the water.

The current invention encompasses that the preferred human patient age to initiate administering a complete ultra-low frequency therapy treatment schedule is about 5 years old, depending greatly upon the condition and or disease of the human patient, the preferred therapeutic gain (human enhancement), and or the specific application, and can be administered at a younger age in emergency situations.

Assessing Efficacy of ULF Therapy

In a prophetic example the inventors theorize that there will be a variety of measurable medical results (from conventional medical monitoring applications) from the administration of a complete ULF therapy to a human patient as disclosed herein having the results confirmed in about 48 to 72 hours from the average patient or sooner.

In a prophetic example the inventors theorize that the administration of a complete ULF treatment schedule frequency obtains about 90% of the therapeutic gain during the administered ULF exposure session, and almost immediately after the frequency therapy drops off and goes down to virtually zero after about 10 hours. The current invention encompasses monitoring/measuring biological effects during the ULF exposure session and or within this 10-hour window, to quantify for the ULF treatment's success or effect.

The apparatus and method according to any claim encompasses that there will be conventional measurable medical results from the administration of the invention's ultra-low frequency therapy In some embodiments, viability and or enhancement of the ULF therapy is measured by assessing the population size of a certain cells, tissues, and or organs, while in some embodiments, specific chemical, biological, and or analytical tests are performed to evaluate the viability of the cells, tissues and or organs.

In other embodiments. ULF therapeutic gain is assessed by expression of certain proteins, further including action spectra(s) representing the patient's biological activity.

The current invention encompasses measuring/monitoring the before and or after bio-stimulative effects of a patient from the administration of the complete ULF treatment schedules, and or extrapolating the therapeutic gain. Depending on the condition, disease, and or injury being treated, and or the frequency stimulated biological enhancement by administering the current invention, various endpoints may optionally be used to assess the efficacy of the treatment schedules (therapies). For example, neurologic function scales may be optionally used to quantify and or otherwise characterize the efficacy of various embodiments described herein. Neurologic function scales generally use a number of levels and or points, each point corresponding to an aspect of the human patient's state and or condition. The number of points for a human patient may be employed to quantify the human patient's current condition, and or monitor improvements in the human patient's state and or condition may be expressed by changes of the number of points. One example neurologic function scale used as a clinical tool for diagnosis and or determining severity of Parkinson's disease is the Unified Parkinson's Disease Rating Scale (UPDRS) which comprises various sections evaluated by patient interviews and clinical observations. In certain embodiments, two or more of the neurologic function scales may be used in combination with one another, and may provide longer-term measurements of efficacy (e.g., at three months) or longer, over decades.

Other conditions, disorders, diseases and or injuries that are treated with the current invention's complete ULF treatment schedules may be assessed by standard clinical measures related to that suspected condition, disorder, disease and or injury. For example, treatment of cardiac tissue damage after Ml may be evaluated by conventional medical measurements such as total cardiac output, echocardiography to measure ventricular functions, and or stress testing to measure a patient's overall cardiovascular state and performance characteristics. The therapeutic effects from administration of the invention's complete ULF treatment schedule for frequency stimulated repair and enhancement, may further encompass measuring release (mobilization) of enhanced stem cells and or measuring the enhanced stem cell's secretions as needed in the physician's art.

The current invention encompasses monitoring the efficacy of the complete ULF treatment schedules administered to a patient and or monitoring cellular respiration, such as but not limited to ATP production, ATP activity, oxygen metabolism, surficial oxygen content, and or circulation in real time and the like.

Certain embodiments utilizing FST as described herein are based at least in part on the monitoring/metering findings disclosed herein for assessing and or subsequently adjusting the optimized frequency, wave form characteristics (such as wavelength and wave height), wattage timing (frequency generation intensity), distance between ULF emitting source and the patient (inverse square), and or the stimulation energy density (stimulation energy per unit area, in watts, and the watt frequency multiplied by the frequency exposure time) of the FST energy administered to, and absorbed by, the patient as an important factor in determining the relative efficacy for repair, expansion of normal human mortality, and or enhancement further including selecting the preferred treatment schedule as disclosed herein.

The current invention encompasses that the administered ULF therapy efficacy is directly related to the total emitted power and or the total stimulation energy delivered to the patient's tissues from the ULF apparatuses and methods described herein.

As an example the current invention further encompasses administration of a complete ULF therapy in conjunction (as an adjunct) with prior art stem cell therapies.

In some prophetic examples and embodiments ULF administration delivered within a certain range of watts and or frequency stimulation energy densities provides the desired bio-stimulative and other beneficial biological effects, including systemic genetic repair and enhancement (note the average human has about 400 genetic flaws), within the systemic frequency exposed intracellular and or extra cellular environment, including systemic and or localized effects such that proper homeostasis and function is returned to previously nonfunctioning and or poorly functioning cells, tissues, organs, including mitochondria in the human patient, and further including neurons, which are at risk of necrosis due to hypoxia, acidosis, inflammation, etc.

As for example the beneficial systemic biological effects include cellular effects, but are not limited to interactions within the patient's frequency exposed tissue and cells, and further facilitate systemic production of ATP thereby feeding energy to injured cells which have experienced decreased blood flow due to accident, injury, stroke and or other cardiac events.

Detox Therapy

The current invention encompasses optionally administering a systemic detoxification therapy to a patient prior to, during, and or after the administration of the complete ULF treatment schedule particularly for obtaining longevity assurance. Systemic detoxification prior to administering the complete ULF treatment schedule is most preferred.

The current invention encompasses optionally administering a systemic detoxification therapy to the human patient, preferably administering before, further including during and or after, the complete ULF treatment schedule to optimize the patient's systemic biological environment to optimize both the ULF therapy and stem cell treatment therapy.

The current invention encompasses administering a systemic detoxification treatment schedule of the human patient such as by the oral administration of activated charcoal, such as by the administration of BAL (British anti-lewisite), such as by oral and or I.V. administration of Calcium EDTA and or Sodium EDTA, and or other suitable chelators as needed, and or optionally orally administering MSM (Methylsulfonylmethane) with Acerola Vitamin C, preferably dosing ranging between about 3,000 to 5.000 mg of MSM and 3,000 to 5,000 mg of Acerola Vitamin C per 24 hours for a 70 k/150 Lb. male.

Nutrient Support

In a specified embodiment encompasses administering nutrient support therapy, reference Table 1, in conjunction with a complete ULF treatment schedule to a patient, including a patient suspect of having or diagnosed with a serious condition, injury, and or disease, and or to patients to obtain enhanced human longevity.

In a specified embodiment encompasses a post ULF treatment administration of nutrient support for replenishing sugars, such as administering orange juice, to a patient.

Nutrient support may optionally be administered to a human patient, preferably before, during, and or after completion of a complete ULF treatment schedule, administered as long as needed.

Note the below optional nutrient support dosages shown in Table are based on administration to a 70 kilo/150 lb. male per 24 hours, or as needed.

The current invention encompasses that accurate dosing of the nutrient support (profile) may be calculated from calculations and other experimentations for calculating patient doses for individualized treatment.

The administered nutrient support may optionally include proteolytic and or digestive enzymes as needed, such as administered between meals and or such as with a meal, as needed.

Administered Per 24 Hours

TABLE 1

| Nutrient Support | Dosage |
| --- | --- |
| B3 (methyl nicotinate) | 20 to 30 mg |
| B6 (pyridoxine) | 25 to 100 mg |
| B12 (cyanocobalamin) | 10 to 100 mg |
| B2 | 100 mg to 300 mg |
| B17 | 250 mg to 500 mg |
| Coenzyme Q-10 ubiquinone | 50 mg to 1,200 mg (Administering a loading dose for 7 continuous days prior to the ULF therapy) |
| Coenzyme Q 10 (ubiquinone) Carbonate | 10 to 30 mg (Dosed as needed) |
| potassium (preferably as phosphate, gluconate and/or acetate) | 100 to 500 mg |
| potassium citrate | 50 to 200 mg as needed |
| potassium salt | 50 to 300 mg |
| Calcium | 800 mg |
| magnesium salt, such as citrate | 50 to 250 mg as needed |
| manganese (citrate or orotate) | 1 to 20 mg |
| iodine | 10 to 40 mg |
| selenium (Selenomethionine) | 5 to 20 mg |
| vanadium (vanadyl sulfate) | 1 to 5 mg |
| zinc (gluconate/asporotate) | 3 to 20 mg |
| Vitamin D2 | 1,000 to 3,000 IU |
| Vitamin D3 (cholecalciferol) | 1,000 to 4,000 IU |
| Calcium | 1,200 mg to 2,800 mg |
| Vitamin A | 1,000 to 3,000 RJ |
| Vitamin C | 500 to 1,500 mg |
| Superoxide dismutase | 10 to 1,000 mg, preferably 50 to 100 mg |
| DHEA | 25 mg to 1,200 mg |
| Thyroid | 15 mg to 50 mg |
| Vitamin - E | 100 mg to 1,000 mg |
| malic acid | 1,200 mg to 2,800 mg |
| L-Histidine (Free Form) | 75 mg |
| L-Isoleucine (Free Form) | 75 mg |
| L-Leucine (Free Form) | 75 mg |
| L-Lysine (as L-L-lysine HCl) (Free Form) | 75 mg |
| L-Methionine (Free Form) | 75 mg |
| L-Phenylalanine (Free Form) | 75 mg |
| L-Threonine (Free Form) | 75 mg |
| L-Valine (Free Form) | 75 mg |
| Magnesium | 350 mg to 450 mg |
| Potassium | 300 mg to 500 mg |

TABLE 1-continued

| Nutrient Support | Dosage |
|---|---|
| Boron 2.5 mg to 6 mg | 2.5 mg to 6 mg |
| Sodium | 2,000 mg to 4,000 mg |
| Full carotenoid group including other pigments | (dosed as needed) |
| Vegetal analog of pancreatin | 286 mg |
| Acid stable protease 12 mg | 12 mg |
| Lipase 125 mg | 125 mg |
| Alpha-amylase | 52 mg |
| Amyloglucosidase | 12 mg |
| Cellulase | 5 mg |
| Hemicellulase 3 mg | 3 mg |
| Lactase 5 mg | 5 mg |
| Sucrase | dosed as needed |
| Lycopene | 20 mg to 60 mg |
| Protein | 61 to 128 grams |

Treatment Schedules

In several specified embodiments encompasses frequency stimulated repairing and enhancement includes complete treatment schedules of the current invention that are apparatus driven methods. The systemic administered methods are most preferred.

In certain prophetic examples and embodiments, administering a complete ULF treatment schedule is combined with other types of therapies as an adjunct for an improved therapeutic biostimulative frequency stimulated effects, and may be administered during the treatment pause time periods.

Note some human patients will respond (repair) much sooner, some may take longer, and the current invention complete treatment schedules encompasses monitoring and observing when sufficient biological repair and enhancement occurs in the patient.

The current invention encompasses that a 'complete treatment schedule' refers to any administration of the ULF treatment as described herein, and the following descriptions are not limiting.

Treatment Schedule No. 1

The current invention encompasses a complete treatment schedule comprising at least one 15-minute exposure session for administering the narrow and specific 0.6180 Hz sine wave frequency therapy.

The current invention encompasses a treatment schedule No. 1 administering a complete treatment schedule emitting the narrow and specific 0.6180 Hz continuous sine wave frequency therapy administering an emitted power ranging between about 0.01 to 10 watts to a patient wherein the frequency stimulation therapy within a complete treatment schedule encompasses one single 15 minute ultra-low frequency exposure session, and further includes administering a portion of a treatment schedule.

In a prophetic example, the inventors theorize that the preferred 15-minute exposure session is the preferred frequency dosing exposure time in which the human patient's body absorbs ULF information, and processes the ULF through the brain producing the rearrangement of the neurological network that is representative of the desired therapeutic gain and or end effect, including prophylaxis, suppression, and or complete remission of diseases, disorders, injuries, and conditions, as needed in the physician's medical art.

In a prophetic example, note the inventors theorize the ULF treatment schedule works on a subatomic scale, and that it takes about 15 minutes for a neutron to decay into a proton and an electron, thus this is the natural and preferred timing in physical reality for the absorption of the sufficient ULF data that produces a localized and systemic human repair change and human enhancement change as disclosed herein.

The inventors theorize in a prophetic example that generally a single exposure session longer than about 15 minutes would not yield any more significant therapeutic gain in a patient.

The inventors theorize in a prophetic example that administering a complete ULF treatment schedule operates (repairs and enhances) on sub cellular structures, including cellular and sub cellular structures, including ionic effects, further including nano-technology, due to the extremely narrow and specific 0.6180 Hz frequency and sine wave form administered within a complete treatment schedule.

The current invention ULF apparatuses and methods comprise placing the frequency emitting apparatus at a preferred distance (inverse square) from the human patient as described herein or as needed depending upon application.

The current invention ULF apparatuses and methods comprise placing the frequency emitting apparatus at a preferred distance (inverse square) from the human patient to optimize the efficacy of the biometric entrainment that is further related to the phase of the actual emitted sine wave form, taking into account phase dynamic cancelation and or amplification characteristics, further including the smearing effect of the 0.6180 Hz sine wave form phase as it is moving through the biological medium.

Note frequency dosages will depend upon the patient's biological age, condition and or weight, and the like.

In a prophetic examples the current invention encompasses providing previously unavailable systemic repair and human enhancement characteristics on a subatomic level, and therefore the 15-minute exposure sessions is a sufficient dosing for the re-programming of the patient's entire biological system that will further produce a human enhancement effect and or change in a fundamental way to a new previously unavailable levels and or dimensions of sub-cellular repair and enhancement, including ionic and or nano-technology, preferably immediately followed by a resting and or testing period and or adjusting the treatment schedule if needed or necessary.

The current invention encompasses preferably employing a pause time (resting and or testing period) between exposure sessions of about 3 to 5 hours between each 15-minute frequency exposure session.

The length or duration of administering the complete ULF preferred treatment schedules for frequency stimulation treatments may depend on several factors, including the functional recovery of the human patient, such as expressed through the results of conventional imaging analysis of the patient. In certain embodiments, one or more frequency stimulation treatment schedules parameters may be adjusted in response to a feedback signal from a device (e.g., magnetic resonance imaging) monitoring the human patient.

In certain prophetic examples and embodiments, the a complete FST treatment schedule produces measurable improvements in the human patient's physiological condition. In certain such embodiments, the improvements in the human patient's physiological condition corresponds to a change in the number of points indicative of the human patient's condition, including a complete ULF treatment schedule producing a change of one point, a change of two points, a change of three points, or a change of more than three points, such as on a conventional standardized neurologic function scale.

The current invention encompasses as an option that the refractory period (3 to 5 hour resting and testing period) may be varied depending on the patients age, weight and or condition, such that greater or lesser refractory periods may be accommodated by adjusting the ULF therapy's duty cycle.

For example, in some embodiments, the duty cycle is adjusted to provide complete FST according to the patients age, weight and or condition and or targeted outcome.

In some prophetic examples and embodiments, synchronization of FST therapy repairs and enhances the function of the ULF exposed cells in a human patient depending on the treatment schedule employed. For example, synchronizing the ULF therapy with the refractory period of a sensory neuron, in some embodiments, increases the rate of sensory transmission in the neuron, which, in some embodiments, produces heightened (improved) sensory capacity in a patient. Additionally, synchronization of the complete FST with the refractory period of motor neurons, in some embodiments, stimulates normalization of neuronal firing rates, thereby increasing the patients fine motor control and/or serving as a therapy for palsies and or other such uncontrolled muscle movements by administering a complete treatment schedule (e.g., completing treatment prior to and or between other treatment regimens).

Treatment Schedule No. 2

The current invention encompasses a treatment schedule No. 2 administering a complete treatment schedule emitting the narrow and specific 0.6180 Hz continuous sine wave frequency therapy administering an emitted power ranging between about 0.01 to 10 watts to a patient wherein the frequency stimulation therapy within a complete treatment schedule encompasses three exposure sessions of about fifteen minutes each administered per twenty four hours, preferably having a resting and testing period of about 3 to 5 hours between each exposure session, administered daily for seven consecutive days for systemic prophylaxis, repair and or suppression and or complete remission of any condition and or disease.

In certain prophetic examples and embodiments, the complete ULF repair and enhancement treatment schedules may be terminated after one complete treatment session, while in other embodiments, the complete ULF repair and enhancement treatment session may be repeated for at least two complete treatment schedule periods. The resting and or testing schedules between subsequent complete ULF systemic repair and enhancement to obtain significant extension of normal mortality and longevity assurance for human enhancement may further include resting and or testing schedules between treatment schedules that may be about 5 to 10 years for long term significant extension of statistically normal mortality, barring any significant accidents.

In a prophetic example, the current invention encompasses administering a complete ULF treatment schedule to bring the patient's system back into equilibrium, which theoretically has the effect of creating longevity beyond a statistically normal lifespan.

In some cases, such as where the disease is degenerative (e.g. Alzheimer's disease and or C.T.E.) or where treatment is given to a generally healthy human patient for longevity assurance or extension of normal mortality, the complete ULF human enhancement treatment schedule may continue at chosen intervals and or indefinitely or as needed. The precise administered watt dosing range selected for complete ULF therapy for treating the human patient will depend on a number of factors, and may be adjusted to be combined with any other therapeutic agent or agents, especially nutraceutical and or pharmaceutical agents to achieve the desired systemic biological repair and systemic enhancement effects. The selected watt dosing will again depend on a number of factors, including the additional therapeutic agent or agents and or nutrients chosen and administered, and or the current clinical condition of the patient.

Treatment Schedule No. 3

The apparatus and method according to any claim encompasses treatment schedule No. 3 administering to a patient a complete treatment schedule emitting the narrow and specific 0.6180 Hz continuous sine wave frequency therapy administering an emitted power ranging between about 0.01 to 10 watts to a patient, wherein the frequency stimulation therapy within a complete treatment schedule encompasses three exposure sessions of about fifteen minutes each administered per twenty four hours, preferably having a resting and testing period of about 3 to 5 hours between each exposure session, administered daily for seven consecutive weeks.

Note some rare human patients may require treatment schedules longer than seven consecutive weeks.

The complete ULF treatment schedule therapy for extension of normal mortality may be terminated after one complete treatment schedule, or the frequency treatment schedule may be repeated, preferably having about 5 to 10 years passing between each treatment schedule for extension of normal mortality, primarily obtained from systemic ULF therapy. Optionally the time periods between treatment schedules may be longer, even decades.

The current invention encompasses preferably employing about a 3 to 5-hour pause time (resting and or testing period) between each preferred 15-minute frequency exposure session followed by a resting and or testing period and the current invention complete treatment schedules encompass monitoring and observing when sufficient repair and enhancement occurs.

In certain prophetic examples described herein, a continuous sine wave ULF administration to a patient is preferred that provides a safer, simpler and genetically enhancing more efficacious production and or mobilization of stem cells producing significantly increased production (potentially in the billions of stem cells), proliferation, differentiation, engraftment, and the like preferably produced from the human patient's own cells, that simultaneously enhances the stem cell secretions, thus providing a previously unavailable overall efficacy of systemic stem cell therapies in general. The administered continuous sine wave frequency provides higher peak exposures for shorter systemic therapy times, thereby providing more power to propagate more enhancing of stem cells.

In several prophetic examples described herein, a human patient is administered a complete ULF therapy producing and maintaining an accurate preferred continuous sine wave frequency having parameters that are optimized to systemically stimulate, to support, and or to otherwise enhance interstitial tissue function including intercellular and or intracellular biological processes.

In several prophetic examples described herein, a human patient is administered a complete ULF therapy producing and maintaining an accurate preferred continuous sine wave frequency having parameters that are optimized to systemically produce and maintain systemic gene repair and enhancement including repairing about 400 genetic flaws within the average patient further enhancing their genetic profile.

In several prophetic examples described herein, a human patient is administered a complete ULF therapy producing and maintaining an accurate preferred continuous sine wave frequency having parameters that are optimized to systemically stimulate stem cell repair and enhancement, including production, release, and enhancement.

In certain embodiments, the ULF therapy produces suppression and or complete remission of pH associated conditions, disorders and or diseases such as but not limited to hypoxia, acidosis (localized and or systemic), inflammation, and the like.

In certain embodiments, the ULF therapy encompasses administering a complete ultra-low frequency therapy treatment schedule administering the narrow and specific 0.6180 Hz sine wave frequency therapy to a human patient for systemic therapy for suppression and or elimination of acidosis (reduced pH) that is the primary cause for pain, disease or diseases, tumor metastasis, and or the aging process, thus promoting regeneration.

Treatment Schedule No. 4

The current invention encompasses treatment schedule No. 4 administering complete treatment schedules administered to a patient in a series of contiguous and or non-contiguous frequency treatment schedules emitting the narrow and specific 0.6180 Hz continuous sine wave frequency therapy administering an emitted power ranging between about 0.01 to 10 watts to a patient wherein the frequency stimulation therapy administered within a complete treatment schedule encompasses three exposure sessions of about fifteen minutes each administered per twenty four hours, preferably having a resting and testing period of about 3 to 5 hours between each exposure session, administered for as long as needed to obtain the desired beneficial outcomes.

As an option the current invention treatment schedule No. 4 encompasses administering up to about 300 ULF exposure sessions, or more depending upon the degree of severity of the patient's condition such as regenerating and enhancing a large amount of tissues and or organs.

The apparatus and method according to any claim encompasses administering the narrow and specific 0.6180 Hz frequency therapy to a human patient providing improved athletic performance, endurance, muscle mass, recovery from athletic injuries Treatment Schedule No. 5

The current invention encompasses treatment schedule No. 5 administering a customized complete treatment schedule emitting the narrow and specific 0.6180 Hz continuous sine wave frequency therapy administering an emitted power ranging between about 0.01 to 10 watts to a patient wherein the frequency stimulation therapy within a complete treatment schedule encompasses three exposure sessions of about fifteen minutes each administered per twenty four hours, preferably having a resting and testing period of about 3 to 5 hours between each exposure session, administered until desired beneficial outcomes are obtained by the patient.

Personalized Medicine

The current invention encompasses administering a complete ULF treatment schedule may be adjusted as needed on a case-by-case basis, and further encompasses being individually tailored to the human patient, and further encompasses that accurate dosing of a complete ULF therapy may be calculated from calculations and or other experimentations for calculating doses for individualized treatment schedules, and provides previously unavailable personalized medicine.

In some embodiments, the current invention's FST will augment and enhance the proliferation of endogenous stem cells in a human patient to potentiate the effects of the exogenously produced stem cells. In some embodiments, the complete ULF therapy parameters of a treatment schedule as disclosed herein are pre-engineered to accurately generate a desired bio-stimulative curve of ULF administration over the preferred time and or dose to optimize the bio-stimulative effects as needed in the individual patient.

In some prophetic examples, the complete ULF treatment schedules for human repair and enhancement may be adjusted as needed over time to tailor the treatment schedule (therapy dosing) to the characteristics of a particular human patient (e.g., slightly adjusting the exposure power (watts) times (dosimetry adjustment) based on human patient responsiveness to systemic enhancement therapy.

In-Vitro Genetic Therapy

In several exemplary embodiments of the current invention encompasses that the FST apparatuses and methods are accurately administered employing a pre-programmed in vitro culturing chamber, reference FIG. 24, for producing a wide variety of genetic therapy protocols, whether it be for immediate treatment (re-administration) to a human patient, cryo-storage for future use, and or for human enhancement and or conducting research.

The current invention encompasses administering a 0.6180 Hz sine wave frequency treatment for cellular based therapy research, and or other health research not defined herein.

Note that the average human patient has about 400 genetic defects.

In-Vivo Genetic Therapy

Several exemplary prophetic examples and embodiments of the current invention encompasses that the complete FST apparatus and methods are administered to a human patient in vivo for a wide variety of systemic genetic repair and genetic enhancement, further including stimulating increased energy, increased vitality, and or an increased feeling of well-being.

Several exemplary prophetic examples and embodiments of the current invention encompasses administering a complete ultra-low frequency treatment schedule emitting the narrow and specific non-invasive and drug-free 0.6180 Hz sine wave frequency therapy to a human patient for systemic gene therapy.

Several exemplary prophetic examples and embodiments of the current invention encompasses administering a complete ultra-low frequency therapy treatment schedule administering the narrow and specific 0.6180 Hz continuous sine wave frequency therapy to a patient for enhanced genetic therapy in vivo (inside the body) employing a treatment system from the group consisting of: a vibrating table system, a pod system, a treatment capsule system, a frequency containment shell system, a treatment room system, an immersion tank system, a hand held pistol emitter system, a wristband emitter system, a probe system, a hyperbaric chamber system, and an epidermal patch system.

Genetic Repair and Enhancement

In certain exemplary prophetic examples and embodiments encompasses administering to a human patient, the narrow and specific 0.6180 Hz sine wave frequency including its narrow and specific range of variance is selected so as to produce (e.g., functionally cooperate) localized and or systemic longevity assurance and enhancement.

In several exemplary prophetic examples and embodiments, the complete ULF treatment schedule exposure of the human patient's cells increases the production of stem cell secretions in the frequency targeted tissue and or controls, inhibits, prevents, minimizes, and or reduces apoptosis of the human patient's injured cells, thereby producing measurable beneficial effects, this is an object of the invention.

Once this peak efficiency ULF sine wave reaches the patient's organs and cells, the ULF sine wave will be absorbed by the cells within the organs, and converted to useful nano-scale restructuring energy including stimulating the production and or enhancement of stem cells characteristics, including systemic genetic repair and systemic human enhancement.

In certain embodiments, the ULF emitting source is capable of emitting FST energy at a power level sufficient (watts) to achieve a predetermined efficacy systemically and or at the subdermal tissues. In a prophetic examples, it is presently theorized that a complete ULF treatment schedule therapy of tissue is most effective when systemically exposing the entire human patient to the ULF administration.

In a prophetic example it is theorized that these subsurface power densities are especially effective at producing the desired systemic repair and or biostimulative and or enhancing effects on the patient's cells, tissues and or organs in need of such therapy, further including repairing and correcting virtually all birth defects including genetic defects.

CRISPR

A CRISPR is a family of DNA sequences in bacteria and archaea, and is an abbreviation for Clustered Regularly Interspaced Short Palindromic Repeats.

In certain prophetic examples and embodiments, the complete ULF treatment schedule therapy encompasses eliminating the need for CRISPR processes and its associated systems, and or being administered as an adjunct therapy significantly improving and enhancing the performance of CRIPSR systems, including 'base editing' (specifically replacing individual base pairs at point mutation site, further including eliminating the need for and or significantly improving other gene modification systems, particularly those for human repair and enhancement. This is an object of the invention.

In certain embodiments, the current invention encompasses repairing, optimizing, and or improving prior art genetic therapy systems such as but not limited to CRISPR systems, non-homologous end joining NHEJ and or homology directed repair (HDR), and the like, further administered as an adjunct therapy augmenting and or enhancing other prior art genetic modification systems and technologies.

CRISPR systems have a wide variety of limitations such as requiring significant time and specificity with relatively low probabilities of successful modifications, further including hard-to-transfect cells (stem cells, neurons, hematopoietic cells, etc.) that require more complex patient delivery systems such as those based on lentivirus (LVs), adenovirus (AdV), and or adeno-associated virus (AAV). The current invention complete ULF apparatus and methods treatment schedules overcomes these and other limitations.

ULF Effects on Stem Cells

In several prophetic examples, the current invention encompasses administering ULF stimulation apparatuses and methods, having parameters and procedures as disclosed herein, in several embodiments, that are administered to repair and enhance the efficacy of biological enhancement for extension of normal mortality therapy in a human patient as a stand-alone therapy and or as an adjunct therapy within the rapidly growing field of extension of normal mortality medicine from the previously unavailable systemic complete ULF treatment schedule enhancing effects. Administration of ULF stimulation therapy is an important and significant addition to the selection of therapies to combat injury, degenerative diseases, and or aging that cause cell death and or loss of organ function. This is an object of the invention.

In some prophetic examples and other specified embodiments administering the complete ULF stimulation therapy provides previously unavailable positive effects, for example, but not limited to the human patient's cells, tissues, and or organs, and in some embodiments, ULF stimulation therapy induces stem cell proliferation and or differentiation in response to administration of a complete ULF treatment schedule. As described more fully herein, in several embodiments, this frequency stimulating response is advantageously administered to boost the production and or release/mobilization of stem cells from the patient to combat various aging characteristics and or administered as a prophylactic measure prior to a wide variety of other anti-aging therapies, including surgeries.

In several prophetic examples and other embodiments, FST will enhance the response of the stem cells to pro-differentiation factors, (e.g., growth factors). In several embodiments, FST treatments schedules of the current invention will also improve and or enhance the ability of the patient's own cells, including stem cells, to survive in adverse growth conditions, e.g., inflammation, hypoxic, acidosis states, and or a lack of essential growth nutrients. In some embodiments, frequency stimulation treated cells will respond to chemo-attractants to a greater degree than control cells, indicating enhanced migratory capacity.

In other embodiments, the current invention encompasses an in-vitro cell culturing chamber, reference FIG. 24, for complete ULF administration dosing, for the re-injection of frequency stimulated treated stem cells into a host human patient blood stream, tissue (e.g. muscle, heart, brain) that will yield an enhanced degree of engraftment as compared to untreated stem cells. For obtaining systemic human enhancement in each of these parameters will indicate that frequency stimulated (treated) stem cells have enhanced therapeutic effects, including genetic repair and human genetic enhancement.

Implantation of Enhanced Cells

In several prophetic examples and embodiments, the ULF stimulation therapy is administered to a human patient in simultaneous and or sequential combinations with other stem cell drug processes and therapies (as an adjunct), potentially resulting in enhanced efficacy of a wide variety of prior art stem cell therapies. As an option or optionally the stem cells may be subject to a complete ULF treatment schedule and subsequently re-administered to a human patient by numerous routes, including direct injection, stereotactic-guided delivery, catheter-based approaches, intravascular, topically sprayed on, brushed on, and the like.

In a prophetic example and embodiment, the ULF stimulated stem cells are autologous (self-derived) with respect to the human patient.

In other specified prophetic examples and embodiments, the ULF treated stem cells are allogeneic (donor cells) with respect to the human patient.

In some prophetic examples and embodiments, a complete ULF treatment schedule therapy for human enhancement is manifest as an increased viability of the stem cells.

While in some prophetic examples and embodiments, stem cells are optionally ULF treated then administered to a patient in stem cell transplant procedures, encompassing that certain cell types may present additional benefits for such transplants, and or administering a complete ULF treatment schedule to patient after receiving the stem cell transplant.

In some prophetic examples and embodiments, anti-apoptotic pathways are upregulated in the patient's cells that have been administered with a complete ULF treatment schedule. While not the only factors to consider, ULF administration for obtaining enhanced viability of cells, in some embodiments, is of particular importance, as replacement of damaged and or diseased cells may be the most efficacious when the replacement cell is more likely to survive. This is an object of the invention.

In several prophetic examples and embodiments, ULF stimulation therapy in simultaneous combinations with stem cell therapy potentiates the targeting of stem cell therapy, thereby encouraging a more rapid repositioning of stem cells to a desired location, further including promoting faster healing. This is an object of the invention.

In several prophetic examples and embodiments, engraftment of the stem cells is enhanced by administration of a complete FST treatment schedule. As disclosed herein this may be particularly advantageous in certain therapeutic applications, such as for example stem cell therapy employing an apparatus and method that emits a narrow and specific frequency specifically directed to frequency target tissues that experience shear flow, flex, and or other forces that may dislodge the stem cells. For example, in some embodiments, a complete FST produces cardiac progenitor cells from the human patients own cells including that engraftment is enhanced (as compared to progenitor cells alone). This is particularly advantageous because the blood flow through the heart could wash away the stem cells out of the frequency targeted organ (for example if the frequency target for the cells was an intra-cardiac site). Moreover, the constant flex of the myocardium may dislodge the patient's own stem cells away.

Note in the prior art stem cell injections and or cell transplant therapies generally only employ about 50 to 100 million stem cells per dose, and usually require about 3 to 16 applications.

In several prophetic examples and embodiments, however, the function of the human patient's self-produced stem cells (autologous) are augmented and enhanced by ULF stimulation therapy of the current invention and further encompass obtaining systemic genetic repair and enhancement from systemic ULF sine wave exposure of 0.6180 Hz stimulating the accurate realignment, repair, and enhancement of the patient's genetics to occur. By way of example, FST will promote increased firing of a neuron (derived from a neural progenitor). Similarly, in some embodiments, increased and or enhanced neurotransmitter release results. In some embodiments, alterations in the patient's cell biology occur (e.g., increased or decreased axonal transport) which are beneficial to the functions of the neurons.

In several prophetic examples and embodiments, FST positively impacts the human patient's self-produced and released stem cells which are themselves genetically matched to the patient and frequency enhanced to obtain genetic repair from this specific 0.6180 Hz sine wave ULF exposure for the realignment of the patient's genetics to occur in one or more of the manners disclosed herein.

In some prophetic examples and embodiments, the effects of the FST on the patient's stem cells results in a cascade that yields beneficial effects to the cells of the damaged and or diseased patient tissues, cells, organs. Thus, in some embodiments, the functional characteristics of the stem cells are enhanced in a human patient, which significantly improves stem cell therapy performances that significantly improves stem cell therapy in general. In some embodiments, the complete FST frequency treated stem cells produce enhanced secretions that significantly improve stem cell performances including dormant, damaged, and or diseased host tissue (e.g., the cells are a secretion vehicle for a beneficial effects).

In several prophetic examples and embodiments, the ULF stimulated stem cells and or their enhanced secretions are responsive to the in vivo (inside the body) biological environment in which they inhabit. For example, tissue damage and or disease is often associated with various signaling cascades, such as but not limited to hypoxia and or acidosis, which occurs at a pH range below about 6.8, producing inflammation which determines the outcome of a subset of cells (or the entire tissue). In some embodiments, a complete ULF treatment schedule therapy produces and releases the patient's self-produced (autologous) stem cells that are naturally genetically compatible, and further include these enhanced stem cells detecting, and subsequently releasing secretions that respond to a milieu of conditions, damage, diseases, and further improves the systemic inflammatory environment, including hypoxic and acidotic states, and or its signals, particularly in the ULF treated cells and tissues.

In several prophetic examples and embodiments (as discussed above), certain characteristics of the human patient's own self-produced and genetically compatible cells (autologous) including their secretions advantageously alter the patient's state including the survival and or function of the patient's self-produced genetically compatible cells and or the cells of the human patient's host tissue.

In some embodiments, other progenitor cell types possess similar environmentally-responsive characteristics. Such cells, having the ability to respond to local signals, generate secretions having counteractive local and or paracrine signals, and effectively alter the local cellular environments PHE and or PHI in a beneficial (e.g., pro-survival and or regeneration of function) manner. Such stem cells secretions are particularly advantageous in allogeneic therapies, though in some embodiments, they may be used in optional autologous (self-derived) stem cell therapeutic treatments.

By way of prophetic example, the additional optional adjunct therapy agents may be selected from the group consisting of pharmaceutical compounds, such as but not limited to cytokines, growth factors, trophic factors, neurotransmitters, hormones, transcription factors, monoclonal antibodies, polyclonal antibodies, venom, and or signal transduction molecules, and the like. In several prophetic examples and embodiments, the agent or combination of agents may have the effect of stimulating and or mobilizing progenitor cells.

Organ Transplants

In several specified prophetic examples and embodiments, the current invention encompasses apparatuses and methods for administering a complete ULF treatment schedule, including employing transportable ULF systems, as a stand-alone therapy and or as an adjunct therapy with organ transplanting processes and procedures including exposing the donor organ to the ULF prior to and or during removal and or transport, preferably ULF exposing the donor patient and the receiving patient before and or preferably frequency treating a complete treatment schedule to the human patient after the transplant surgery is completed.

Also as an option the ULF could be administered prior to organ transplant to stimulate the organ(s) biological repair and enhancement of the patient's systemic environment to stimulate and or regenerate and or enhance the patient's organ(s) during and or prior to its removal, transportation, and insertion in a recipient patient, such as for reducing and or eliminating rejection, improving safety, significantly extending the organ(s) preservation beyond the conventional 'golden hour', and further enhancing the organ or organs.

In several specified prophetic examples and embodiments, the current invention encompasses administering a complete ultra-low frequency treatment schedule emitting the narrow and specific 0.6180 Hz sine wave frequency therapy to a blood transplant to significantly reduce or eliminate rejection of the blood.

In several specified prophetic examples and embodiments, the current invention encompasses administering a complete ultra-low frequency treatment schedule emitting the narrow and specific 0.6180 Hz sine wave frequency therapy to a transplanted organ or organs prior to its installation into the human recipient with a frequency exposure session of 15 minutes that is administered 3 times per day (about every 3 to 5 hours) or as needed to stimulate the enhanced biological environment for regenerating and enhancing the human patient's organs after the installation into a human patient.

In several specified prophetic examples and embodiments, the current invention encompasses administering a complete ultra-low frequency treatment schedule administering the narrow and specific 0.6180 Hz sine wave frequency therapy to a patient to frequency stimulate stem cell production in a donor patient and then extract the donor's blood.

In several specified prophetic examples and embodiments, the current invention encompasses administering a complete ultra-low frequency treatment schedule administering the narrow and specific 0.6180 Hz sine wave frequency therapy to a patient to systemically frequency stimulate the donor patient's biological environment, including the organ or organs to be donated and then harvesting the donor's organ or organs.

In several specified prophetic examples and embodiments, the current invention encompasses administering a complete ultra-low frequency treatment schedule administering the 0.6180 Hz sine wave frequency therapy to an organ being transported to frequency stimulate the transported organ during its transportation for preserving and enhancing the harvested organ.

In several specified prophetic examples and embodiments, the current invention encompasses administering a complete ultra-low frequency treatment schedule administering the narrow and specific 0.6180 Hz sine wave frequency therapy to an organ transplant recipient to frequency stimulate the systemic biological environment including the transplanted organ or organs, and promoting faster healing, including decreasing scar tissue and adhesion formation.

After the optional in vitro (outside the body) administration of a complete ULF treatment schedule to an organ(s), the organ(s) may optionally be transplanted to a recipient site in a human patient. In certain embodiments, administering the complete frequency treatment prior to the transplantation and or implantation may include culturing organ(s) sufficient for long term storage, such as the future storage and or implantation etc.

The current invention encompasses the administration of a complete ULF therapy dosage for cells, tissues, and or further including whole organ transplants to significantly increase the survivability by administering a complete treatment schedule, such as but not limited to administering from the transportable ULF emitting pistol and or the ULF in vitro processing treatment chambers of the current invention.

The recipient frequency targeted site or sites may be a site of injury, condition, illness, disease and or defect, and or it may be a region of relatively healthy tissue. In certain embodiments, the frequency targeted recipient site and/or the region surrounding such site is treated by administering a complete ULF stimulation therapy according to the apparatus and methods described herein.

Transfusions

In a prophetic example, the current invention encompasses apparatuses and methods of administering a complete ULF treatment schedule therapy at different stages during blood banking and or transfusions, preferably systemically ULF treating the donor prior to blood donation, and or preferably frequency treating the blood after retrieval (in vitro), further including optionally ULF treating the blood just prior to transfusion into a recipient patient, and or preferably administering a complete ULF treatment schedule therapy to a recipient patient before and or after blood transfusion.

In certain embodiments, the apparatus and method of the current invention encompasses administering a complete ULF treatment schedule(s), such as ULF administration of 0.6180 Hz sine wave, preferably continuously maintaining a window of frequency variance (accuracy) 0.0001 Hz or more specific as disclosed herein for a preferred exposure duration of about 15 minutes administered per treatment session about every three to five hours or as needed preferably having an emitted power ranging between about 0.01 to 10 watts as a stand-alone therapy and or as an adjunct frequency therapy for blood transfusion(s) to stimulate a wide variety of benefits such as genetic repair and genetic enhancement for increasing safety, and the inventors theorize further provides faster, safer, non-invasive, and or sterile blood transfusion that extends the shelf life, virtually eliminates contamination, reduces genetic and immunological rejection, and further enhances the blood's performance characteristics, reference FIG. 24.

In certain embodiments, the apparatus and method of the current invention encompasses administering a complete treatment schedule of the narrow and specific 0.6180 Hz continuous sine wave frequency therapy to a patient wherein employing the treatment therapy at different stages or levels during blood transfusions including: administering a complete ultra-low frequency treatment schedule to the donor prior to blood donation, treating the blood after retrieval (in vitro), including treating the blood prior to transfusion into the recipient patient, and or exposing the recipient patient to the ultra-low frequency treatment schedule after blood transfusion.

Prophetic Treatments

In a prophetic example the inventors theorize that as an extreme example for treating a 25% damaged heart is repaired, including completely repaired, and or enhanced by administering about 200 exposure sessions of 15 minutes each.

In a prophetic example the inventors theorize that as an extreme example for restoring a 25% damaged liver that has damage and is repaired, including completely repaired, and or enhanced by administering about 30 exposure sessions of 15 minutes each.

In a prophetic example the inventors theorize that as an extreme example for restoring a 25% damaged kidney that has damage and is repaired, including completely repaired, and enhanced by administering about 15 exposure sessions of 15 minutes each.

Depending upon which organ or organs and which state, condition, and or disease, somewhere between 10% to 50% of remaining damaged human organ has to be present for it to be restored and or repaired, including completely repaired and enhanced, depending upon what specific organ or organs.

In a prophetic example the complete ULF treatment schedule therapy of the current invention encompasses significant improvements and enhancements in the human patient's production of ATP (adenosine tri-phosphate) and or increasing the ATP activity by up to about 60%.

In a specified embodiment, the current invention encompasses methods and apparatuses employing new materials and or alloys that are yet to be invented that will be automatically encompassed within the current invention.

In a prophetic example, the inventors theorize that new stem cells will be manufactured from certain proteins in the body, however they will take their queue, even more importantly, from the idea of the resonant relationship between the 0.6180 Hz frequency and the frequencies given off electromagnetically by the heart, because this is how stem cells are given their coding to begin with—from the heart, which is the first thing to form in the embryo. The inventor further theorizes that the beating of the heart sends out codifications through electromagnetic energy that creates the idea of what stem cells shall become.

In a prophetic example, the inventors theorize that the resonant 0.6180 Hz sine wave frequency is in a proportional ratio, a harmonic ratio to the rhythm of the heart and the electromagnetic waves being emanated from the heart, to be most efficient in terms of the idea of recoding and enhancing the cells, including their communication and performance characteristics.

In a prophetic example, the inventors theorize at the point of fetal development of the heart, the fetal cells that are being formed are designed, or programmed, from the frequency of the heart at this point when the heart is initially developing, which is 0.6180 Hz. The ULF 0.6180 Hz frequency that is administered thus entrains the systemic physiology of the body to that initial frequency instruction.

In a prophetic example the inventors theorize that the rate of the stem cell generation is a result of increasing the amplitude (power) of the emitted ULF frequency; such that the larger amount of power (watts) will result in a more efficient generation, and a higher number of generations of stem cell production.

In a prophetic example, the inventors theorize that once the patterning 0.6180 Hz frequency has been administered, the patient can then entrain their genetic structure to recognize the pattern and subsequently repair itself without requiring additional ULF treatment schedules from that point forward, after only a few sessions.

In a prophetic example, the inventors theorize that the primary biological mechanism of action of the ULF therapy is in the interstitial fluid matrix, as this matrix interconnects and influences all biological systems.

In a prophetic example, the inventors theorize that the basal fundamental translation of electromagmatheric or energetic template reality into physical reality, arises though the interstitial fluid matrix as one of the translation points, and as a primary and significant point of influence.

In a prophetic example the inventors theorize that the ULF therapy optimizes the structure of microRNA throughout the patient.

In a prophetic example, the inventors theorize that the interstitial fluid in its fractal matrix acts as an interim phase transition between electro-magnetheric energy and physiological crystallization.

In a prophetic example, the inventors theorize that a complete ULF treatment schedule provides the 0.6180 Hz sine wave entrainment frequency to systemically entrain the interstitial fluid to be at its most optimized 0.6180 ratio for dynamic movement.

In a prophetic example, the inventors theorize that a complete ULF treatment schedule systemically optimizes the biological system up to a certain point (systemic enhancement capacity).

In a prophetic example, the inventors theorize that if administering a ULF treatment schedule exposure session longer than 15 minutes, it is preferred to optionally switch the administered wave form, such as switching between a sine wave form and a saw tooth wave form.

In a prophetic example, the inventors theorize that a complete ULF treatment schedule provides a patient's neurological circuitry (brain) to become more super and hyper conductive. Therefore, the transmission of any form of energy along the neurological net, or through the cells, such as across any communication system through the body, will allow there to be a frequency opening, thus raising of the frequency capacity that can allow for access to more information and the application of that information in a more intelligent way, therefore, the ULF therapy raises the patient's intelligence and improves the patient's mental clarity.

The inventors theorize that the average surface charge of a healthy cell is about 2.5 to 5 mV (microvolts).

The inventors theorize that the average surface charge of a stem cell is about 5 to 10 mV (microvolts).

In a prophetic example, the inventors theorize that the 0.6180 Hz sine wave treatment wave-form is more effective than a saw tooth wave form, however it is easier to accurately produce a saw tooth wave. Note producing a device for administering an accurate sine wave form is more difficult (complex) than producing a device for administering saw tooth wave, primarily due to producing the complex geometry of the sine wave.

The inventors theorize that the difference in efficacy between a sine wave form administration and a saw tooth wave form administration is that the saw tooth wave form administration is about 0.7 as effective as the sine wave administration (about a 30% difference).

In a prophetic example, the inventors theorize that the 0.6180 Hz sine wave treatment will have a pulsed effect on the cellular structure of the patient as by the time the emitted 0.6180 Hz wave form gets to the cellular structure, it is going to be a pressure that the cellular structure moderates.

In a prophetic example, the inventors theorize that after a human patient has completed puberty, the stem cell performs an additional function of producing growth hormone that spreads throughout the patient's body and captivates any stem cells that are left over and it causes them to become differentiated into greater muscle growth.

In a prophetic example the inventors theorize that the genetic repair and enhancement from the administration of a complete ULF treatment schedule emitting a 0.6180 Hz sine wave frequency is directly related to the ratio of DNA width to DNA length which is 0.6180.

In a prophetic example the inventors theorize that administering a complete ultra-low frequency therapy treatment schedule administering the narrow and specific 0.6180 Hz sine wave frequency therapy to the patient's stem cells and or their bio-active secretions provides the highest percentage of the human patient's enhanced genetic potential, that is furthermore individually tailored to the individual human patient's own genetics.

In a prophetic example, the inventors theorize that administering a complete ULF treatment schedule increase the metabolism of the human patient.

In a prophetic example, the inventors theorize that administering a complete ULF treatment schedule increases cellular detoxification, including the interstitial fluid matrix, so a 15-minute exposure sessions are preferred encompassing resting and testing periods (pause time) of between about 3 to 5 hours in between each exposure session.

In a prophetic example the inventors theorize that administering a complete ULF treatment schedule encourages the interstitial tissue to purge toxins from the proximate cells.

In a prophetic example the inventors theorize that administering CoQ-10 as an adjunct therapy that itself purges, or causes a purging of the interstitial tissue, will optimize the repair and enhancement effects of the ULF therapy when administered to a patient within a complete treatment schedule, such that the interstitial tissue uptakes the cellular toxins, and the Co-Q10 facilitates the purging of the interstitial tissue buildup the toxins that have been collected.

In a prophetic example the inventors theorize that the inventive ULF therapy optimizes the micro-environment at the pericyte-MSC site on the vasculature that creates stem cells to increase the production of stem cells.

What is claimed is:

1. An ultra-low frequency medical treatment apparatus, comprising:
    an ultra-low frequency generating and emitting apparatus comprising:
        a frequency generator apparatus for generating and amplifying an accurate 0.6180 Hz frequency; and
        a frequency emitter apparatus coupled to the frequency generator apparatus that is configured to emit said accurate 0.6180 Hz frequency to a human patient,
        wherein the frequency emitter apparatus transmits the 0.6180 Hz frequency as a continuous wave having a ratio of a wave form incline to a wave form decline of 0.6180.

2. The apparatus according to claim 1, wherein the frequency emitter apparatus transmits the accurate 0.6180 Hz frequency having a window of variance of 0.0001 Hz.

3. The apparatus according to claim 1, wherein the frequency emitter apparatus transmits the 0.6180 Hz frequency at a power ranging between 0.0001 Watts and 15 Watts.

4. The apparatus according to claim 1, wherein the frequency emitter apparatus transmits an electrical current that is less than 0.2 amps.

5. The apparatus according to claim 1, wherein the frequency emitter apparatus emits a voltage less than 20 volts, and is adjustable.

6. The apparatus according to claim 1, wherein the continuous wave is a sine wave.

7. The apparatus according to claim 1, wherein the continuous wave has a wavelength 15 nm and an amplitude of 24.27 nm.

8. The apparatus according to claim 1, wherein the frequency emitter apparatus is selected from the group consisting of: a frequency emitting wristband apparatus, a frequency emitting epidermal patch emitter apparatus, handheld pistol frequency emitter apparatus and a frequency wave guide emitting internal probe apparatus.

9. The apparatus according to claim 1, wherein the frequency emitter apparatus comprises a rotary driver apparatus.

10. The apparatus according to claim 1, wherein the ultra-low frequency medical treatment apparatus comprises a treatment chamber for the human patient that is a complete enclosure.

11. The apparatus according to claim 1, wherein the ultra-low frequency medical treatment apparatus comprises a treatment chamber for the human patient selected from the group consisting of: a treatment room apparatus, an immersion tank apparatus, a vibration table, an in vitro cell culturing chamber apparatus, a treatment pod apparatus, a treatment capsule apparatus, and a frequency containment shell apparatus.

12. The apparatus according to claim 11, wherein the treatment chamber comprises faraday shielding to shield the patient from undesired electromagnetic interference frequencies.

13. The apparatus according to claim 11, wherein the treatment chamber comprises vibration isolating mounts to maintain the accurate 0.6180 Hz frequency continuous wave.

14. The apparatus according to claim 11, wherein the treatment chamber comprises a baffling system to maintain the accurate 0.6180 Hz frequency continuous wave.

15. The apparatus according to claim 11, wherein the treatment chamber comprises a supporting apparatus for the human patient that is configured to moves a position of the human patient during a treatment to enhance a biological entrainment of the human patient to the 0.6180 Hz frequency.

16. The apparatus according to claim 11, wherein the immersion tank apparatus comprises water having a saline content and an electrolyte content that is individually matched to a saline content and an electrolyte content in the patient's blood plasma.

17. The apparatus according to claim 11 wherein the apparatus is configured to administer ultra-low frequency medical treatment in vitro to components of the human patient, said components being selected from the group consisting of human organs, tissues, cells, stem cells, blood, eggs, and sperm.

18. An ultra-low frequency medical treatment apparatus, comprising:
    an ultra-low frequency generating and emitting apparatus comprising:
        a frequency generator apparatus for generating and amplifying an accurate 0.6180 Hz frequency; and
        a frequency emitter apparatus coupled to the frequency generator apparatus that is configured to emit said accurate 0.6180 Hz frequency to a human patient,
        wherein the frequency emitter apparatus comprises an antenna frequency emitting system.

19. The apparatus according to claim 18, wherein the antenna frequency emitting system comprises a conical wave guide transmitter.

20. An ultra low frequency medical treatment apparatus, comprising:
    an ultra-low frequency generating and emitting apparatus comprising:
        a frequency generator apparatus for generating and amplifying an accurate 0.6180 Hz frequency; and
        a frequency emitter apparatus coupled to the frequency generator apparatus that emits said accurate 0.6180 Hz frequency to a human patient,
    wherein the ultra-low frequency medical treatment apparatus comprises a treatment chamber for the human patient selected from the group consisting of: a treatment room apparatus, an immersion tank apparatus, vibration table, a treatment pod apparatus, a treatment capsule apparatus, and a frequency containment shell apparatus, and wherein the treatment chamber comprises an oxygen regulator that regulates an oxygen concentration between 19.5% and 30% within the treatment chamber.

* * * * *